(12) United States Patent
Seo et al.

(10) Patent No.: US 11,401,268 B2
(45) Date of Patent: Aug. 2, 2022

(54) ORGANIC COMPOUND HAVING IMPROVED LUMINESCENT PROPERTIES, ORGANIC LIGHT EMITTING DIODE AND ORGANIC LIGHT EMITTING DEVICE HAVING THE COMPOUND

(71) Applicants: LG Display Co., Ltd, Seoul (KR); Korea University Research and Business Foundation, Seoul (KR)

(72) Inventors: Bo-Min Seo, Paju-si (KR); Dae-Wi Yoon, Paju-si (KR); Joong-Hwan Yang, Paju-si (KR); Dong-Hoon Choi, Paju-si (KR); Su-Na Choi, Paju-si (KR); Hyung-Jong Kim, Paju-si (KR); Mallesham Godumala, Paju-si (KR)

(73) Assignees: LG DISPLAY CO., LTD., Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 231 days.

(21) Appl. No.: 16/715,699

(22) Filed: Dec. 16, 2019

(65) Prior Publication Data
US 2020/0207760 A1 Jul. 2, 2020

(30) Foreign Application Priority Data
Dec. 28, 2018 (KR) .................. 10-2018-0172143

(51) Int. Cl.
*C07D 471/04* (2006.01)
*H01L 51/00* (2006.01)

(52) U.S. Cl.
CPC ........ *C07D 471/04* (2013.01); *H01L 51/0061* (2013.01); *H01L 51/0072* (2013.01)

(58) Field of Classification Search
None
See application file for complete search history.

(56) References Cited

U.S. PATENT DOCUMENTS

| 2015/0349279 A1* | 12/2015 | Li | C09K 11/06 |
| | | | 252/301.16 |
| 2017/0077416 A1* | 3/2017 | Kim | C07D 471/04 |
| 2017/0346012 A1* | 11/2017 | Koo | C07D 471/10 |

FOREIGN PATENT DOCUMENTS

| CN | 105384759 A | 3/2016 | | |
| CN | 106414450 A | 2/2017 | | |
| CN | 107434796 A | 12/2017 | | |
| CN | 109956962 A | * | 7/2019 | |
| EP | 3 029 037 A1 | 6/2016 | | |
| KR | 10-2014-0015385 A | 2/2014 | | |
| KR | 10-2014-0018101 A | 2/2014 | | |
| KR | 10-2014-0076521 A | 6/2014 | | |
| KR | 10-2018-0067950 A | 6/2018 | | |
| WO | WO-2014021569 A1 | * | 2/2014 | ........... C07D 401/10 |
| WO | WO-2018092928 A1 | * | 5/2018 | ............. H01L 51/50 |

OTHER PUBLICATIONS

L. Sicard et al., 123 The Journal of Physical Chemistry C, 19094-19104 (2019) (Year: 2019).*
Hawley's Condensed Chemical Dictionary (16th ed., 2016, R.J. Larranaga ed.) (Year: 2016).*
MA Fox, Organic Chemistry, 133-134 (1997) (Year: 1997).*
Luo et al., "Rational design of isophthalonitrile-based thermally activated delayed fluorescence emitters for OLEDs with high efficiency and slow efficiency roll-off", Dyes and Pigments. vol. 147, Dec. 2017, pp. 350-356.

* cited by examiner

*Primary Examiner* — Alexander R Pagano
(74) *Attorney, Agent, or Firm* — Birch, Stewart, Kolasch & Birch, LLP

(57) ABSTRACT

An organic compound, an organic light emitting diode including the compound, and an organic light emitting device including the organic light emitting diode are disclosed. The organic compound may include a fused hetero aromatic moiety having a p-type property and an aza-acridine moiety having an n-type property bonded to the fused hetero aromatic moiety via an aromatic or a hetero aromatic linker. The organic compound has relatively high energy level since it includes plural fused hetero aromatic rings. Holes and electrons can be recombined in an emitting material layer in a balanced manner since the organic compound has a bipolar property. The organic light emitting diode and the organic light emitting device including the organic compound have enhanced luminous efficiency and luminous lifetime.

22 Claims, 11 Drawing Sheets

ORGANIC COMPOUND HAVING IMPROVED LUMINESCENT PROPERTIES, ORGANIC LIGHT EMITTING DIODE AND ORGANIC LIGHT EMITTING DEVICE HAVING THE COMPOUND

CROSS-REFERENCE TO RELATED APPLICATIONS

This application claims the benefit under 35 U.S.C. § 119(a) of Korean Patent Application No. 10-2018-0172143, filed in Republic of Korea on Dec. 28, 2018, which is incorporated herein by reference in its entirety.

BACKGROUND OF THE INVENTION

Technical Field

The present disclosure relates to an organic compound, and more specifically, to an organic compound having enhanced luminescent properties, an organic light emitting diode and an organic light emitting device including the compound.

Description of the Related Art

Among the flat display devices used widely in present, an organic light emitting diode (OLED) has come into the spotlight as a display device replacing rapidly a liquid crystal display device (LCD). In the OLED, when electrical charges are injected into an emission layer between an electron injection electrode (i.e., cathode) and a hole injection electrode (i.e., anode), electrical charges are combined to be paired, and then emit light as the combined electrical charges are disappeared.

The OLED can be formed as a thin film less than 2000 Å and implement unidirectional or bidirectional images as electrode configurations. In addition, OLED can be formed even on a flexible transparent substrate such as a plastic substrate so that OLED can implement a flexible or foldable display with ease. Moreover, the OLED can be driven at a lower voltage of 10 V or less. Besides, the OLED has relatively lower power consumption for driving compared to plasma display panel and inorganic electroluminescent devices, and color purity thereof is very high.

Since only singlet excitons in the prior art common fluorescent material can be involved in luminous process, luminous efficiency of the common fluorescent material is low. On the contrary, the prior art phosphorescent material in which triplet excitons as well as singlet excitons participate in the luminous process showed high luminous efficiency compared to the common fluorescent material. However, since metal complex as a representative phosphorescent material has a short luminous lifetime, its commercial application has been limited. Particularly, the organic compound for implementing blue luminescence has deficient luminescent properties and short luminous lifetime.

SUMMARY OF THE INVENTION

Accordingly, the present disclosure is directed to an organic compound, an organic light emitting diode and an organic light emitting device including the organic compounds that can reduce one or more of the problems due to the limitations and disadvantages of the related art.

An object of the present disclosure is to provide an organic compound that enhances its luminescent properties, and an organic light emitting diode and an organic light emitting device introducing the organic compound.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

According to an aspect, the present disclosure provides an organic compound having the following Chemical Formula 1:

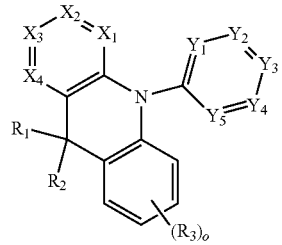

wherein each of $R_1$ and $R_2$ is independently protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or $R_1$ and $R_2$ form $C_5$-$C_{30}$ spiro structure; $R_3$ is protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or adjacent two groups among $R_3$ form $C_4$-$C_{20}$ fused aromatic or hetero aromatic ring; o is an integer of 0 to 4; each of $X_1$ to $X_4$ is independently $CR_4$ or nitrogen atom (N), wherein at least one of $X_1$ to $X_4$ is nitrogen atom, wherein $R_4$ is protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or adjacent two groups among $R_4$ form $C_4$-$C_{30}$ fused aromatic or hetero aromatic ring; each of $Y_1$ to $Y_5$ is independently $CR_5$ or nitrogen atom (N), wherein at least three of $Y_1$ to $Y_5$ is $CR_5$, wherein $R_5$ is protium, deuterium, tritium, linear or branched $C_1$-$C_{20}$ alkyl group, $C_1$-$C_{20}$ alkoxy group or $C_{10}$-$C_{30}$ fused hetero aryl group, wherein the $C_{10}$-$C_{30}$ fused hetero aryl group is unsubstituted or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and combination thereof, fused with a $C_4$-$C_{20}$ aromatic or hetero aromatic ring or linked by a spiro structure of a $C_4$-$C_{20}$ aromatic or hetero aromatic ring, wherein at least one $R_5$ among $Y_1$ to $Y_5$ is $C_{10}$-$C_{30}$ fused hetero aryl group unsubstituted or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and combination thereof, fused with a $C_4$-$C_{20}$ aromatic or hetero aromatic ring or linked by a spiro structure of a $C_4$-$C_{20}$ aromatic or hetero aromatic ring.

According to another aspect, the present disclosure provides an organic light emitting diode (OLED) that comprises a first electrode; a second electrode facing the first electrode; and at least one emitting unit disposed between the first and second electrodes and including an emitting material layer, wherein the emitting material layer comprises the above organic compound.

According to still another aspect, the present disclosure provides an organic light emitting device that comprises a substrate and the OLED disposed over the substrate, as described above.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION OF THE INVENTION

Figure 1:
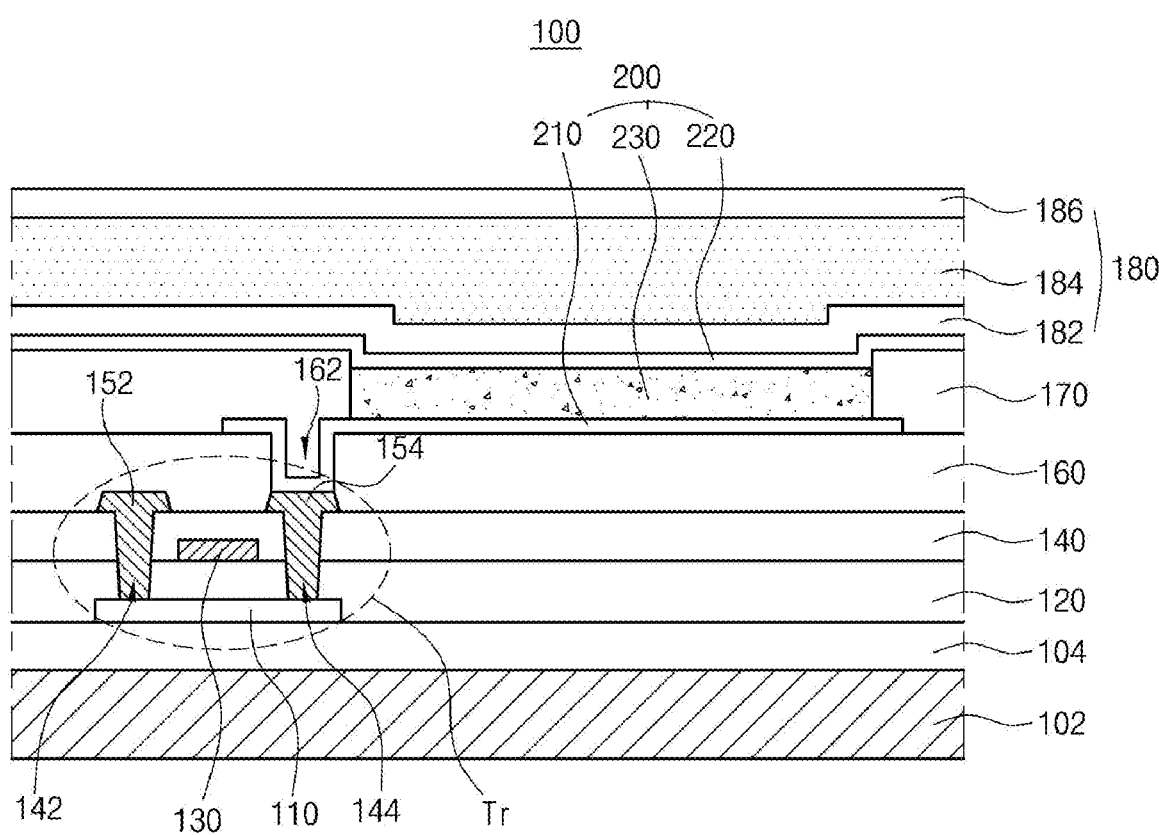
FIG. 1 is a schematic cross-sectional view illustrating an organic light emitting display device of the present disclosure.

Reference will now be made in detail to aspects of the disclosure, examples of which are illustrated in the accompanying drawings.

Organic Compound

An organic compound applied in an organic light emitting diode should have excellent luminescent properties and maintain stable properties during driving the diode. Particularly, luminous material within an organic light emitting diode is the most important factor for determining the luminous efficiency of the diode. Accordingly, the luminous material should have high quantum efficiency as well as mobility for holes and electrons and form stably excitons.

An organic compound of the present disclosure has a structure of an aza-acridine moiety and a fused hetero aryl moiety linked to the aza-acridine moiety via aromatic or hetero aromatic linker. The organic compound of the present disclosure may have the following structure of Chemical Formula 1:

Chemical Formula 1

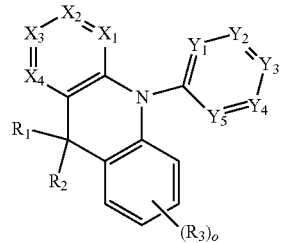

In Chemical Formula 1, each of $R_1$ and $R_2$ is independently protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or $R_1$ and $R_2$ form $C_5$-$C_{30}$ spiro structure. $R_3$ is protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or adjacent two groups among $R_3$ form $C_4$-$C_{20}$ fused aromatic or hetero aromatic ring. o is an integer of 0 to 4. Each of $X_1$ to $X_4$ is independently $CR_4$ or nitrogen atom (N), wherein at least one of $X_1$ to $X_4$ is nitrogen atom, wherein $R_4$ is protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or adjacent two groups among $R_4$ form $C_4$-$C_{30}$ fused aromatic or hetero aromatic ring. Each of $Y_1$ to $Y_5$ is independently $CR_5$ or nitrogen atom (N), wherein at least three of $Y_1$ to $Y_5$ is $CR_5$, wherein $R_5$ is protium, deuterium, tritium, linear or branched $C_1$-$C_{20}$ alkyl group, $C_1$-$C_{20}$ alkoxy group or $C_{10}$-$C_{30}$ fused hetero aryl group, wherein the $C_{10}$-$C_{30}$ fused hetero aryl group is unsubstituted or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and combination thereof, fused with a $C_4$-$C_{20}$ aromatic or hetero aromatic ring or linked by a spiro structure of a $C_4$-$C_{20}$ aromatic or hetero aromatic ring, wherein at least one $R_5$ among $Y_1$ to $Y_5$ is $C_{10}$-$C_{30}$ fused hetero aryl group unsubstituted or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and combination thereof, fused with a $C_4$-$C_{20}$ aromatic or hetero aromatic ring or linked by a spiro structure of a $C_4$-$C_{20}$ aromatic or hetero aromatic ring.

As used herein, the term "unsubstituted" means that hydrogen atom is bonded, and in this case hydrogen atom includes protium, deuterium and tritium.

The substituent as used herein may include, but are not limited to, $C_1$-$C_{20}$ alkyl group unsubstituted or substituted with halogen, $C_1$-$C_{20}$ alkoxy group unsubstituted or substituted with halogen, halogen, cyano group, —$CF_3$, hydroxyl group, carboxyl group, carbonyl group, amino group, $C_1$-$C_{20}$ alkyl amino group, $C_6$-$C_{30}$ aryl amino group, $C_4$-$C_{30}$ hetero aryl amino group, nitro group, hydrazyl group, sulfonyl group, $C_5$-$C_{30}$ alkyl silyl group, $C_5$-$C_{30}$ alkoxy silyl group, $C_3$-$C_{30}$ cycloalkyl silyl group, $C_6$-$C_{30}$ aryl silyl group, $C_4$-$C_{30}$ hetero aryl silyl group, $C_6$-$C_{30}$ aryl group and $C_4$-$C_{30}$ hetero aryl group. As an example, when each of $R_1$ to $R_6$ is independently substituted with alkyl group, the alkyl group may be linear or branched $C_1$-$C_{20}$ alkyl group, and preferably linear or branched $C_1$-$C_{10}$ alkyl group.

As used herein, the term "hetero" described in "hetero aromatic ring", "hetero aromatic group", "hetero alicyclic ring", "hetero cyclic alkyl group", "hetero aryl group", "hetero aralkyl group", "hetero aryloxyl group", "hetero aryl amino group", "hetero arylene group", "hetero aralkylene group", "hetero aryloxylene group", and the likes means that at least one carbon atoms, for example 1 to 5 carbon atoms, forming such aromatic or alicyclic rings are replaced with at least one hetero atoms selected from the group consisting of N, O, S and combination thereof.

As illustrated in Chemical Formula 1, the organic compound of the present disclosure includes an aza-acridine moiety including at least one nitrogen atom on a side fused ring within the molecule. The aza-acridine moiety bonds to the $C_{10}$-$C_{30}$ fused hetero aryl moiety $R_5$ via an aromatic or hetero aromatic linker including $Y_1$ to $Y_5$. In one exemplary embodiment, the $C_{10}$-$C_{30}$ fused hetero aryl group constituting $R_5$ in Chemical Formula 1 may include at least one nitrogen atom. For example, the $C_{10}$-$C_{30}$ fused hetero aryl group constituting $R_5$ may be, but are not limited to, selected from the group consisting of carbazolyl, acridinyl, carbolinyl, spirofluorenocarbazolyl, spirofluorenoacridinyl, phenazinyl, phenoxazinyl and phenothiazinyl.

The aza-acridine moiety in the organic compound of Chemical Formula 1 has excellent electron bonding ability, the aza-acridine moiety may have n-type property inducing electron injection and transportation. Since the $C_{10}$-$C_{30}$ fused hetero aryl moiety has excellent hole bonding ability, the $C_{10}$-$C_{30}$ fused hetero aryl moiety may have p-type property inducing hole injection and transportation. In other word, the organic compound having the structure of Chemical Formula 1 may have bi-polar property.

In one exemplary embodiment, when each of $R_1$ to $R_4$ is independently $C_6$-$C_{30}$ aryl group or $R_5$ is substituted with $C_6$-$C_{30}$ aryl group, each of the $C_6$-$C_{30}$ aryl group may independently be, but are not limited to, unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzo-phenanthrenyl, dibenzo-phenanthrenyl, azulenyl, pyreneyl, fluoranthenyl, triphenylenyl, chrysenyl, tetraphenyl, tetracenyl, pleiadenyl, picenyl, pentaphenyl, pentacenyl, fluorenyl, indeno-fluorenyl or spiro-fluorenyl.

In an alternative embodiment, when each of $R_1$ to $R_4$ is independently $C_4$-$C_{30}$ hetero aryl group or $R_5$ is substituted with $C_4$-$C_{30}$ hetero aryl group, each of the $C_4$-$C_{30}$ hetero aryl group may independently be, but are not limited to, unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzo-carbazolyl, dibenzo-carbazolyl, indolo-carbazolyl, indeno-carbazolyl, benzofuro-carbazolyl, benzothieno-carbazolyl, quinolinyl, iso-quinolinyl, phthalazinyl, quinoxalinyl, cinnolinyl, quinazolinyl, quinolizinyl, purinyl, benzo-quinolinyl, benzo-iso-quinolinyl, benzo-quinazolinyl, benzo-quinoxalinyl, acridinyl, phenanthrolinyl, perimidinyl, phenanthridinyl, pteridinyl, naphthidinyl, furanyl, pyranyl, oxazinyl, oxazolyl, oxadiazolyl, triazolyl, dioxinyl, benzo-furanyl, dibenzo-furanyl, thiopyranyl, xanthenyl, chromenyl, isochromenyl, thioazinyl, thiophenyl, benzo-thiophenyl, dibenzo-thiophenyl, difuro-pyrazinyl, benzofuro-dibenzofuranyl, benzothieno-benzo-thiophenyl, benzothieno-dibenzo-furanyl, benzothieno-benzo-furanyl or N-substituted spiro-fluorenyl.

In one exemplary embodiment, the $C_6$-$C_{30}$ aryl group or the $C_4$-$C_{30}$ hetero aryl group, which constitutes each of $R_1$ to $R_4$ or substitute to $R_5$, may have 1, 2 or 3 aromatic or hetero aromatic ring. When the number of the aromatic or hetero aromatic rings constituting each of $R_1$ to $R_4$ or substituting to $R_5$ is increased, the conjugated structure within the entire organic compound becomes excessively long, so that the bandgap of the organic compound may be excessively reduced. As an example, when each of $R_1$ to $R_4$ is independently aromatic or hetero aromatic group or $R_5$ is substituted with aromatic or hetero aromatic group, each of the aromatic or hetero aromatic rings may be independently, but are not limited to, phenyl, biphenyl, naphthyl, anthracenyl, pyrrolyl, triazinyl, imidazolyl, pyrazolyl, pyridinyl, pyrazinyl, pyrimidinyl, pyridazinyl, furanyl, benzo-furanyl, dibenzo-furanyl, thiophenyl, benzo-thiophenyl, dibenzo-thiophenyl, carbazolyl, acridinyl, carbolinyl, phenazinyl, phenoxazinyl and/or phenothiazinyl.

In another exemplary embodiment, adjacent two groups among $R_3$ or $R_4$ may independently form a $C_4$-$C_{20}$ fused aromatic or hetero aromatic ring and/or a $R_5$ may be fused with $C_4$-$C_{20}$ fused aromatic or hetero aromatic ring. In this case, the $C_4$-$C_{20}$ fused aromatic or hetero aromatic ring may include, but are not limited to, a fused aryl ring such as fused phenyl ring, a fused naphthyl ring and/or a fused indeno ring or a fused hetero aryl ring such as a fused pyridyl ring, a fused pyrimidyl ring and/or a fused indolyl ring.

As an example, adjacent two groups among $R_3$ or $R_4$ may independently form a $C_4$-$C_{20}$ fused aromatic or hetero aromatic ring. In this case, the aza-acridine moiety may be fused with an aromatic or hetero aromatic ring to form a benzo aza-acridine moiety, a dibenzo aza-acridine moiety, a benzofuro aza-acridine moiety, a benzothieno acridine moiety, a pyrido aza-acridine moiety, an indeno aza-acridine moiety and/or an indolo aza-acridine moiety, but are not limited thereto.

In another exemplary embodiment, the $C_{10}$-$C_{30}$ fused hetero aryl moiety constituting $R_5$ may be further fused with another aromatic or hetero aromatic ring to form a benzo carbazole/acridine/carboline/phenazine/phenoxazine/phenothiazine moiety, a dibenzo carbazole/acridine/carboline/phenazine/phenoxazine/phenothiazine moiety, a benzofuro carbazole/acridine/carboline/phenazine/phenoxazine/phenothiazine moiety, a benzothieno carbazole/acridine/carboline/phenazine/phenoxazine/phenothiazine moiety, a pyrido carbazole/acridine/carboline/phenazine/phenoxazine/phenothiazine moiety, an indeno carbazole/acridine/carboline/phenazine/phenoxazine/phenothiazine moiety and/or an indolo carbazole/acridine/carboline/phenazine/phenoxazine/phenothiazine moiety.

In still another exemplary embodiment, $R_1$ and $R_2$ may form a $C_5$-$C_{30}$ spiro structure and/or the $C_{10}$-$C_{30}$ fused hetero aryl group constituting $R_5$ may be linked by a spiro structure of a $C_4$-$C_{20}$ aromatic or hetero aromatic ring. The spiro structure is not limited to a particular structure, but may include a spiro-fluorene structure and a spiro-benzofluorene structure, each of which is unsubstituted or substituted with $C_1$-$C_{20}$ linear or branched alkyl group, $C_6$-$C_{30}$ aromatic group, $C_4$-$C_{30}$ hetero aromatic group, $C_6$-$C_{30}$ aromatic amino group and/or $C_4$-$C_{30}$ hetero aromatic amino group.

Since the organic compound having the structure of Chemical Formula 1 includes the fused hetero aryl moiety, which has the p-type property, and the aza-acridine moiety, which has the n-type property, the organic compound has excellent affinity to the holes as well as electrons. Accordingly, when the organic compound having the structure of Chemical Formulae 1 and 2 is applied an emitting material layer (EML), a recombination zone where holes and electros form an exciton is located in the middle of the EML, not in an interface between the EML and an electron transport layer (ETL) or a hole blocking layer (HBL).

In addition, since the organic compound having the structure of Chemical Formula 1 includes plural fused aromatic or hetero aromatic rings, each of which has a rigid conformational structure, the organic compound has an excellent thermal resistance property. The organic compound having the structure of Chemical Formula 1 has relatively high excited state singlet and triplet energy levels. Moreover, the organic compound has a relatively deep (or low) highest occupied molecular orbital (HOMO) energy level and a relatively shallow (or high) lowest unoccupied molecular orbital (LUMO) energy level. In other words, an energy level bandgap (Eg) between the HOMO energy level and the LUMO energy level of the organic compound is wide. As an example, the organic compound having the structure of Chemical Formula 1 may have the HOMO energy level and the LUMO energy level suitable for use as a luminous material, for example, a host. As an example, when the organic compound is used together with a delayed fluorescent material in the EML, the driving voltage of the OLED may be lowered to reduce the power consumption. Accordingly, the stress applied to the OLED owing to the increase in driving voltage is reduced, thereby improving luminous efficiency and the luminous lifetime of the OLED.

In one exemplary embodiment, the organic compound having the structure of Chemical Formula 1 may have an excited state singlet energy level $S_1$, but are not limited to, equal to or higher than about 3.1 eV and an excited state triplet energy level $T_1$, but are not limited to, equal to or higher than about 2.7 eV. In addition, the organic compound having the structure of Chemical Formula 1 may have a HOMO energy level, but are not limited to, between about −5.5 eV and about −6.5 eV, and preferably between about −5.7 eV and about −6.3 eV, and have a LUMO energy level, but are not limited to, between about −1.5 eV and about −3.0 eV, and preferably between about −2.0 eV and about −2.5 eV. Further, the organic compound having the structure of Chemical Formula 1 may have an energy level bandgap (Eg) between the HOMO energy level and the LUMO energy level, but are not limited to, between about 3.0 eV and about 4.5 eV, and preferably between about 3.0 eV and about 4.2 eV.

In one exemplary embodiment, the organic compound having the structure of Chemical Formula 1 may have a benzo-naphthyridine moiety. For example, one of $X_1$ to $X_4$ in Chemical Formula 1 may be nitrogen atom and the rest of $X_1$ to $X_4$ may be $CR_4$. In an alternative embodiment, $Y_1$ in Chemical Formula 1 may be nitrogen atom or an unsubstituted carbon atom and each of $Y_2$ to $Y_5$ may independently be an unsubstituted or substituted carbon atom. As an example, an organic compound having the benzo-naphthyridine moiety may have the following structure of Chemical Formula 2:

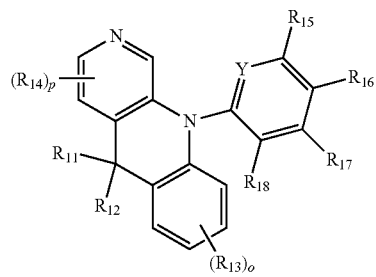

Chemical Formula 2

In Chemical Formula 2, each of $R_{11}$ and $R_{12}$ is independently linear or branched $C_1$-$C_{20}$ alkyl group or $C_6$-$C_{20}$ aryl group. Each of $R_{13}$ and $R_{14}$ is independently protium, deuterium, tritium or linear or branched $C_1$-$C_{20}$ alkyl group. o is id identical as defined in Chemical Formula 1. p is an integer of 1 to 3. Each or $R_{15}$ to $R_{18}$ is independently protium, deuterium, tritium, linear or branched $C_1$-$C_{20}$ alkyl group or $C_{10}$-$C_{30}$ fused hetero aryl group having at least one nitrogen atom (N) on a ring, wherein the $C_{10}$-$C_{30}$ fused hetero aryl group is unsubstituted or substituted a group selected from the group consisting of linear or branched $C_1$-$C_{20}$ alkyl group, $C_6$-$C_{30}$ aryl group, $C_4$-$C_{30}$ hetero aryl group, $C_4$-$C_{30}$ aromatic or hetero aromatic amino group and combination thereof, wherein at least one of $R_{15}$ to $R_{18}$ is $C_{10}$-$C_{30}$ fused hetero aryl group having at least one nitrogen atom (N) on the ring, wherein the $C_{10}$-$C_{30}$ fused hetero aryl group is unsubstituted or substituted a group selected from the group consisting of linear or branched $C_1$-$C_{20}$ alkyl group, $C_6$-$C_{30}$ aryl group, $C_4$-$C_{30}$ hetero aryl group, $C_4$-$C_{30}$ aromatic or hetero aromatic amino group and combination thereof. Y is nitrogen atom (N) or $CR_{19}$, wherein $R_{19}$ is protium, deuterium, tritium or linear or branched $C_1$-$C_{20}$ alkyl group.

Particularly, the organic compound having the structure of Chemical Formula 1 or 2 may include any one having the following structure of Chemical Formula 3.

Chemical Formula 3

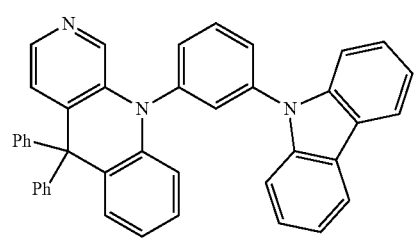

Compound 1

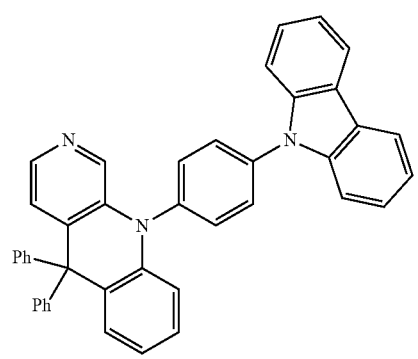

Compound 2

Compound 3
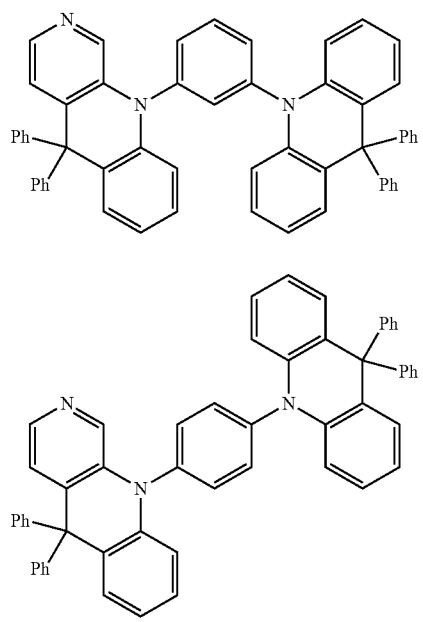
Compound 4
Compound 5
Compound 6
Compound 7
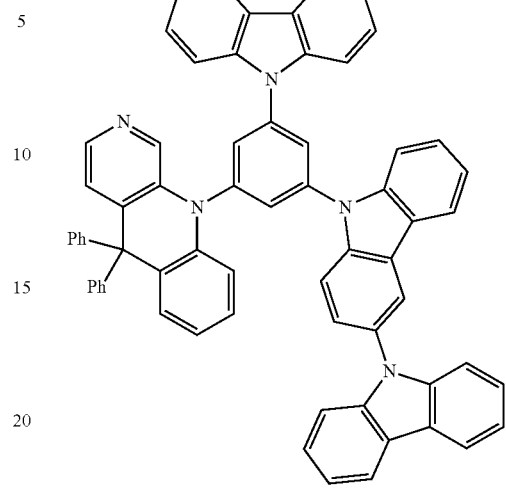
Compound 8
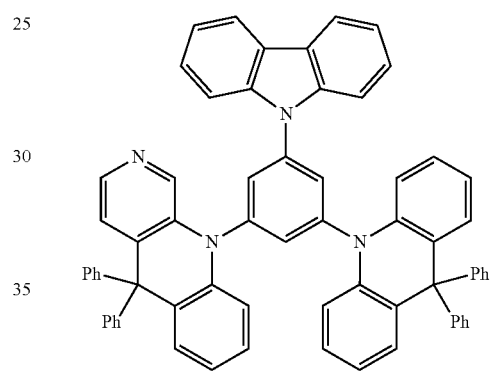
Compound 9
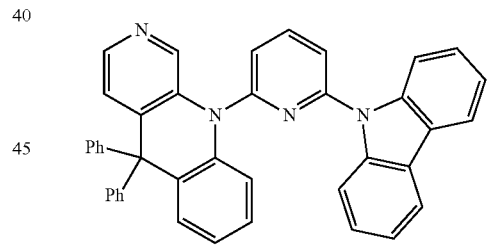
Compound 10
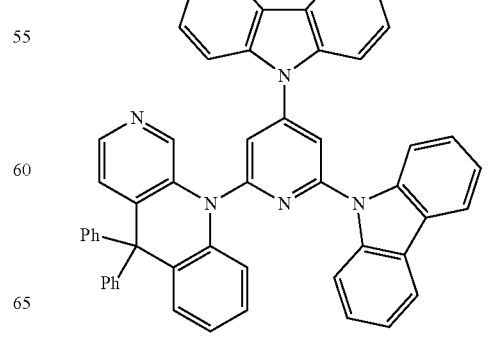

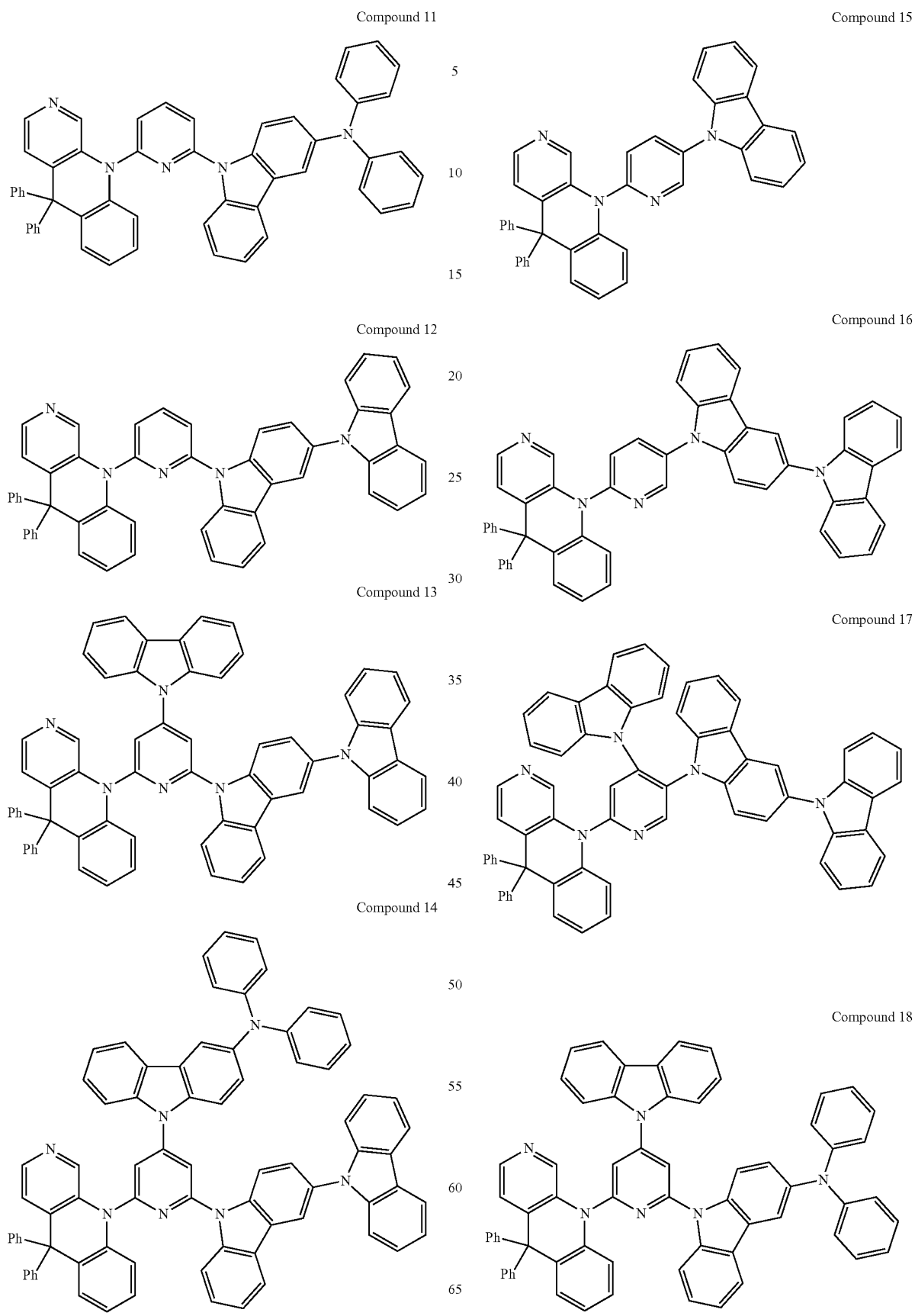

Compound 19
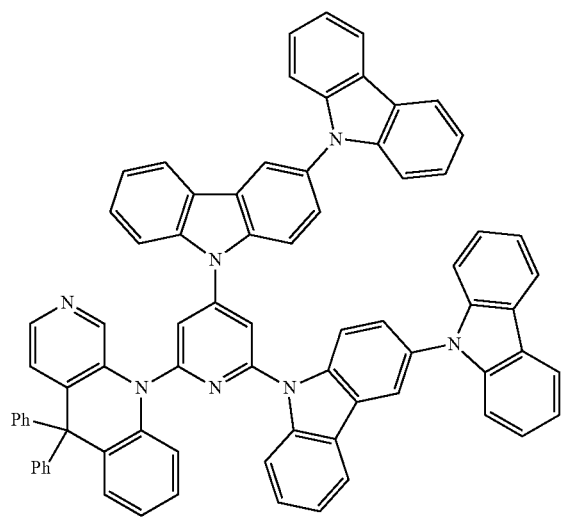
Compound 20
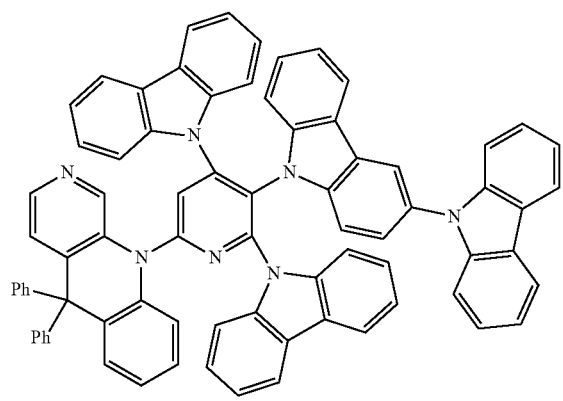
Compound 21
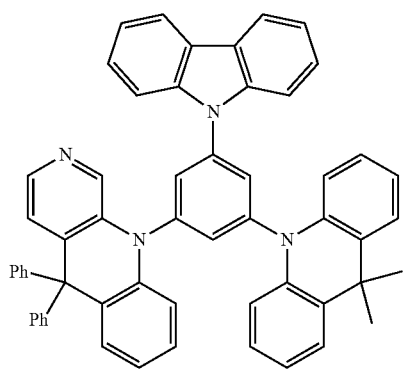
Compound 22
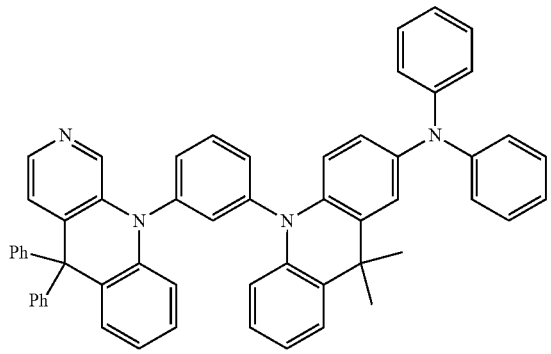
Compound 23
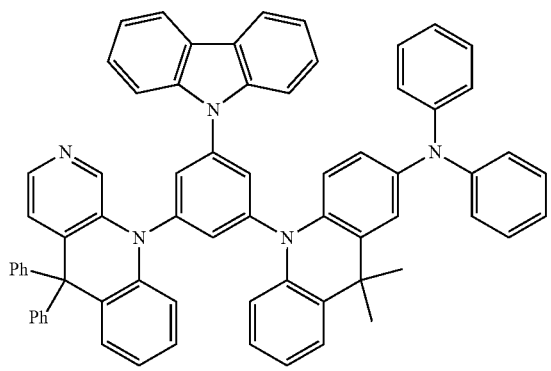
Compound 24
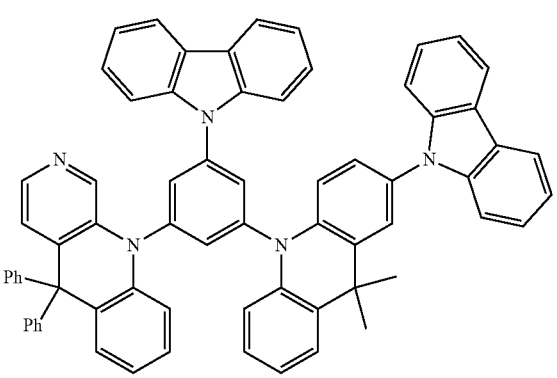

Compound 25
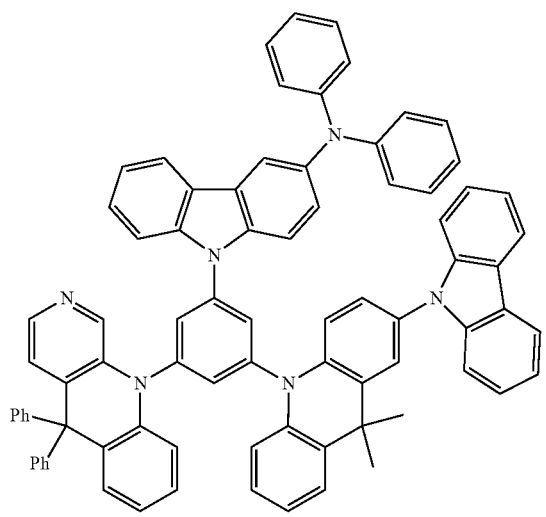
Compound 26
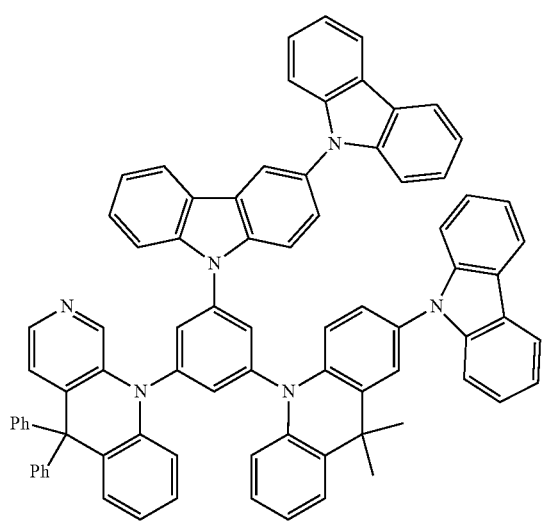
Compound 27
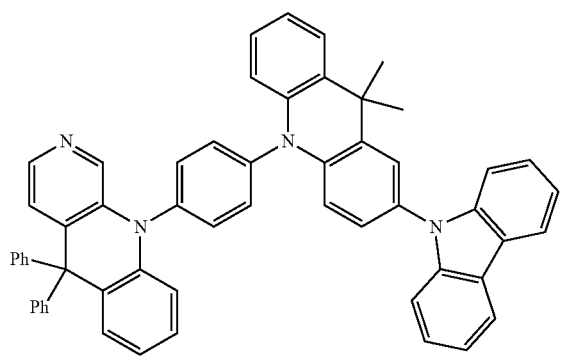
Compound 28
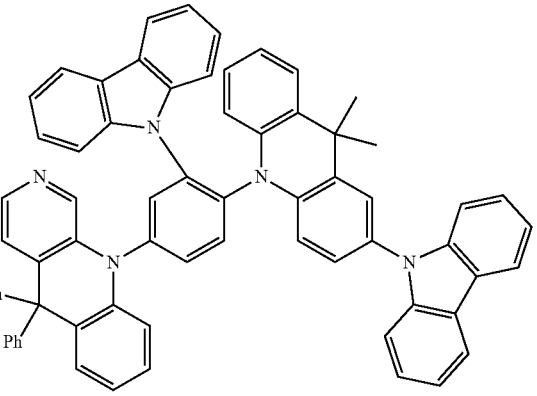
Compound 29
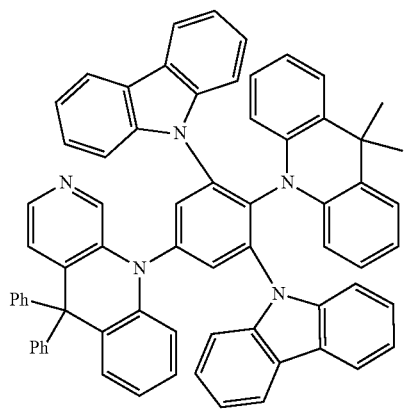
Compound 30
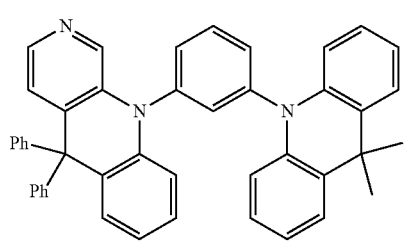
Compound 31
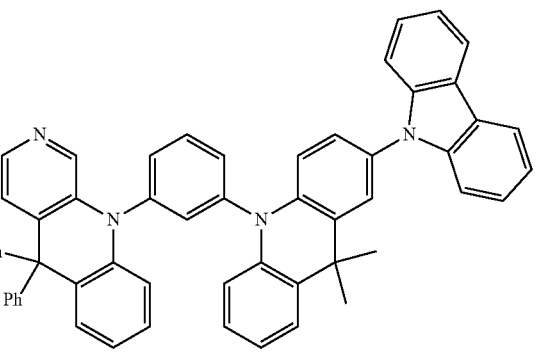

Compound 32
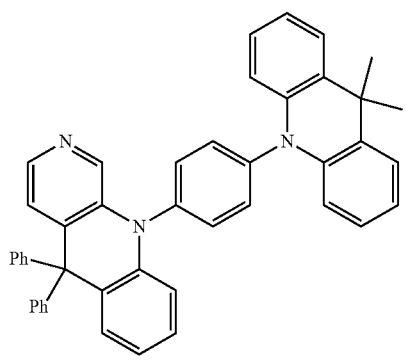
Compound 36
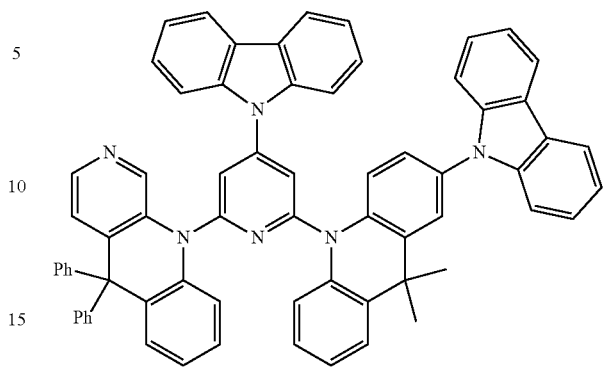
Compound 33
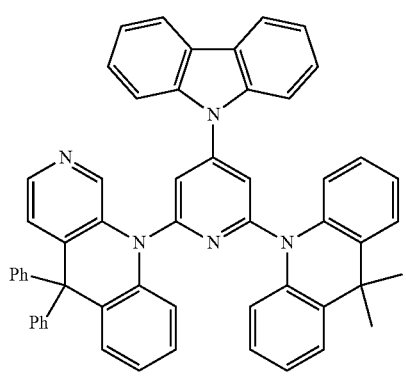
Compound 37
Compound 34
Compound 38
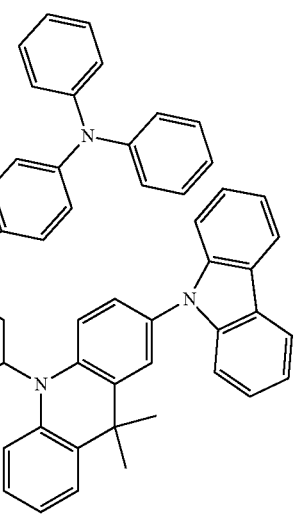
Compound 35
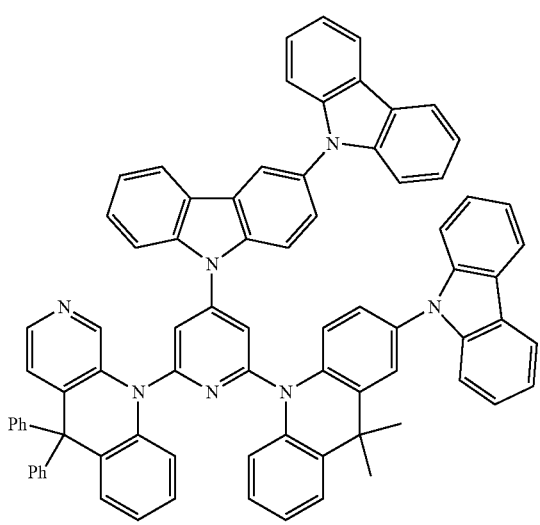

Compound 39
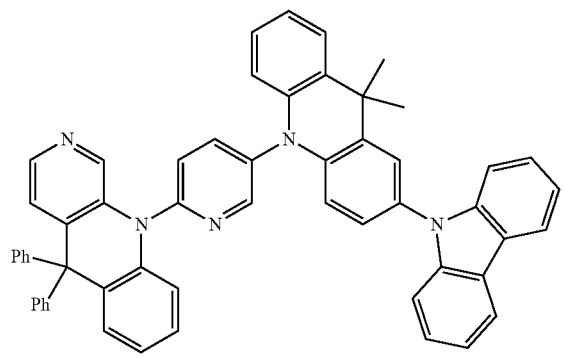
Compound 40
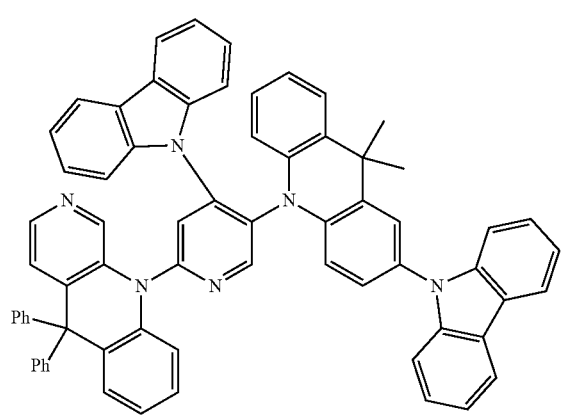
Compound 41
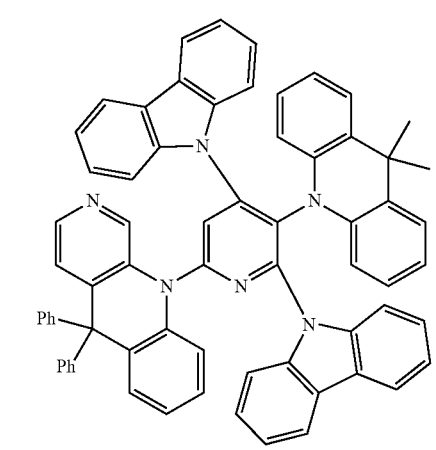
Compound 42
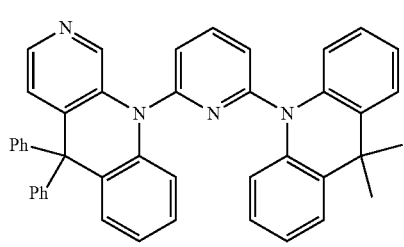
Compound 43
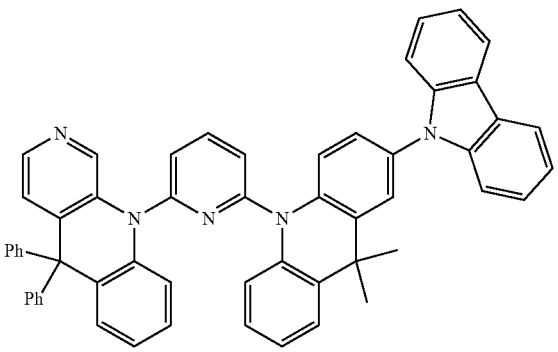
Compound 44
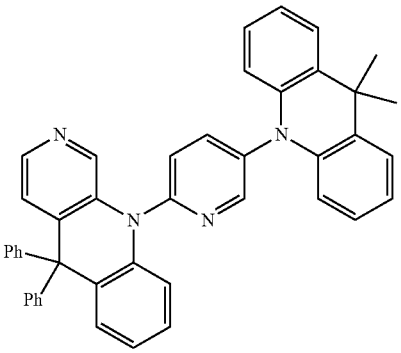
Compound 45
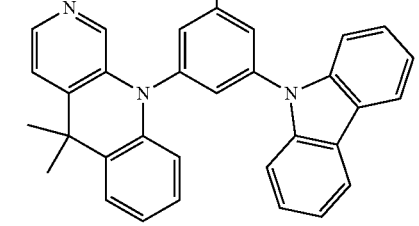
Compound 46
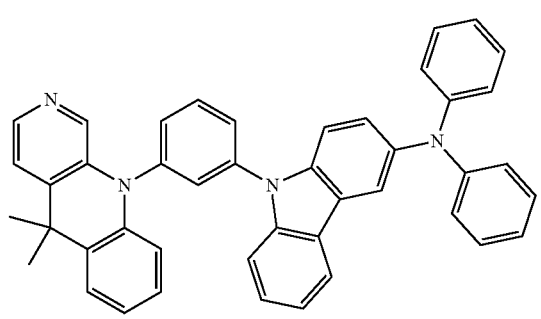

Compound 47
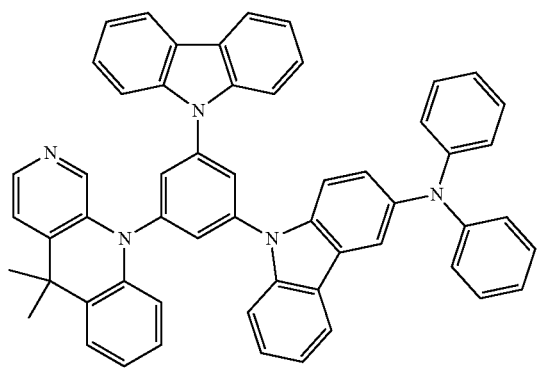
Compound 48
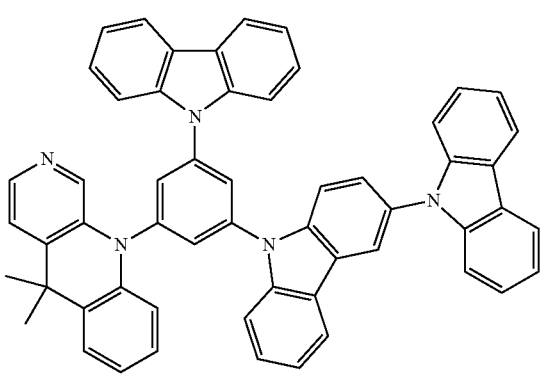
Compound 49
Compound 50
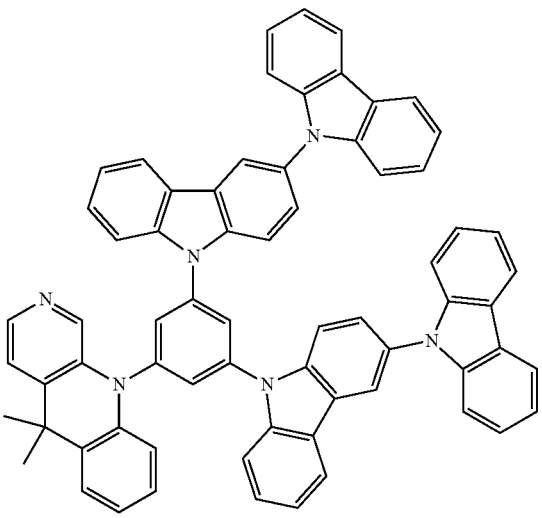
Compound 51
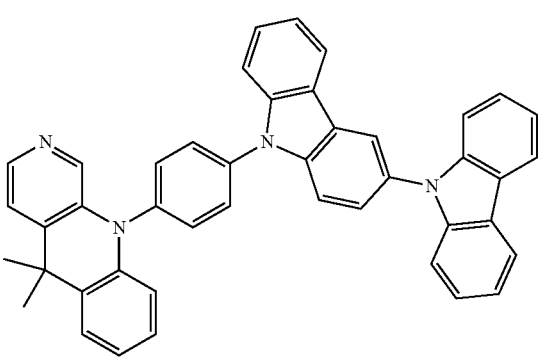
Compound 52
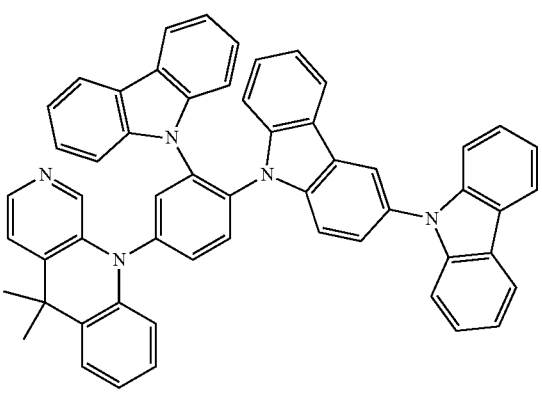

Compound 53
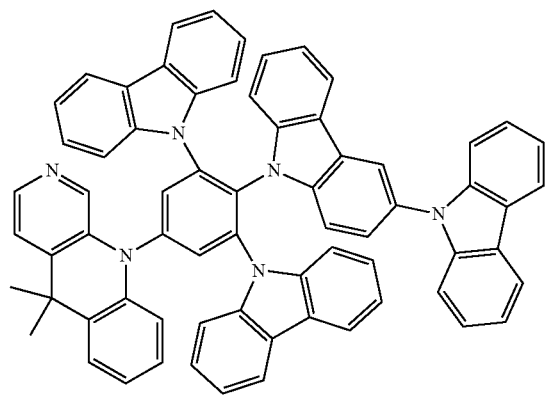
Compound 54
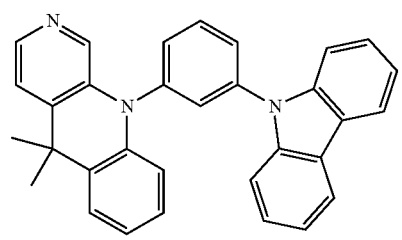
Compound 55
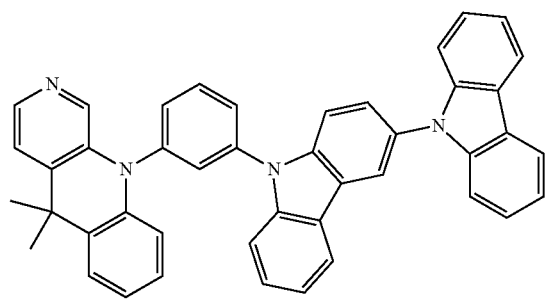
Compound 56
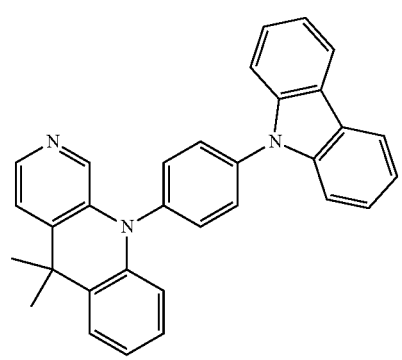
Compound 57
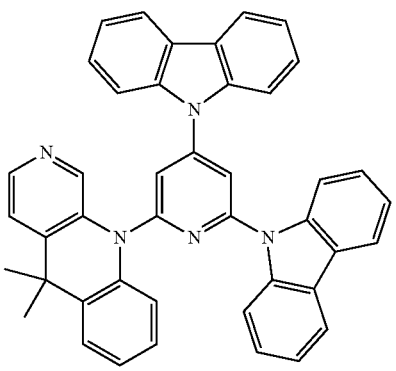
Compound 58
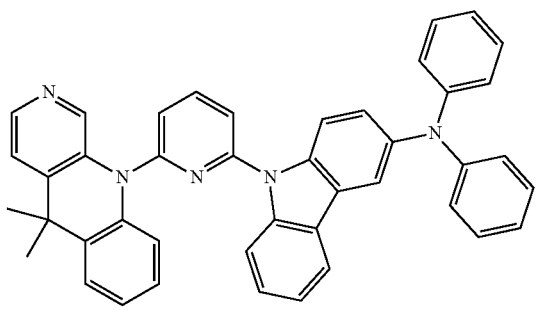
Compound 59
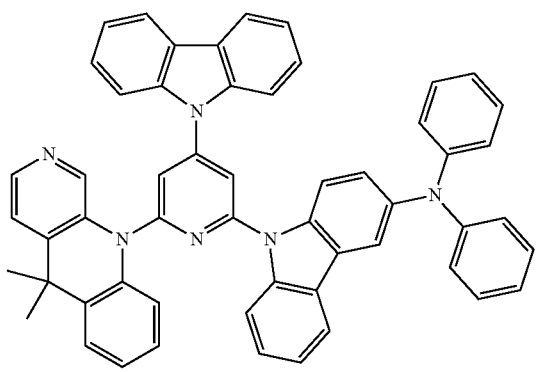
Compound 60
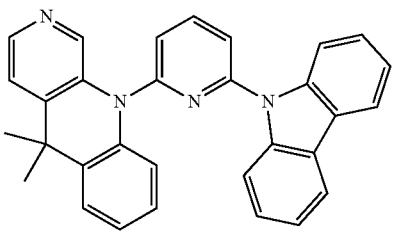

Compound 61
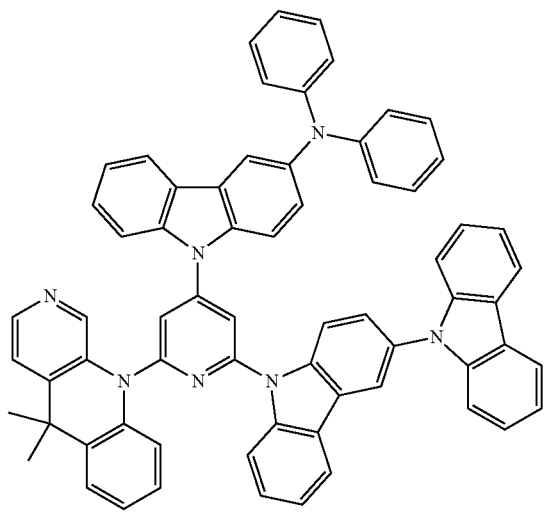
Compound 62
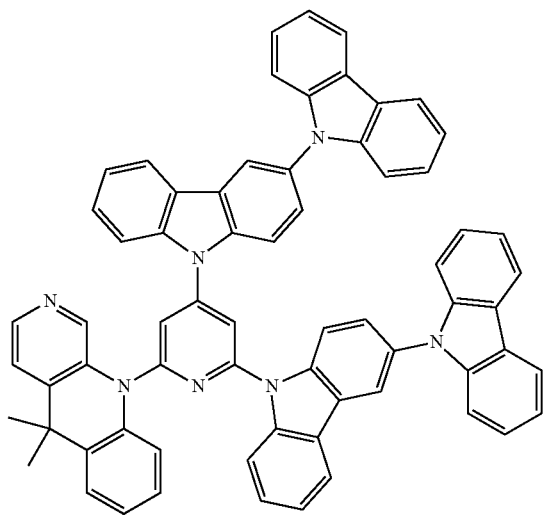
Compound 63
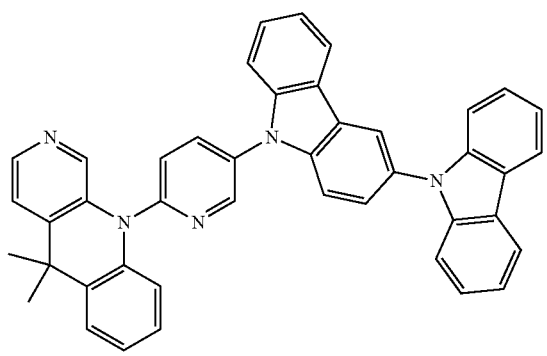
Compound 64
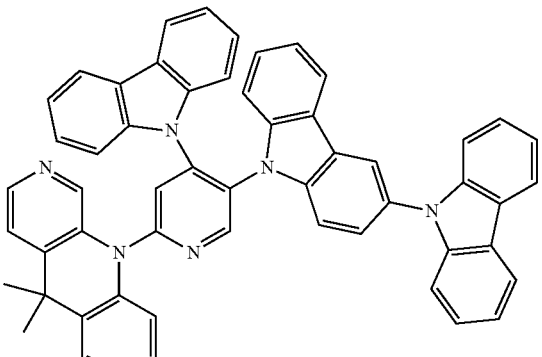
Compound 65
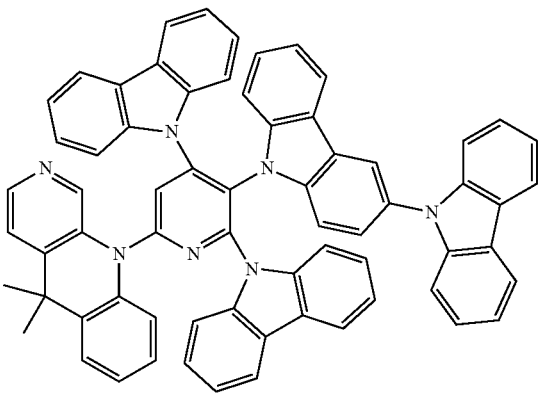
Compound 66
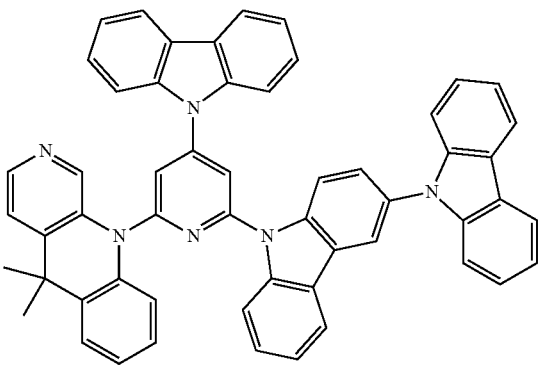
Compound 67
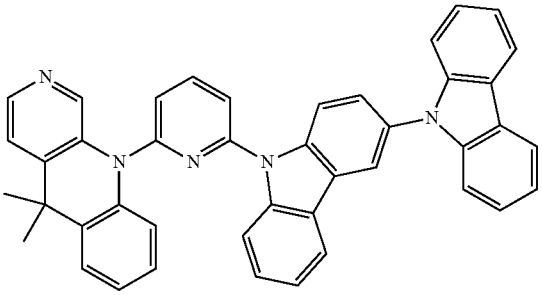

Compound 68
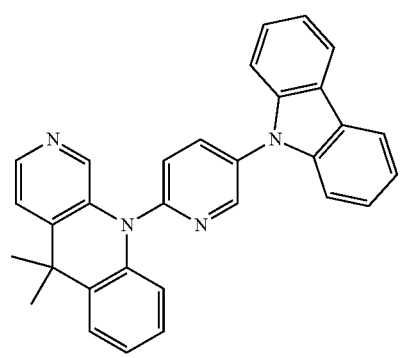
Compound 69
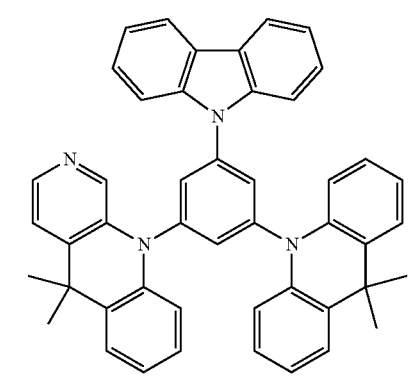
Compound 70
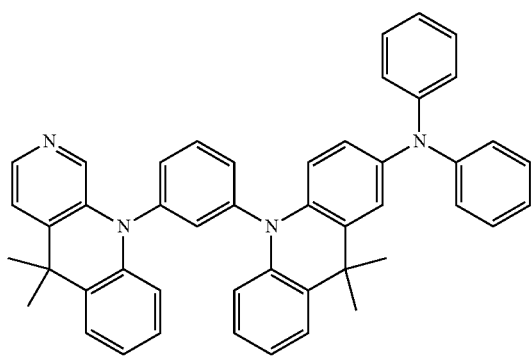
Compound 71
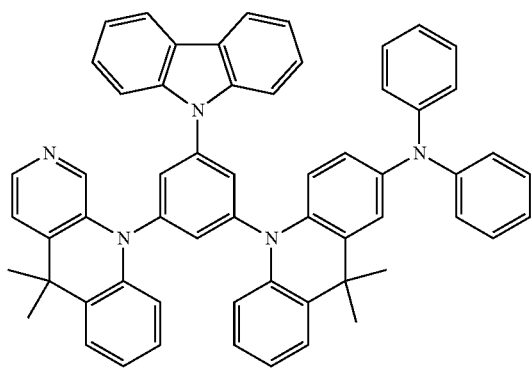
Compound 72
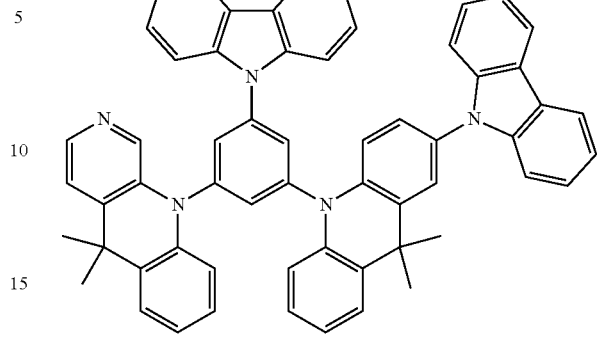
Compound 73
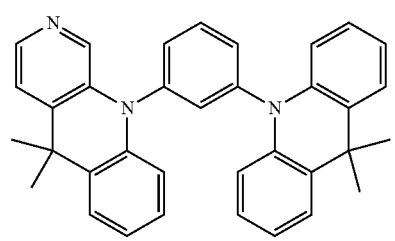
Compound 74
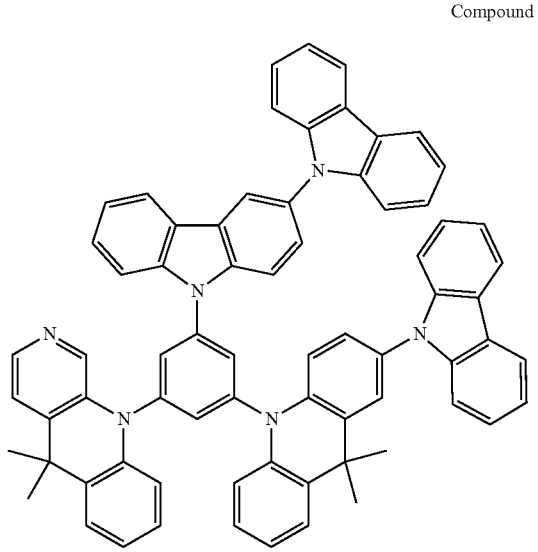
Compound 75
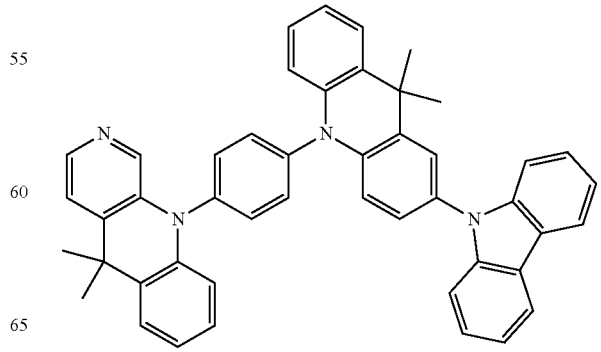

Compound 76

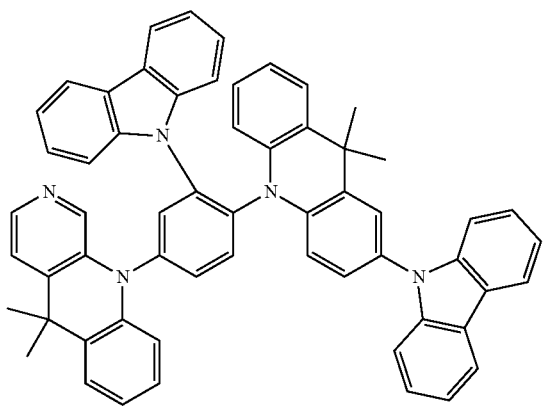

Compound 77

Compound 78

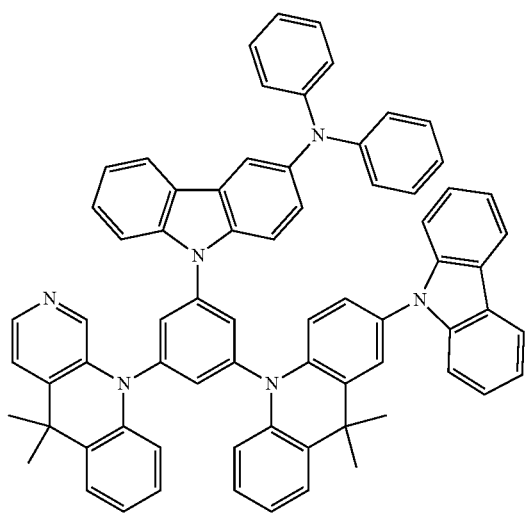

Compound 79

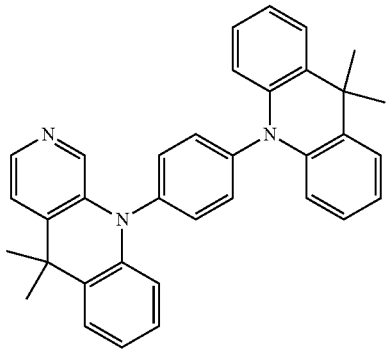

Compound 80

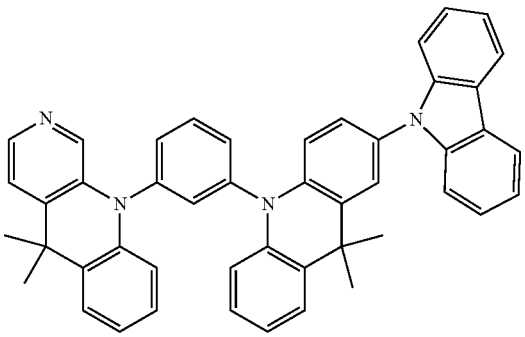

The organic compound having the structure of any one in Chemical Formulae 1 to 3 includes the fused hetero aryl moiety, which has the p-type property, and the aza-acridine moiety, which has the n-type property, linked by an aromatic linker. The organic compound having the structure of any one in Chemical Formulae 1 to 3 has excellent thermal resistance property, high excited state singlet and triplet energy levels and wide energy level bandgap (Eg) between the HOMO energy level and the LUMO energy level. As an example, when the organic compound is used together with a delayed fluorescent material and optionally a fluorescent material in the EML, it is possible to transfer exciton energy to the fluorescent material without energy loss during the emission process.

In other words, the organic compound having the structure of any one in Chemical Formulae 1 to 3 can be used as the host in the EML of the OLED to enhance luminous efficiency. It is possible to minimize exciton quenching owing to an interaction between the exciton in the host and a peripheral polaron and to prevent the luminous lifetime of the OLED being lowered due to electro-oxidation and photo-oxidation. When the organic compound having the structure of any one in Chemical Formulae 1 to 3 is used as the host in the EML, the organic compound can transfer efficiently exciton energy to the fluorescent material so that the OLED may have enhanced luminous efficiency. In addition, since the organic compound in the EML is not deteriorated by heat, the OLED having a long luminous lifetime and excellent color purity can be realized.

[Organic Light Emitting Diode and Device]

The organic compound having the structure of any one in Chemical Formulae 1 to 6 has enhanced thermal resistance property and luminous property. The organic compound having the structure of any one in Chemical Formulae 1 to 6 may be applied to an emitting material layer of an organic light emitting diode so as to implement high color purity and enhance luminous efficiency of the diode. The organic light emitting diode of the present disclosure may be applied to an organic light emitting device such as an organic light emitting display device and an organic light emitting illumination device. An organic light emitting display device will be explained. FIG. 1 is a schematic cross-sectional view of an organic light emitting display device in accordance with an exemplary embodiment of the present disclosure.

As illustrated in FIG. 1, the organic light emitting display device 100 includes a substrate 102, a thin-film transistor Tr on the substrate 102, and an organic light emitting diode 200 connected to the thin film transistor Tr.

The substrate 102 may include, but are not limited to, glass, thin flexible material and/or polymer plastics. For example, the flexible material may be selected from the group, but are not limited to, polyimide (PI), polyethersulfone (PES), polyethylenenaphthalate (PEN), polyethylene terephthalate (PET), polycarbonate (PC) and combination thereof. The substrate 102, over which the thin film transistor Tr and the organic light emitting diode 200 are arranged, form an array substrate.

A buffer layer 104 may be disposed over the substrate 102, and the thin film transistor Tr is disposed over the buffer layer 104. The buffer layer 104 may be omitted.

A semiconductor layer 110 is disposed over the buffer layer 104. In one exemplary embodiment, the semiconductor layer 110 may include, but are not limited to, oxide semiconductor materials. In this case, a light-shield pattern may be disposed under the semiconductor layer 110, and the light-shield pattern can prevent light from being incident toward the semiconductor layer 110, and thereby, preventing the semiconductor layer 110 from being deteriorated by the light. Alternatively, the semiconductor layer 110 may include, but are not limited to, polycrystalline silicon. In this case, opposite edges of the semiconductor layer 110 may be doped with impurities.

A gate insulating layer 120 formed of an insulating material is disposed on the semiconductor layer 110. The gate insulating layer 120 may include, but are not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 may be patterned identically as the gate electrode 130.

An interlayer insulating layer 140 formed of an insulating material is disposed on the gate electrode 130 with covering over an entire surface of the substrate 102. The interlayer insulating layer 140 may include, but are not limited to, an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over opposite sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, each of which is made of a conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

Although not shown in FIG. 1, a gate line and a data line, which cross each other to define a pixel region, and a switching element, which is connected to the gate line and the data line is, may be further formed in the pixel region. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter for absorbing a part of the light emitted from the organic light emitting diode 200. For example, the color filter may absorb a light of specific wavelength such as red (R), green (G) or blue (B). In this case, the organic light emitting display device 100 can implement full-color through the color filter.

For example, when the organic light emitting display device 100 is a bottom-emission type, the color filter may be disposed on the interlayer insulating layer 140 with corresponding to the organic light emitting diode 200. Alternatively, when the organic light emitting display device 100 is a top-emission type, the color filter may be disposed over the organic light emitting diode 200, that is, a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 154, it may be spaced apart from the second semiconductor layer contact hole 154.

The organic light emitting diode 200 includes a first electrode 210 that is disposed on the passivation layer 160 and connected to the drain electrode 154 of the thin film transistor Tr. The organic light emitting diode 200 further includes an emitting unit 230 as an emission layer and a second electrode 220 each of which is disposed sequentially on the first electrode 210.

The first electrode 210 is disposed in each pixel region. The first electrode 210 may be an anode and include a conductive material having a relatively high work function value. For example, the first electrode 210 may include, but are not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the likes.

In one exemplary embodiment, when the organic light emitting display device 100 is a top-emission type, a reflective electrode or a reflective layer may be disposed under the first electrode 210. For example, the reflective electrode or the reflective layer may include, but are not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

An emitting unit 230 is disposed on the first electrode 210. In one exemplary embodiment, the emitting unit 230 may have a mono-layered structure of an emitting material layer. Alternatively, the emitting unit 230 may have a multiple-layered structure of a hole injection layer, a hole transport layer, an electron blocking layer, an emitting material layer, a hole blocking layer, an electron transport layer and/or an electron injection layer (See, FIGS. 2, 5, 7, 9 and 11). In one embodiment, the organic light emitting diode 200 may have one emitting unit 230. Alternatively, the organic light emitting diode 200 may have multiple emitting units 230 to form a tandem structure. The emitting unit 230 includes an organic compound having the structure of any one in Chemical Formulae 1 to 6. As an example, the organic compound having the structure of any one in Chemical Formulae 1 to 6 may be used a host of an emitting material layer which may further includes at least one dopant.

The second electrode 220 is disposed over the substrate 102 above which the emitting unit 230 is disposed. The second electrode 220 may be disposed over a whole display area and may include a conductive material with a relatively low work function value compared to the first electrode 210. The second electrode 220 may be a cathode. For example, the second electrode 220 may include, but are not limited to, aluminum (Al), magnesium (Mg), calcium (Ca), silver (Ag), alloy thereof or combination thereof such as aluminum-magnesium alloy (Al—Mg).

In addition, an encapsulation film 180 may be disposed over the second electrode 220 in order to prevent outer moisture from penetrating into the organic light emitting diode 200. The encapsulation film 180 may have, but are not limited to, a laminated structure of a first inorganic insulating film 182, an organic insulating film 184 and a second inorganic insulating film 186.

The emitting unit 230 of the OLED 200 includes the organic compound having the structure of any one in Chemical Formulae 1 to 6, as described above. Since the organic compound has excellent thermal resistant property and luminous property, the OLED 200 can enhance its luminous efficiency and luminous lifetime and lower its driving voltage so as to reduce its consumption power by applying the organic compound having the structure of any one in Chemical Formulae 1 to 6 into the emitting unit 230.

Figure 2:
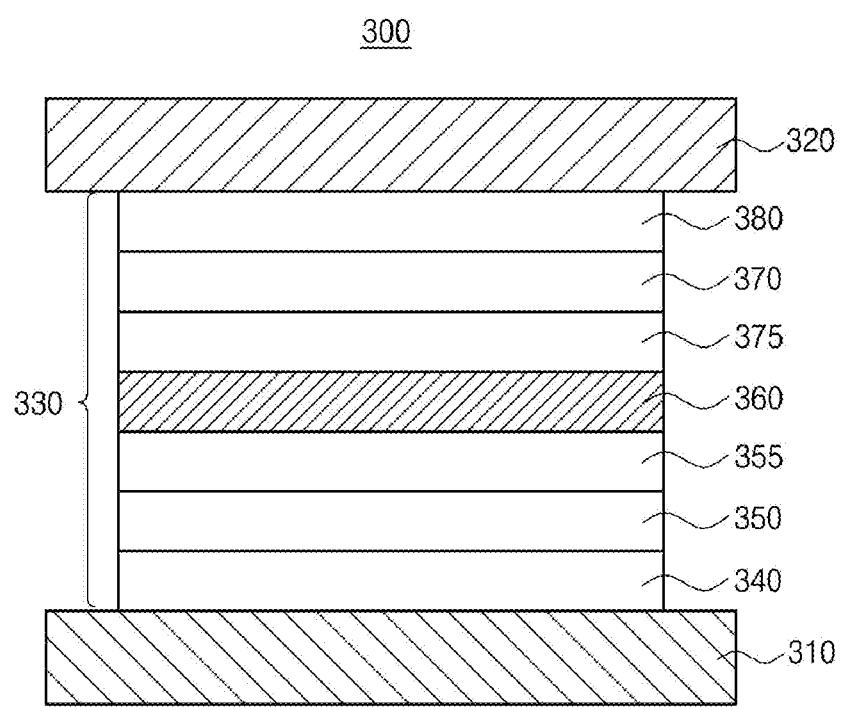
FIG. 2 is a schematic cross-sectional view illustrating an organic light emitting diode in accordance with an exemplary embodiment of the present disclosure.

FIG. 2 is a schematic cross-sectional view illustrating an organic light emitting diode having a single-layered EML in accordance with an exemplary embodiment of the present disclosure. As illustrated in FIG. 2, the organic light emitting diode (OLED) 300 in accordance with the first embodiment of the present disclosure includes first and second electrodes 310 and 320 facing each other, an emitting unit 330 as an emission layer disposed between the first and second electrodes 310 and 320. In one exemplary embodiment, the emitting unit 330 includes a hole injection layer (HIL) 340, a hole transport layer (HTL) 350, an emitting material layer (EML) 360, an electron transport layer (ETL) 370 and an electron injection layer (EIL) 380 each of which is laminated sequentially from the first electrode 310. Alternatively, the emitting unit 330 may further include a first exciton blocking layer, i.e. an electron blocking layer (EBL) 355 disposed between the HTL 350 and the EML 360 and/or a second exciton blocking layer, i.e. a hole blocking layer (HBL) 375 disposed between the EML 360 and the ETL 370.

The first electrode 310 may be an anode that provides a hole into the EML 360. The first electrode 310 may include, but are not limited to, a conductive material having a relatively high work function value, for example, a transparent conductive oxide (TCO). In an exemplary embodiment, the first electrode 310 may include, but are not limited to, ITO, IZO, ITZO, SnO, ZnO, ICO, AZO, and the likes.

The second electrode 320 may be a cathode that provides an electron into the EML 360. The second electrode 320 may include, but are not limited to, a conductive material having a relatively low work function values, i.e., a highly reflective material such as Al, Mg, Ca, Ag, alloy thereof, combination thereof, and the likes.

The HIL 340 is disposed between the first electrode 310 and the HTL 350 and improves an interface property between the inorganic first electrode 310 and the organic HTL 350. In one exemplary embodiment, the HIL 340 may include, but are not limited to, 4,4',4''-Tris(3-methylphenylamino)triphenylamine (MTDATA), 4,4',4''-Tris(N,N-diphenyl-amino)triphenylamine (NATA), 4,4',4''-Tris(N-(naphthalene-1-yl)-N-phenyl-amino)triphenylamine (1T-NATA), 4,4',4''-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4''-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiphene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 340 may be omitted in compliance with a structure of the OLED 300.

The HTL 350 is disposed adjacently to the EML 360 between the first electrode 310 and the EML 360. In one exemplary embodiment, the HTL 350 may include, but are not limited to, N,N'-Diphenyl-N,N'-bis(3-methylphenyl)-1, 1'-biphenyl-4,4'-diamine (TPD), NPB, 4,4'-bis(N-carbazolyl)-1,1'-biphenyl (CBP), Poly[N,N'-bis(4-butylpnehyl)-N,N'-bis(phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In one exemplary embodiment, each of the HIL 340 and the HTL 350 may be laminated with a thickness of, but are not limited to, about 5 to about 200 nm, and preferably about 5 to about 100 nm.

The EML 360 may include a host doped with a dopant. In this exemplary embodiment, the EML 360 may include a host (a first host) doped with a dopant (a first dopant). For example, the organic compound having the structure of any one in Chemical Formulae 1 to 6 may be used as the host in the EML 360. The EML 360 may emit light of red color, green color or blue color. The configuration and energy levels among the luminous materials will be explained in more detail.

The ETL 370 and the EIL 380 are laminated sequentially between the EML 360 and the second electrode 320. The ETL 370 may include a material having high electron mobility so as to provide electrons stably with the EML 360 by fast electron transportation.

In one exemplary embodiment, the ETL 370 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes.

As an example, the ETL 370 may include, but are not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenyl-benzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl) 1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)](PFNBr) and/or tris(phenylquinoxaline) (TPQ).

The EIL 380 is disposed between the second electrode 320 and the ETL 370, and can improve physical properties of the second electrode 320 and therefore, can enhance the life span of the OLED 300. In one exemplary embodiment, the EIL 380 may include, but are not limited to, an alkali halide and/or an alkali earth halide such as LiF, CsF, NaF, $BaF_2$ and the likes, and/or an organic metal compound such as lithium benzoate, sodium stearate, and the likes.

As an example, each of the ETL 370 and the EIL 380 may be laminated with a thickness of, but are not limited to, about 10 to about 100 nm.

When holes are transferred to the second electrode 320 via the EML 360 and/or electrons are transferred to the first electrode 310 via the EML 360, the luminous lifetime and the luminous efficiency of the OLED 300 may be reduced. In order to prevent those phenomena, the OLED 300 in accordance with this embodiment of the present disclosure has at least one exciton blocking layer disposed adjacently to the EML 360.

For example, the OLED 300 of the exemplary embodiment includes the EBL 355 between the HTL 350 and the EML 360 so that electrons cannot be transferred from the EML 360 to the HTL 350. In one exemplary embodiment, the EBL 355 may include, but are not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-bis(carbazol-9-yl) benzene (mCP), 3,3'-bis(N-carbazolyl)-1,1'-biphenyl (mCBP), CuPc, N,N'-bis[4-(bis(3-methylphenyl)amino) phenyl]-N,N'-diphenyl-[1,1'-biphenyl]-4,4'-diamine (DNTPD), TDAPB, 2,8-bis(9-phenyl-9H-carbazol-3-yl) dibenzo[b,d]thiophene, and/or 3,6-bis(N-carbazolyl)-N-phenyl-carbazole.

In addition, the OLED 300 further includes the HBL 375 as a second exciton blocking layer between the EML 360 and the ETL 370 so that holes cannot be transferred from the EML 360 to the ETL 370. In one exemplary embodiment, the HBL 375 may include, but are not limited to, oxadiazole-based compounds, triazole-based compounds, phenanthroline-based compounds, benzoxazole-based compounds, benzothiazole-based compounds, benzimidazole-based compounds, and triazine-based compounds.

For example, the HBL 375 may include a compound having a relatively low HOMO energy level compared to the emitting material in EML 360. The HBL 375 may include, but are not limited to, BCP, BAlq, $Alq_3$, PBD, spiro-PBD, Liq, Bis-4,5-(3,5-di-3-pyridylphenyl)-2-methylpyrimidine (B3PYMPM), DPEPO, 9-(6-(9H-carbazol-9-yl)pyridine-3-yl)-9H-3,9'-bicarbazole and combination thereof.

As described schematically above, the EML 360 of the OLED 300 in accordance with the first embodiment of the present disclosure include a host, i.e. the organic compound having the structure of any one in Chemical Formulae 1 to 6, and a dopant having a delayed fluorescent property (T dopant). When the EML 360 includes the dopant having the delayed fluorescent property, the OLED 300 can improve its luminous efficiency and its luminous lifetime and lower its driving voltage.

An Organic Light Emitting Diode (OLED) emits light as holes injected from the anode and electrons injected from the cathode are combined to form excitons in EML and then unstable excited state excitons return to a stable ground state. Theoretically, when electrons meet holes to form exciton, a singlet exciton of a paired spin and a triplet exciton of an unpaired spin are produced by a ratio of 1:3 by spin arrangements. Only the singlet exciton among the excitons can be involved in emission process in case of fluorescent materials. Accordingly, the OLED may exhibit luminous efficiency by maximum 5% in case of using the common fluorescent material.

In contrast, phosphorescent materials use different luminous mechanism of converting both singlet excitons and triplet exciton into light. The phosphorescent materials can convert singlet excitons into triplet excitons through inter-system crossing (ISC). Therefore, it is possible to enhance luminous efficiency in case of applying the phosphorescent materials that use both the singlet excitons and the triplet excitons during the luminous process compared to the fluorescent materials. However, prior art blue phosphorescent materials exhibit too low color purity to apply with the display device and exhibit very short luminous lifetime, and therefore, they have not been used in commercial display devices.

A delayed fluorescent material, which can solve the limitations accompanied by the prior art fluorescent dopants and the phosphorescent dopants, has been developed recently. Representative delayed fluorescent material is a thermally-activated delayed fluorescent (TADF) material. Since the delayed fluorescent material generally has both an electron donor moiety and an electron acceptor moiety within its molecular structure, it can be converted to an intramolecular charge transfer (ICT) state. In case of using the delayed fluorescent material as a dopant, it is possible to use both the excitons of singlet energy level $S_1$ and the excitons of triplet energy level $T_1$ during the emission process.

Figure 3:
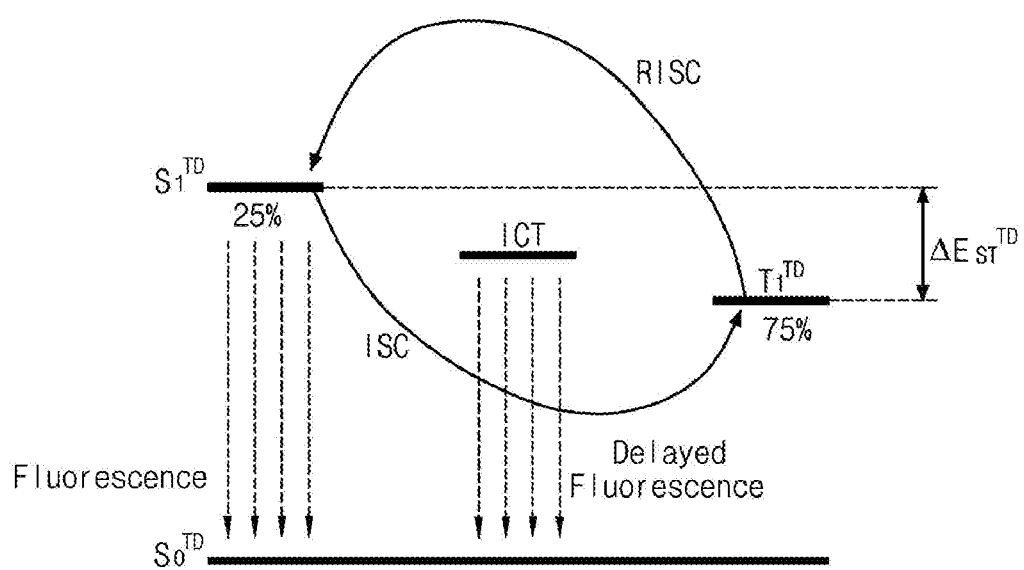
FIG. 3 is s schematic diagram illustrating luminous mechanism of the delayed fluorescent material in an EML in accordance with an exemplary embodiment of the present disclosure.

The luminous mechanism of the delayed fluorescent material will be explained with referring to FIG. 3, which is a schematic diagram illustrating a luminous mechanism of the delayed fluorescent material in an EML in accordance with another exemplary embodiment of the present disclosure. As illustrated in FIG. 3, both the excitons of singlet energy level $S_1^{TD}$ and the excitons of triplet energy level $T_1^{TD}$ in the delayed fluorescent material can move to an intermediate energy level state, i.e. ICT state, and then the intermediate stated excitons can be transferred to a ground state ($S_0$; $S_1 \rightarrow ICT \leftarrow T_1$). Since the excitons of singlet energy level $S_1^{TD}$ as well as the excitons of triplet energy level $T_1^{TD}$ in the delayed fluorescent material is involved in the emission process, the delayed fluorescent material can improve luminous efficiency.

Because both the HOMO and the LUMO are widely distributed over the whole molecule within the common fluorescent material, it is not possible to inter-convert between the singlet energy level and the triplet energy level within it (selection rule). In contrast, since the delayed fluorescent material, which can be converted to ICT state, has little orbital overlaps between HOMO and LUMO, there is little interaction between the HOMO state molecular orbital and the LUMO state molecular orbital in the state where dipole moment is polarized within the delayed fluorescent material. As a result, the changes of spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, it exists as a polarized state having a large dipole moment within the molecule. As the interaction between HOMO molecular orbital and LUMO molecular orbital becomes little in the state where the dipole moment is polarized, both the triplet energy level excitons and the singlet energy level excitons can be converted to ICT state. Accordingly, the excitons of triplet energy level $T_1$ as well as the excitons of singlet energy level $S_1$ can be involved in the emission process.

In case of driving the diode that includes the delayed fluorescent material, 25% excitons of singlet energy level $S_1^{TD}$ and 75% excitons of triplet energy level $T_1^{TD}$ are converted to ICT state by heat or electrical field, and then the converted excitons transfer to the ground state $S_0$ with luminescence. Therefore, the delayed fluorescent material may have 100% internal quantum efficiency in theory.

The delayed fluorescent material must have an energy level bandgap $\Delta E_{ST}^{TD}$ equal to or less than about 0.3 eV, for example, from about 0.05 to about 0.3 eV, between the singlet energy level $S_1^{TD}$ and the triplet energy level $T_1^{TD}$ so that exciton energy in both the singlet energy level and the triplet energy level can be transferred to the ICT state. The material having little energy level bandgap between the singlet energy level $S_1^{TD}$ and the triplet energy level $T_1^{TD}$ can exhibit common fluorescence with Inter system Crossing (ISC) in which the excitons of singlet energy level $S_1^{TD}$ can be transferred to the excitons of triplet energy level $T_1^{TD}$, as well as delayed fluorescence with Reverser Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be transferred to the ground state $S_0$.

The delayed fluorescent material can realize identical quantum efficiency as the prior art phosphorescent material including heavy metal because the delayed fluorescent material can obtain luminous efficiency up to 100% in theory. The host for implementing the delayed fluorescence can induce triplet exciton energy generated at the delayed fluorescent material to be involved in the luminous process without quenching as a non-emission. In order to induce such exciton energy transfer, energy levels among the host and the delayed fluorescent material should be adjusted.

Figure 4:
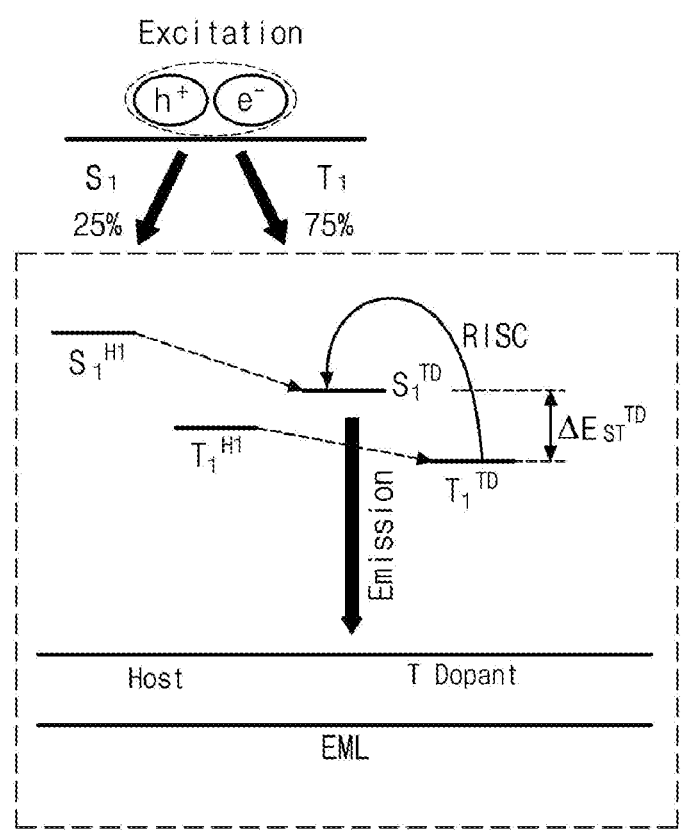
FIG. 4 is a schematic diagram illustrating luminous mechanism by energy level bandgap between luminous materials in accordance with an exemplary embodiment of the present disclosure.

FIG. 4 is a schematic diagram illustrating luminous mechanism by energy level bandgap between luminous materials in accordance with an exemplary embodiment of the present disclosure. As illustrated schematically in FIG. 4, an excited state singlet energy level $S_1^H$ and an excited state triplet energy level $T_1^H$ of the host should be higher than an excited state singlet energy level $S_1^{TD}$ and an excited state triple energy level $T_1^{TD}$ of the dopant having the delayed fluorescent property, respectively. For example, the excited triplet energy level $T_1^H$ of the host may be higher than the excited state triplet energy level $T_1^{TD}$ of the dopant by at least about 0.2 eV.

As an example, when the excited state triplet energy level $T_1^H$ of the host is not higher enough than the excited state triplet energy levels $T_1^{TD}$ of the dopant, which may be a delayed fluorescent material, the excitons of the triplet energy level $T_1^{TD}$ of the dopant can be reversely transferred to the excited state triplet energy level $T_1^H$ of the host, which cannot utilize triplet exciton energy. Accordingly, the excitons of the triplet energy level $T_1^{TD}$ of the dopant having the delayed fluorescent property may be quenched as a non-emission and the triplet state excitons of the dopant cannot be involved in the emission.

The dopant (TD) must have an energy level bandgap $\Delta E_{ST}^{TD}$ between the excited state singlet energy level $S_1^{TD}$ and the excited state triplet energy level $T_1^{TD}$ equal to or less than about 0.3 eV, for example between about 0.05 and about 0.3 eV, in order to realize delayed fluorescence (See, FIG. 3).

In addition, it is necessary to adjust properly HOMO energy levels and LUMO energy levels of the host and the dopant, which may be the fluorescent material. For example, it is preferable that an energy level bandgap ($|HOMO^H - HOMO^{TD}|$) between a HOMO energy level ($HOMO^H$) of the host and a HOMO energy level ($HOMO^{TD}$) of the dopant, or an energy level bandgap ($|LUMO^H - LUMO^{TD}|$) between a LUMO energy level ($LUMO^H$) of the host and a LUMO energy level ($LUMO^{TD}$) of the dopant may be equal to or less than about 0.5 eV, for example, between about 0.1 eV to about 0.5 eV. In this case, the charges can be transported efficiently from the host to the first dopant and thereby enhancing an ultimate luminous efficiency.

Moreover, an energy level bandgap ($Eg^H$) between the HOMO energy level ($HOMO^H$) and the LUMO energy level ($LUMO^H$) of the host may be larger than an energy level bandgap ($Eg^{TD}$) between the HOMO energy level ($HOMO^{TD}$) and the LUMO energy level ($LUMO^{TD}$) of the dopant. As an example, the HOMO energy level ($HOMO^H$) of the host is deeper or lower than the HOMO energy level ($HOMO^{TD}$) of the dopant, and the LUMO energy level ($LUMO^H$) of the host is shallower or higher than the LUMO energy level ($LUMO^{TD}$) of the dopant.

The organic compound having the structure of any one in Chemical Formulae 1 to 6 includes the carbazolyl moiety having p-type property, and the second dibenzofuranyl/dibenzothiophenyl moiety having n-type property, and the carbazolyl moiety and the second dibenzofuranyl/dibenzothiophenyl moiety are linked to the first dibenzofuranyl/dibenzothiophenyl moiety asymmetrically. The organic compound having the structure of any one in Chemical Formulae 1 to 6 may exhibit more amorphous property so as to improve extremely its heat resistance. Accordingly, the crystallization caused by Joule's heat in driving the OLED is prevented, and the structure of the OLED is not destroyed. Moreover, because the organic compound having the structure of any one in Chemical Formulae 1 to 6 includes the carbazolyl moiety and dibenzofuranyl/dibenzothiophenyl moieties, each of which includes two benzene rings, the organic compound has a HOMO energy level and a LUMO energy level proper for use as the host in the EML 360. Particularly, when the organic compound is used together with a delayed fluorescent material and optionally a fluorescent material in the EML, it is possible to transfer exciton energy to the fluorescent material without energy loss during the emission process.

In other words, when the organic compound having the structure of any one in Chemical Formulae 1 to 6 is used as the host in the EML 360 of the OLED 300, it is possible to minimize exciton quenching owing to an interaction between the exciton in the host and a peripheral polaron and to prevent the luminous lifetime of the OLED being lowered due to electro-oxidation and photo-oxidation. Also, the organic compound has excellent thermal resistance property and high triplet energy level and large energy level bandgap between the HOMO energy level and the LUMO energy level. When the organic compound having the structure of any one in Chemical Formulae 1 to 6 is used as the host in the EML 360, the OLED 300 can enhance its luminous efficiency due to efficient exciton energy transfer from the host to the dopant. In addition, the OLED 300 can realize high color purity and long luminous lifetime as the damage to the luminous materials in the EML 360 is reduced.

In one exemplary embodiment, when the organic compound having the structure of any one in Chemical Formulae 1 to 6 is used as the host in the EML 360, a delayed fluorescent material having proper energy levels compared to the host may be used as the dopant in the EML 360. For example, the dopant may emit light of red color, green color or blue color. As an example, the dopant may have an excited state singlet energy level ($S_1^{TD}$), but are not limited to, between about 2.7 eV and about 2.75 eV and an excited state triplet energy level ($T_1^{TD}$), but are not limited to, between about 2.4 eV and about 2.5 eV in order to implement luminescence level applicable to a display device.

Delayed fluorescent materials, which can be used as the dopant, may have the HOMO energy level ($HOMO^{TD}$), but are not limited to, between about −5.0 eV and about −6.0 eV, and preferably between about −5.0 eV and about −5.5 eV, the LUMO energy level ($LUMO^{TD}$), but are not limited to, between about −2.5 eV and about −3.5 eV, and preferably between about −2.5 eV and about −3.0 eV, and the energy level bandgap ($Eg^{TD}$) between those HOMO and LUMO energy levels ($HOMO^{TD}$ and $LUMO^{TD}$) may be, but are not limited to, between about 2.2 eV and about 3.0 eV, and preferably between about 2.4 eV and about 2.8 eV. The organic compound having the structure of any one in Chemical Formulae 1 to 6 may have the HOMO energy level ($HOMO^H$), but are not limited to, between about −5.0 eV and about −6.5 eV, and preferably between about −5.5 eV and about −6.2 eV, the LUMO energy level ($LUMO^H$), but are not limited to, between about −1.5 eV and about −3.0 eV, and preferably between about −1.5 eV and about −2.5 eV, and the energy level bandgap ($Eg^H$) between those HOMO and LUMO energy levels ($HOMO^H$ and $LUMO^H$) may be, but are not limited to, between about 3.0 eV and about 4.0 eV, and preferably between about 3.0 eV and about 3.5 eV.

In one exemplary embodiment, a delayed fluorescent material that can be used as the dopant in the EML 360 may include any one having the following structure of Chemical 7.

Chemical Formula 7

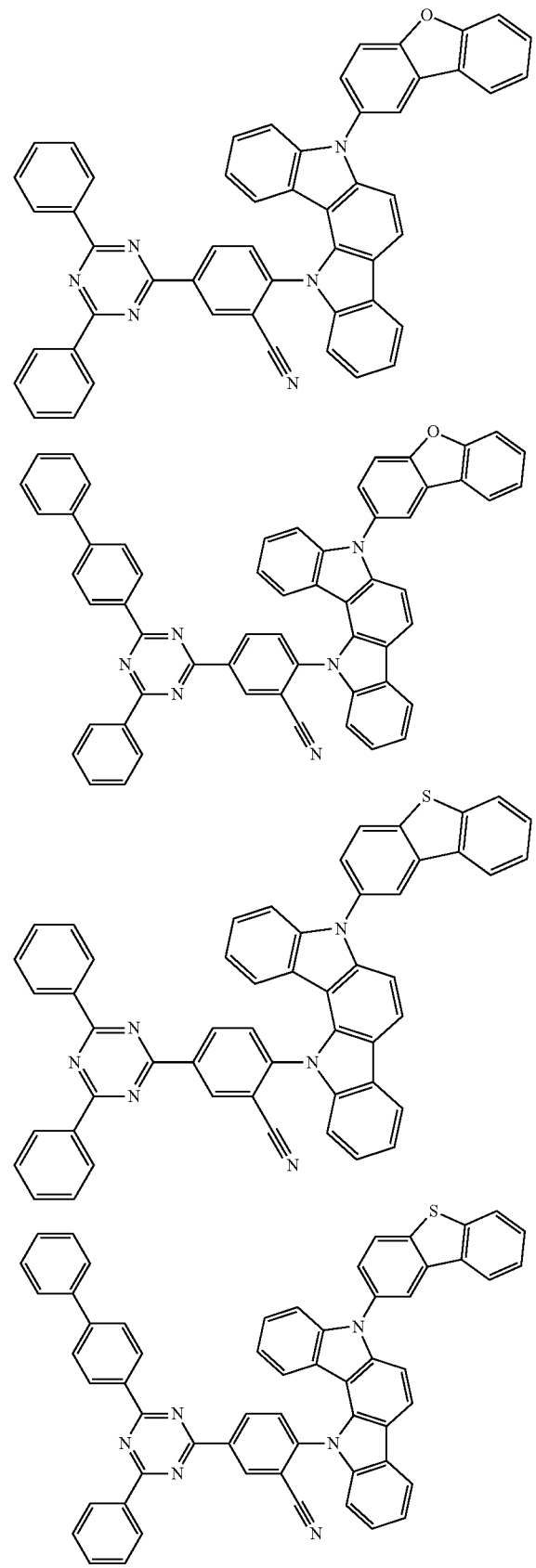

41
-continued
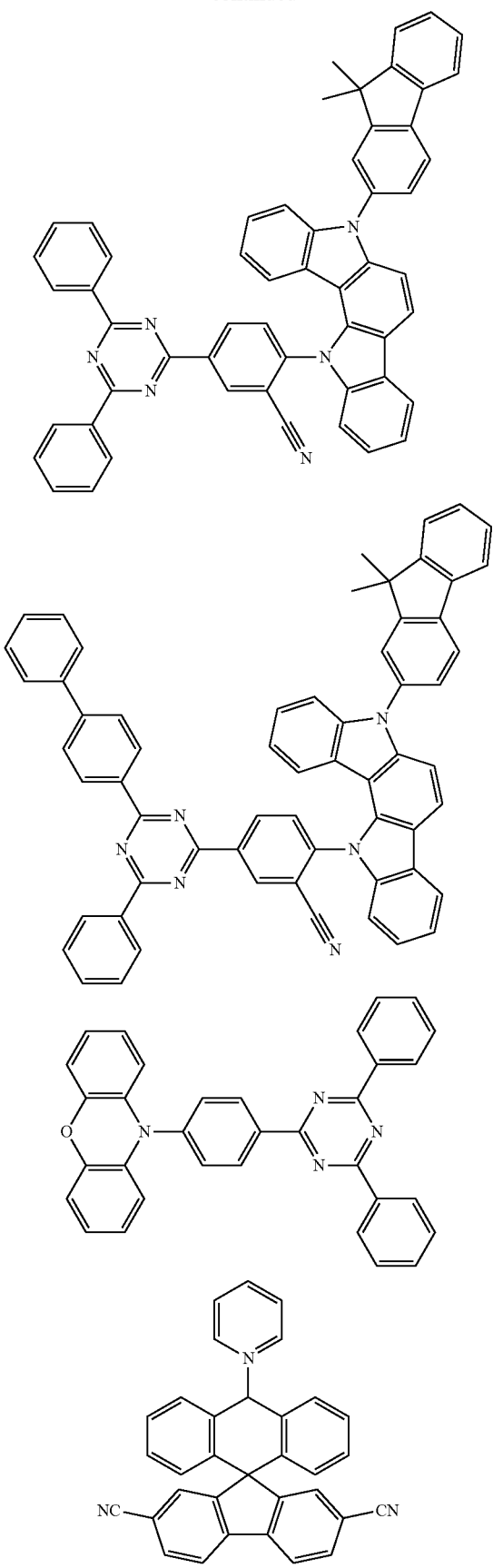
42
-continued
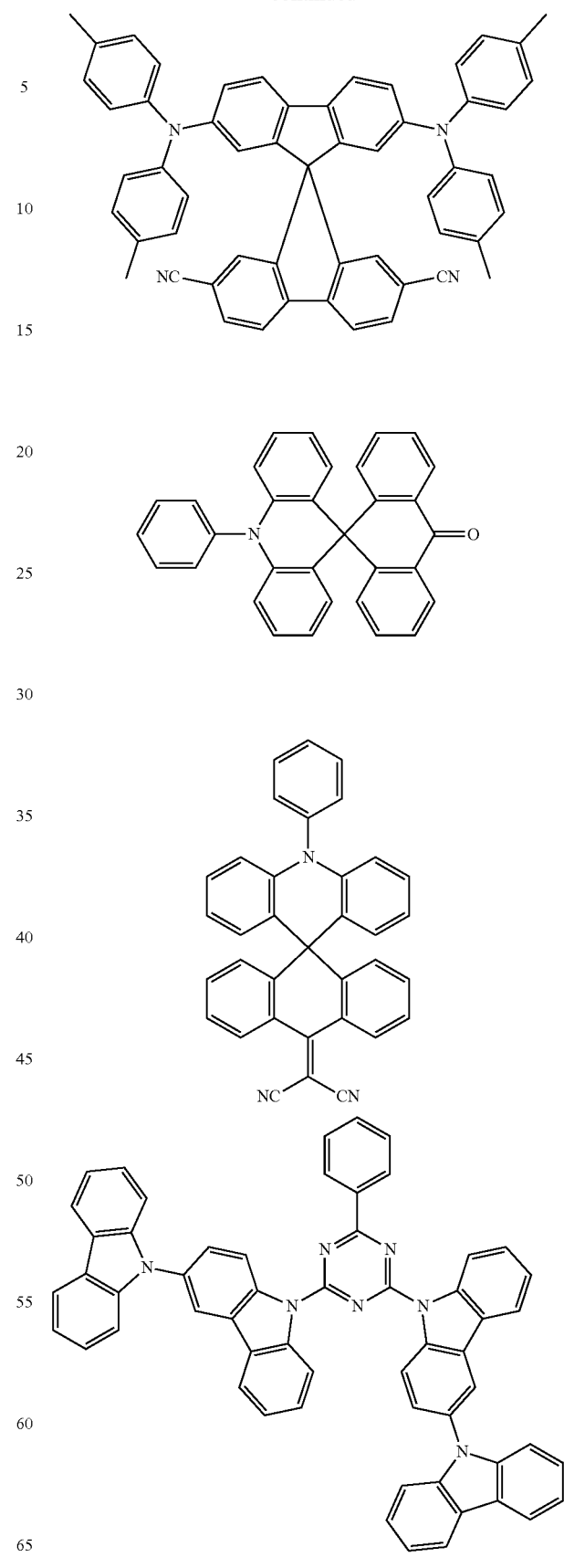

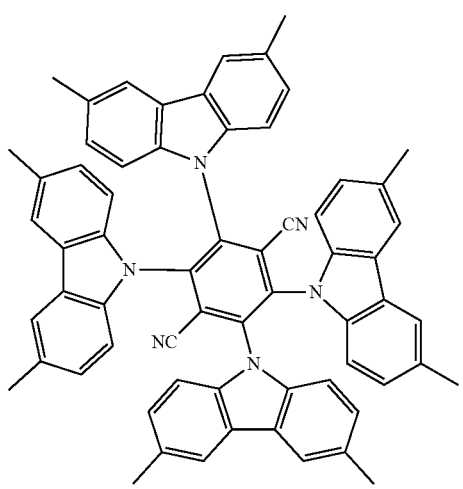
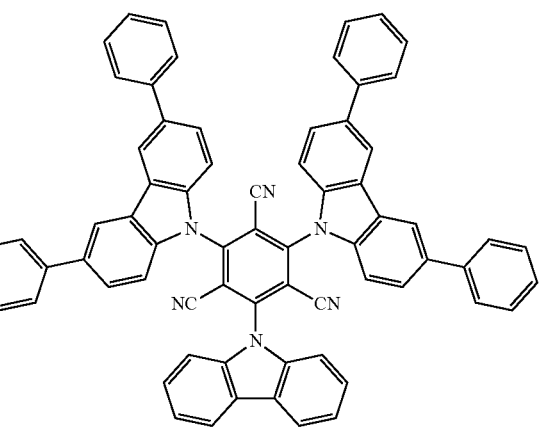
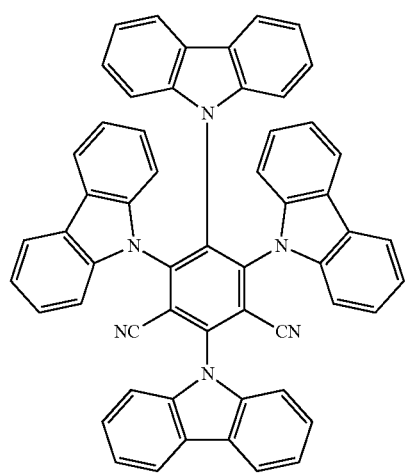
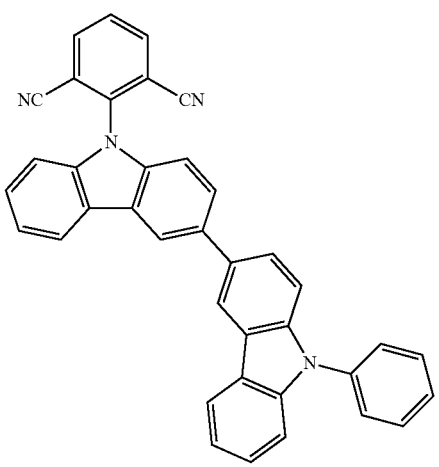
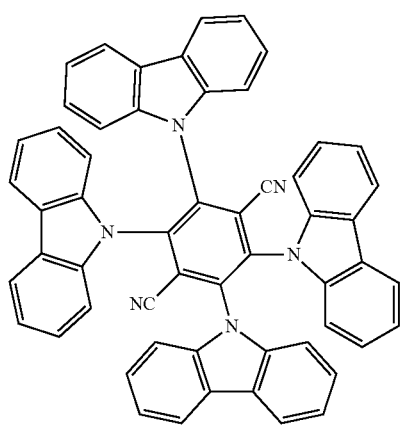
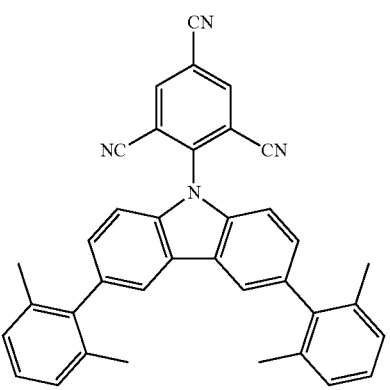

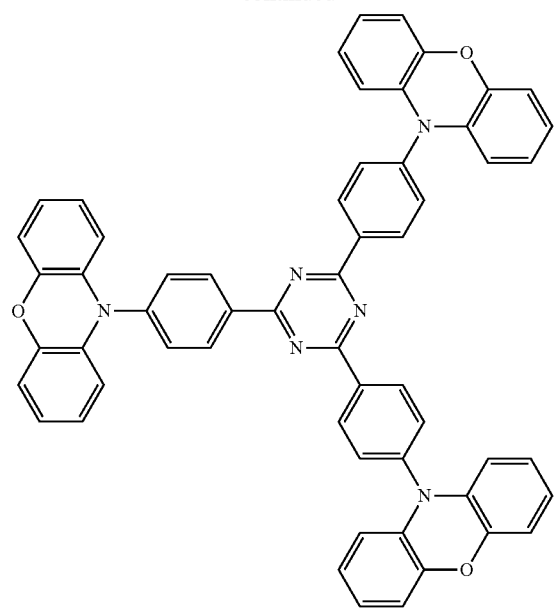
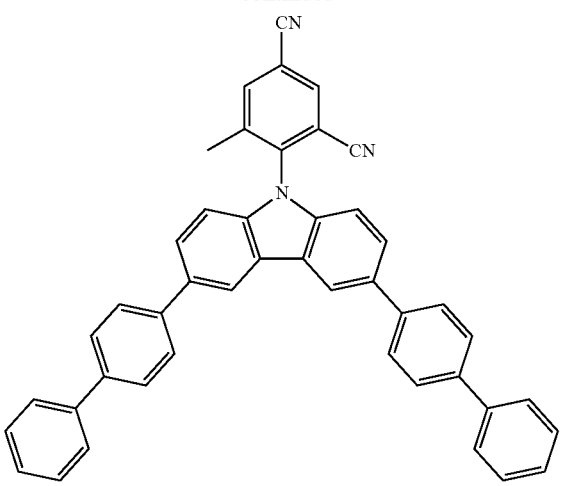
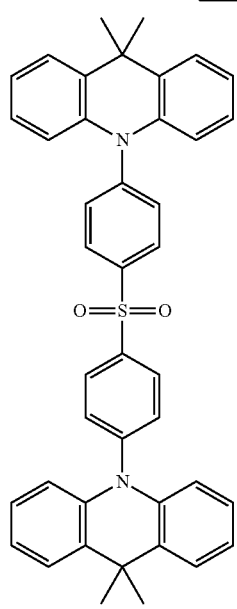
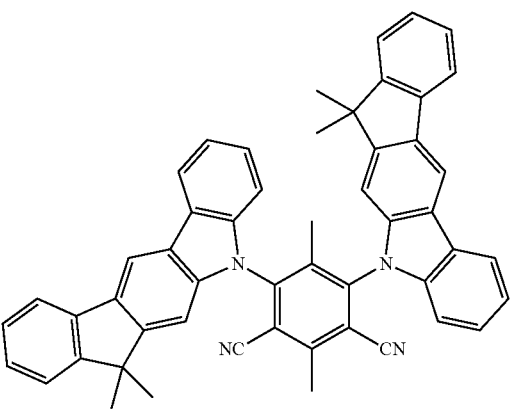
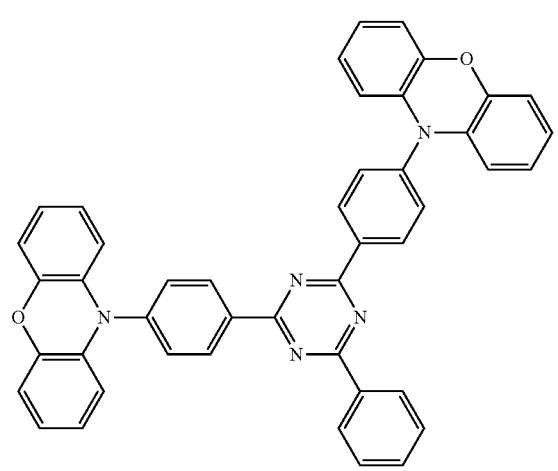

-continued
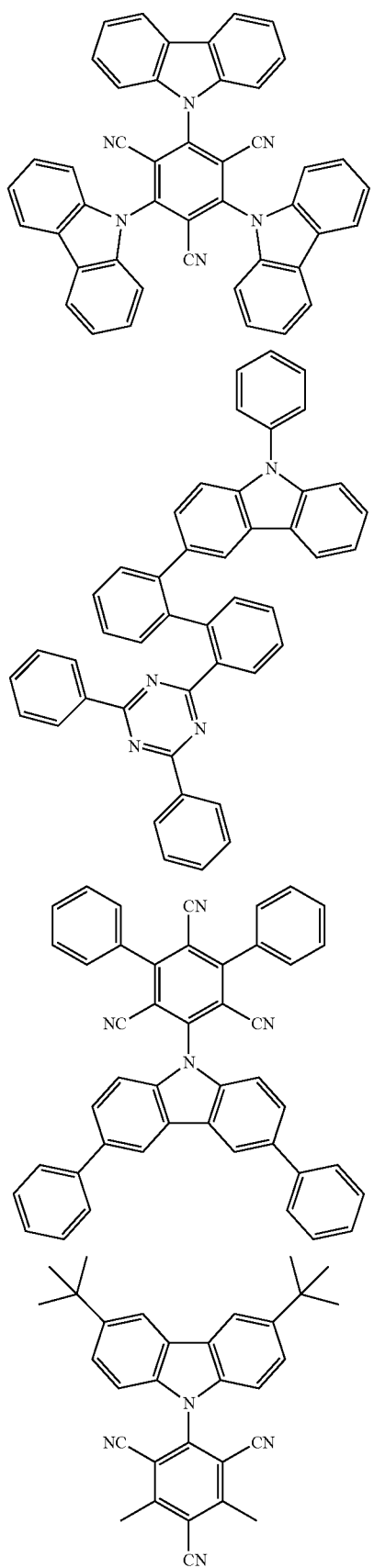
-continued
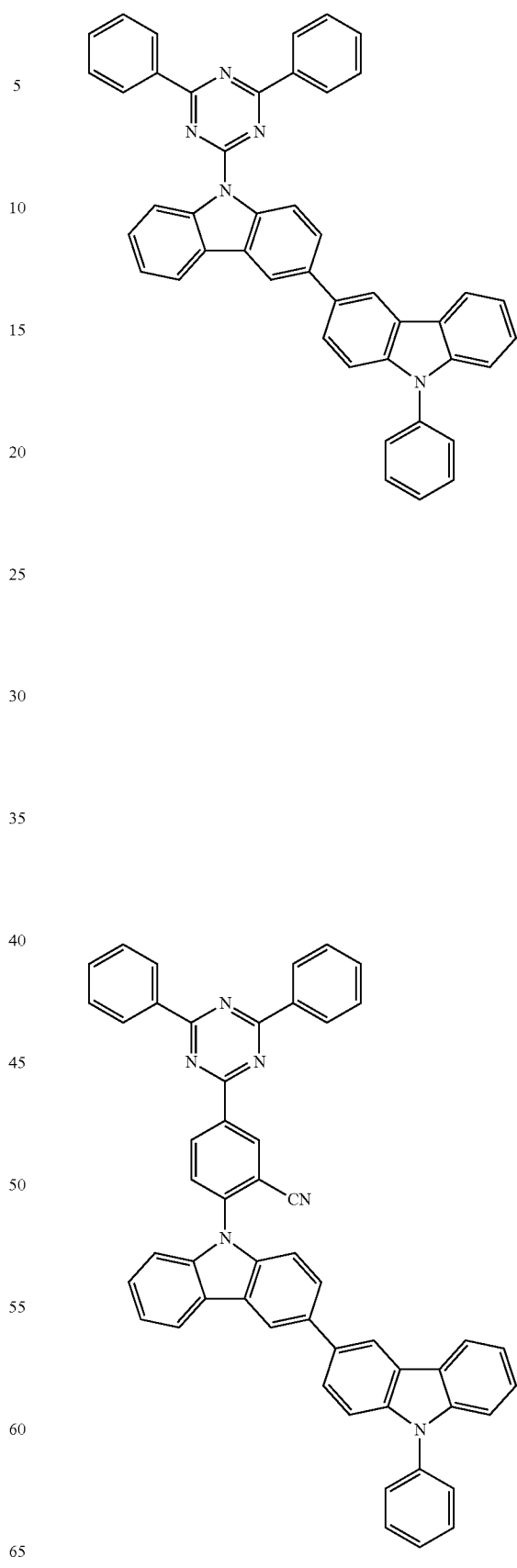

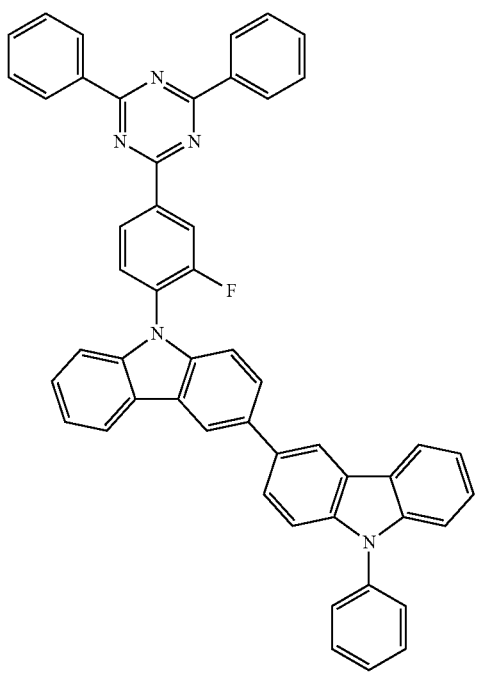
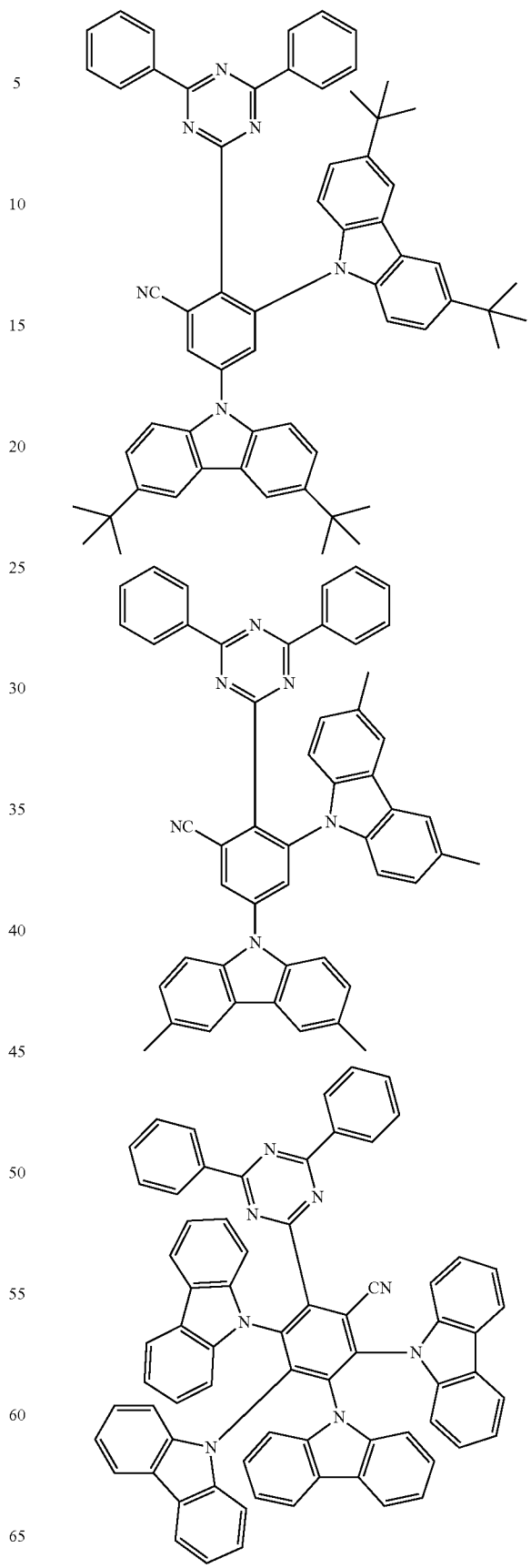

51
-continued
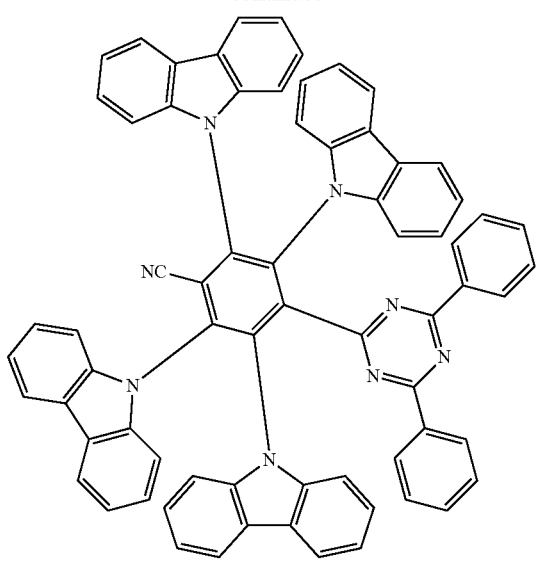
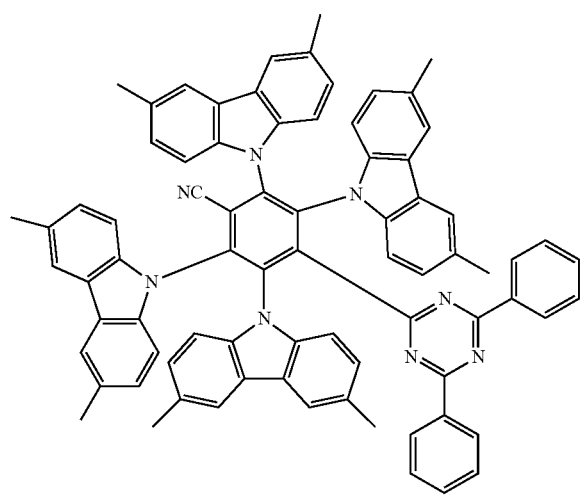
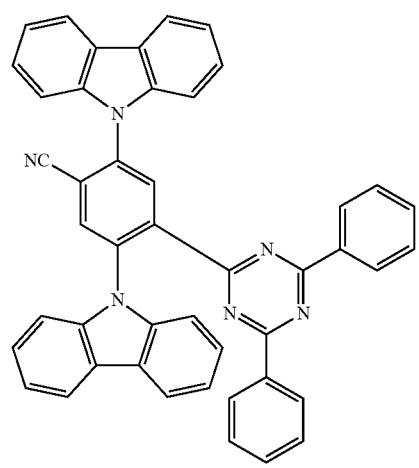
52
-continued
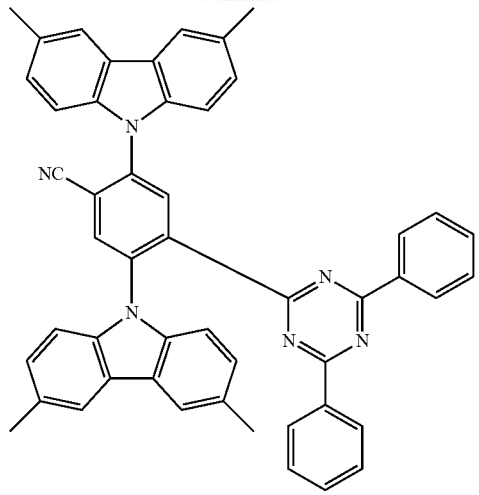
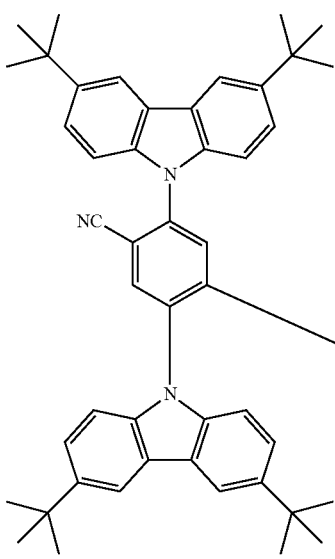
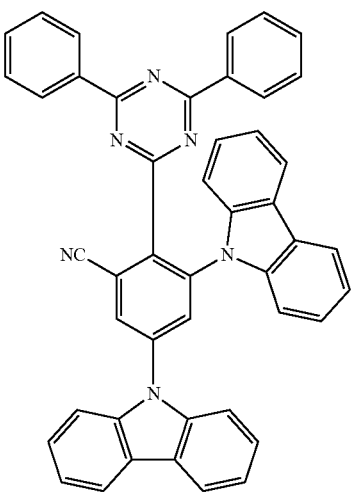

53
-continued
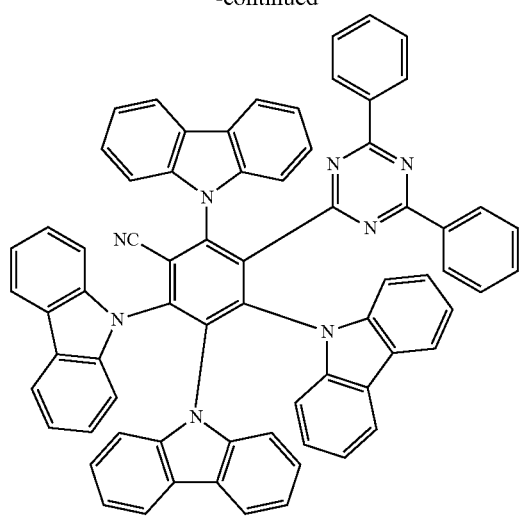
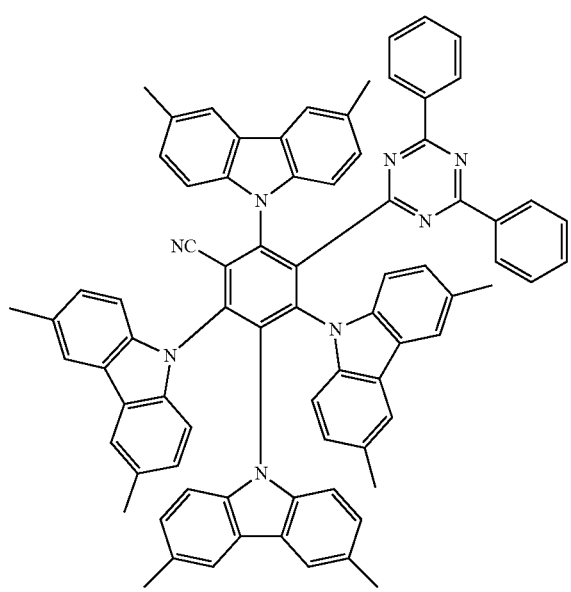
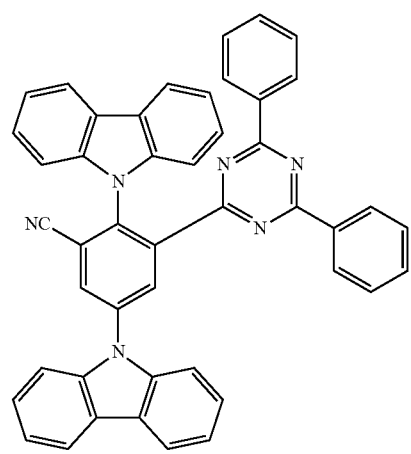
54
-continued
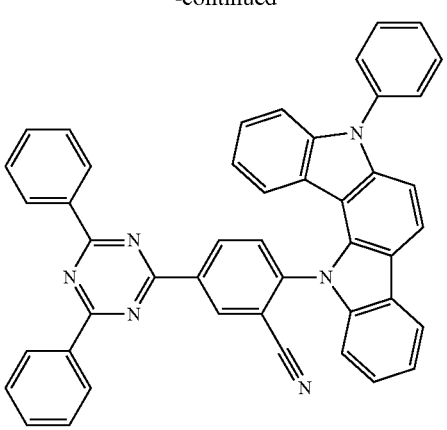
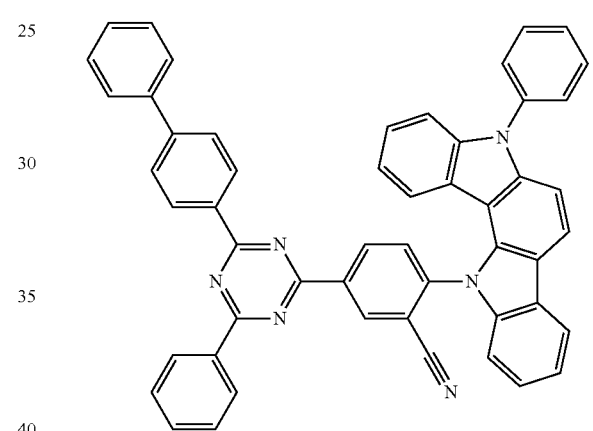
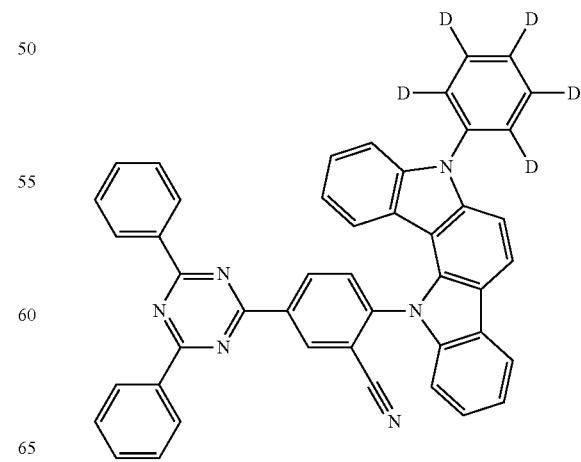

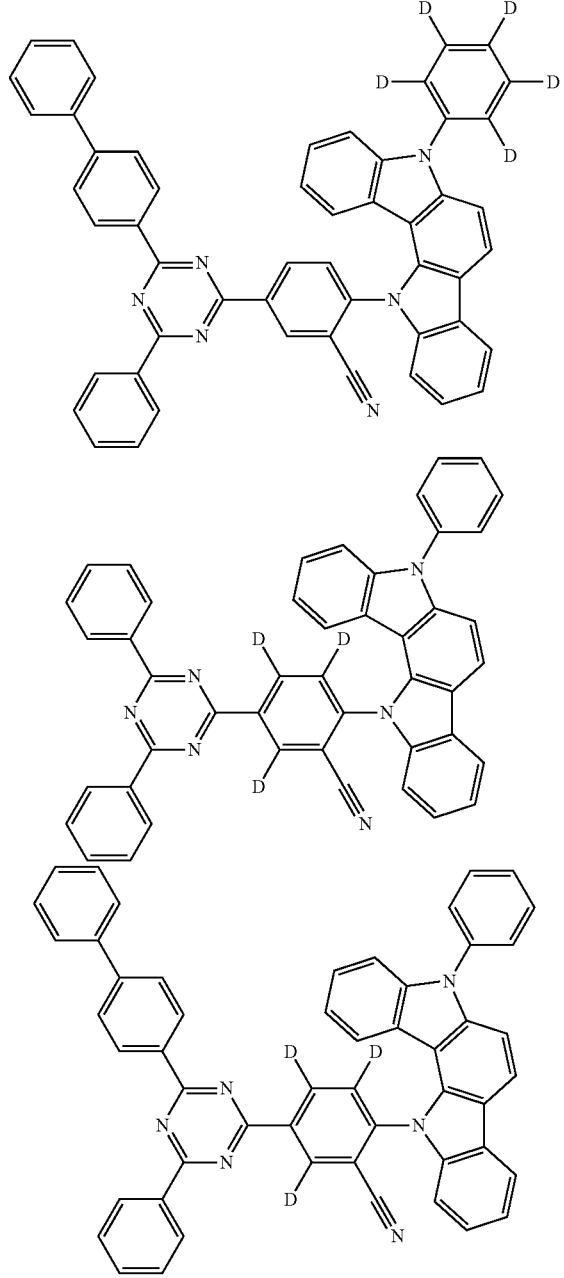

In another exemplary embodiment, the dopant as a delayed fluorescent material in the EML 360 may include, but are not limited to, 10-(4-(4,6-diphenyl-1,3,5-triazin-2-yl)phenyl)-9,9-dimethyl-9,10-dihydroacridine (DMAC-TRZ), 10,10'-(4,4'-sulfonylbis(4,1-phenylene))bis(9,9-dimethyl-9,10-dihydroacridine) (DMAC-DPS), 10-phenyl-10H,10'H-spiro[acridine-9,9'-anthracen]-10'-one (ACRSA), 3,6-dibenzoyl-4,5-di(1-methyl-9-phenyl-9H-carbazoyl)-2-ethynylbenzonitrile (Cz-VPN), 9,9',9'''-(5-(4,6-diphenyl-1,3,5-triazin-2-yl)benzene-1,2,3-triyl) tris(9H-carbazole) (TcZTrz), 9,9'-(5-(4,6-diphenyl-1,3,5-triazin-2-yl)-1,3-phenylene)bis(9H-carbazole) (DczTrz), 9,9',9'', 9'''-((6-phenyl-1,3,5-triazine-2,4-diyl)bis(benzene-5,3,1-triyl))tetrakis(9H-carbazole) (DDczTrz), bis(4-(9H-3,9'-bicarbazol-9-yl) phenyl)methanone (CC2BP), 9'-[4-(4,6-diphenyl-1,3,5-triazin-2-yl)phenyl]-3,3''',6,6''-tetraphenyl-9,3': 6',9''-ter-9H-carbazole (BDPCC-TPTA), 9'-[4-(4,6-diphenyl-1,3,5-triazin-2-yl)phenyl]-9,3':,6',9''-ter-9H-carbazole (BCC-TPTA), 9,9'-(4,4'-sulfonylbis(4,1-phenylene))bis(3,6-dimethoxy-9H-carbazole) (DMOC-DPS), 9-(4-(4,6-diphenyl-1,3,5-triazin-2-yl)phenyl)-3',6'-diphenyl-9H-3,9'-bicarbazole (DPCC-TPTA), 10-(4,6-diphenyl-1,3,5-triazin-2-yl)-10H-phenoxazine (Phen-TRZ), 9-(4-(4,6-diphenyl-1,3,5-triazin-2-yl)phenyl)-9H-carbazole (Cab-Ph-TRZ), 1,2,3,5-Tetrakis(3,6-carbazol-9-yl)-4,6-dicyanobenzene (4CzIPN), 2,3,4,6-tetra(9H-carbazol-9-yl)-5-fluorobenzonitrile (4CZFCN), 10-(4-(4,6-diphenyl-1,3,5-triazin-2-yl)phenyl)-10H-spiro[acridine-9,9'-xanthene] and/or 10-(4-(4,6-diphenyl-1,3,5-triazin-2-yl)phenyl)-10H-spiro[acridine-9,9'-fluorene] (SpiroAC-TRZ).

When the EML 360 includes the host and the dopant having the delayed fluorescent property, the EML 360 may include the dopant of about 1 to about 70% by weight, preferably of about 10 to about 50% by weight, and more preferably of about 20 to about 50% by weight. The EML 360 may be laminated with a thickness of, but are not limited to, about 10 to about 200 nm, preferably about 20 to about 100 nm, and more preferably about 30 to about 50 nm.

Figure 5:
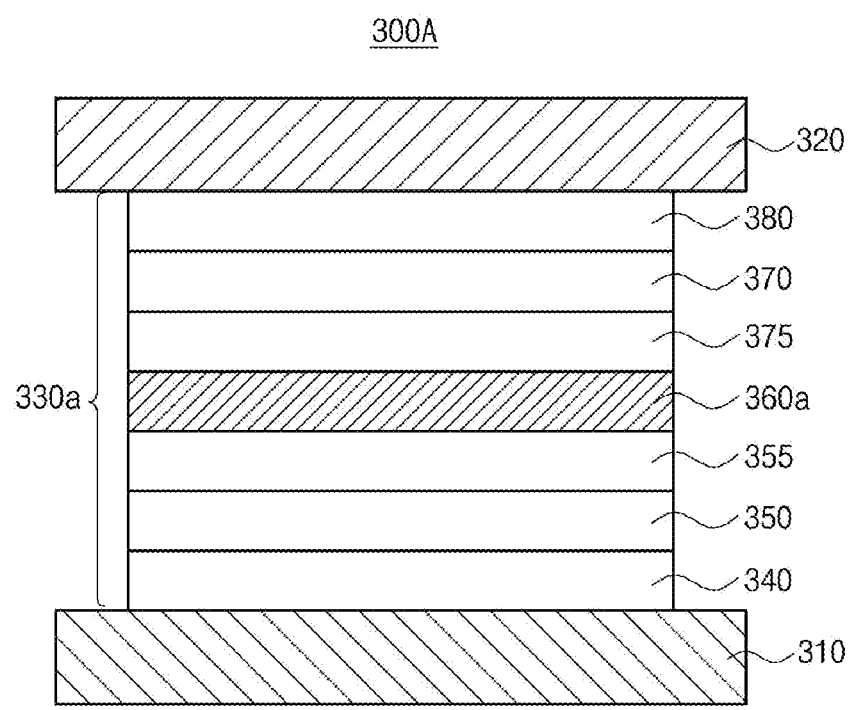
FIG. 5 is a schematic cross-sectional view illustrating an organic light emitting diode in accordance with another exemplary embodiment of the present disclosure.

In the above first embodiment, the EML 360 includes only one dopant having the delayed fluorescent property. Unlike that embodiment, the EML may include plural dopants having different luminous properties. FIG. 5 is a schematic cross-sectional view illustrating an organic light emitting diode in accordance with another exemplary embodiment of the present disclosure. As illustrated in FIG. 5, the OLED 300A according to the second embodiment of the present disclosure includes first and second electrodes 310 and 320 facing each other and an emitting unit 330a disposed between the first and second electrodes 310 and 320.

In one exemplary embodiment, the emitting unit 330a as an emission layer includes a HIL 340, a HTL 350, an EML 360a, an ETL 370 and an ETL 380 each of which is laminated sequentially over the first electrode 310. Alternatively, the emitting unit 330a may further include a first exciton blocking layer, i.e. an EBL 355 disposed between the HTL 350 and the EML 360a and/or a second exciton blocking layer, i.e. a HBL 375 disposed between the EML 360a and the ETL 370. The emitting unit 330a may have the same configurations and materials as the emitting unit 330 in FIG. 2 except the EML 360a.

The EML 360a may include a host (a first host), a first dopant and a second dopant. The first dopant may be a delayed fluorescent dopant (T dopant; TD) and the second dopant may be a fluorescent dopant (F dopant; FD). In this case, the organic compound having the structure of any one in Chemical Formulae 1 to 6 may be used as the host. When the EML 360a includes the delayed fluorescent dopant and the fluorescent dopant, the OLED 300A can implement hyper-fluorescence enhancing its luminous efficiency by adjusting energy levels among the luminous materials, i.e. the host and the dopants.

When an EML includes only the dopant which has the delayed fluorescent property and has the structure of any one in Chemical Formula 7, the EML may implement high internal quantum efficiency as the prior art phosphorescent materials including heavy metals because the dopant can exhibit 100% internal quantum efficiency in theory. However, because of the bond formation between the electron acceptor and the electron donor and sterical twists within the delayed fluorescent material, additional charge transfer transition (CT transition) is caused thereby, so that the delayed fluorescent materials show emission spectra having very broad FWHM in the course of emission, which results in poor color purity. In addition, delayed fluorescent material utilizes the triplet exciton energy as well as the singlet exciton energy in the luminous process with rotating each moiety within its molecular structure, which results in twisted internal charge transfer (TICT). As a result, a luminous lifetime of an OLED including only the delayed fluorescent materials may be reduced owing to weakening of molecular bonding forces among the delayed fluorescent materials.

In the second embodiment, the EML 360a further includes the second dopant, which may be a fluorescent or phosphorescent material, in order to prevent the color purity and luminous lifetime from being reduced in case of using only the delayed fluorescent materials. The triplet exciton energy of the first dopant (T dopant), which may be the delayed fluorescent material, is converted to the singlet exciton energy of its own by RISC mechanism, then the converted singlet exciton energy of the first dopant can be transferred to the second dopant (F dopant), which may be the fluorescent or phosphorescent material, in the same EML 360a by Dexter energy transfer mechanism, which transfer exciton energies depending upon wave function overlaps among adjacent molecules by inter-molecular electron exchanges and exciton diffusions.

When the EML 360a includes the host which is the organic compound having the structure of any one in Chemical Formulae 1 to 6, the first dopant (T dopant) which may be the organic compound having the structure of any one in Chemical Formula 7 and having the delayed fluorescent property and the second dopant (F dopant) which may be the fluorescent or phosphorescent material, it is necessary to adjust properly energy levels amount those luminous materials.

Figure 6:
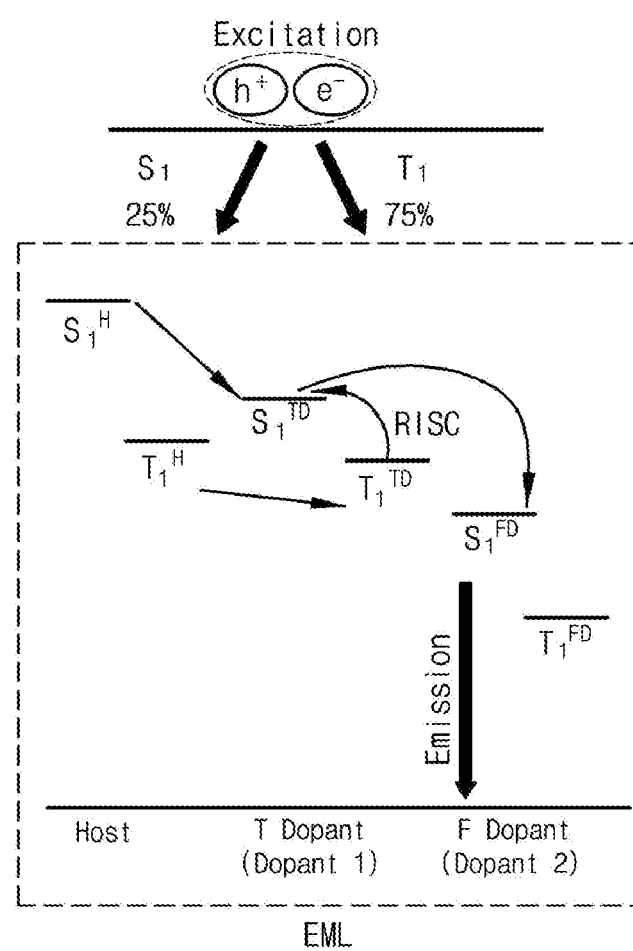
FIG. 6 is a schematic diagram illustrating luminous mechanism by energy level bandgap among luminous materials in accordance with another exemplary embodiment of the present disclosure.

FIG. 6 is a schematic diagram illustrating luminous mechanism by energy level bandgap among luminous materials in accordance with another exemplary embodiment of the present disclosure. An energy level bandgap between an excited state singlet energy level $S_1^{TD}$ and an excited state triplet energy level $T_1^{TD}$ of the first dopant (T dopant) may be equal to or less than about 0.3 eV in order to realize the delayed fluorescence. In addition, an excited state singlet energy level $S_1^H$ and an excited state triplet energy level $T_1^H$ of the host is higher than the excited state singlet energy level $S_1^{TD}$ and the excited state triplet energy level $T_1^{TD}$ of the first dopant, respectively. As an example, the excited state triplet energy level $T_1^H$ of the host may be higher than the excited state triplet energy level $T_1^{TD}$ of the first dopant by at least about 0.2 eV. Moreover, the excited state triplet energy level $T_1^{TD}$ of the first dopant is higher than an excited state triplet energy level $T_1^{FD}$ of the second dopant. In one exemplary embodiment, the excited state singlet energy level $S_1^{TD}$ of the first dopant may be higher than an excited state singlet energy level $S_1^{FD}$ of the second dopant as a fluorescent material.

In addition, an energy level bandgap ($|HOMO^H-HOMO^{TD}|$) between a HOMO energy level ($HOMO^H$) of the host and a HOMO energy level ($HOMO^{TD}$) of the first dopant, or an energy level bandgap ($|LUMO^H-LUMO^{TD}|$) between a LUMO energy level ($LUMO^H$) of the host and a LUMO energy level ($LUMO^{TD}$) of the first dopant may be equal to or less than about 0.5 eV.

For example, the host may include the organic compound having the structure of any one in Chemical Formulae 1 to 6 and the first dopant may include, but are not limited to, organic compound having the structure of any one in Chemical Formula 7. Alternatively, the second dopant may include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

The exciton energy should be effectively transferred from the first dopant as the delayed fluorescent material to the second dopant as the fluorescent or phosphorescent material in order to implement hyper-fluorescence. With regard to energy transfer efficiency from the delayed fluorescent material to the fluorescent or phosphorescent material, an overlap between an emission spectrum of the delayed fluorescent material and an absorption spectrum of the fluorescent or phosphorescent material can be considered. As an example, a fluorescent or phosphorescent material having an absorption spectrum with overlapping area with an emission spectrum of the first dopant may be used as the second dopant in order to transfer exciton energy efficiently from the first dopant to the second dopant.

In one exemplary embodiment, the fluorescent material as the second dopant may have, but are not limited to, quinolino-acridine core. As an example, the second dopant having the quinolino-acridine core may include 5,12-dimethylquinolino[2,3-b]acridine-7,14(5H, 12H)-dione($S_1$: 2.3 eV; $T_1$: 2.0 eV; LUMO: −3.0 eV; HOMO: −5.4 eV), 5,12-diethylquinolino[2,3-b]acridine-7,14(5H, 12H)-dione($S_1$: 2.3 eV; $T_1$: 2.2 eV; LUMO: −3.0 eV; HOMO: −5.4 eV), 5,12-dibutyl-3,10-difluoroquinolino[2,3-b]acridine-7,14(5H, 12H)-dione($S_1$: 2.2 eV; $T_1$: 2.0 eV; LUMO: −3.1 eV; HOMO: −5.5 eV), 5,12-dibutyl-3,10-bis(trifluoromethyl)quinolino[2,3-b]acridine-7,14(5H, 12H)-dione($S_1$: 2.2 eV; $T_1$: 2.0 eV; LUMO: −3.1 eV; HOMO: −5.5 eV), 5,12-dibutyl-2,3,9,10-tetrafluoroquinolino[2,3-b]acridine-7,14(5H, 12H)-dione($S_1$: 2.0 eV; $T_1$: 1.8 eV; LUMO: −3.3 eV; HOMO: −5.5 eV).

In addition, the fluorescent material as the second dopant may include, but are not limited to, 1,1,7,7-tetramethyl-2,3,6,7-tetrahydro-1H,5H-benzo[ij]quinolizin-9-yl)ethenyl]-4H-pyran-4-ylidene}propanedinitrile(DCJTB; $S_1$: 2.3 eV; $T_1$: 1.9 eV; LUMO: −3.1 eV; HOMO: −5.3 eV). Moreover, metal complexes which can emit light of red, green or blue color may be used as the second dopant.

In one exemplary embodiment, the weight ratio of the host may be larger than the weight ratio of the first and second dopants in the EML 360a, and the weight ratio of the first dopant may be larger than the weight ratio of the second dopant. In an alternative embodiment, the weight ratio of the host is larger than the weight ratio of the first dopant and the weight ratio of the first dopant is larger than the weight ratio of the second dopant. When the weight ratio of the first dopant is larger than the weight ratio of the second dopant, exciton energy can be transferred efficiently from the first dopant to the second dopant by a Dexter energy transfer mechanism. As an example, the EML 360a includes the host of about 60 to about 75% by weight, the first dopant of about 20 to about 40% by weight and the second dopant of about 0.1 to about 5% by weight.

Figure 7:
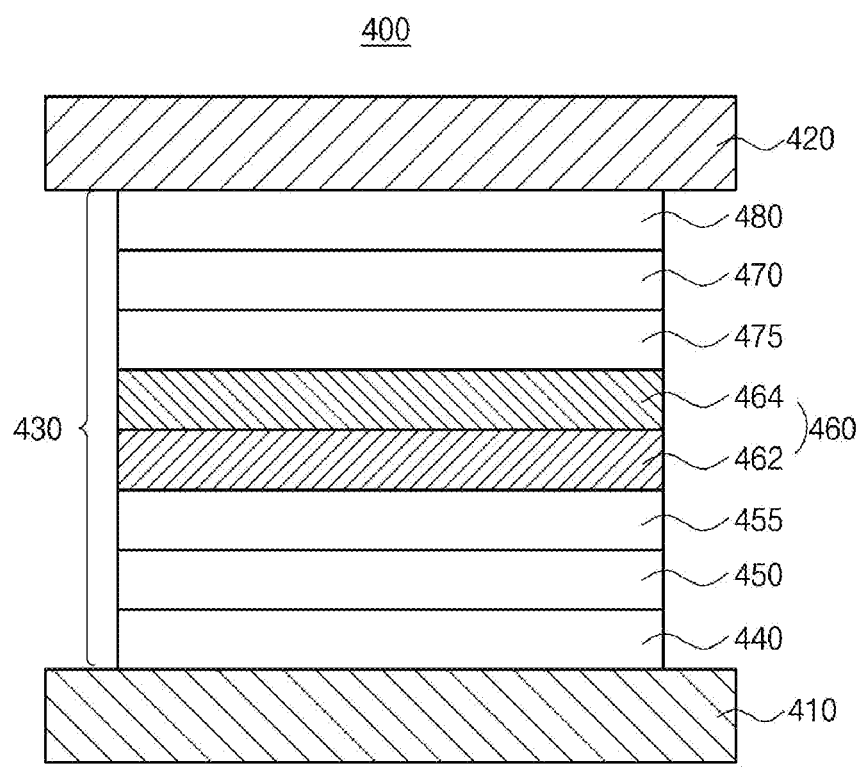
FIG. 7 is a schematic cross-sectional view illustrating an organic light emitting diode in accordance with another exemplary embodiment of the present disclosure.

The OLEDs in accordance with the previous embodiments have a single-layered EML. Alternatively, an OLED in accordance with the present disclosure may include multiple-layered EML. FIG. 7 is a schematic cross-sectional view illustrating an organic light emitting diode having a double-layered EML in accordance with another exemplary embodiment of the present disclosure.

As illustrated in FIG. 7, the OLED 400 in accordance with an exemplary third embodiment of the present disclosure includes first and second electrodes 410 and 420 facing each other and an emitting unit 430 as an emission layer disposed between the first and second electrodes 410 and 420.

In one exemplary embodiment, the emitting unit 430 includes an HIL 440, an HTL 450, and EML 460, an ETL 470 and an EIL 480 each of which is laminated sequentially over the first electrode 410. In addition, the emitting unit 430 may further include an EBL 455 as a first exciton blocking layer disposed between the HTL 450 and the EML 460, and/or an HBL 475 as a second exciton blocking layer disposed between the EML 460 and the ETL 470.

As described above, the first electrode 410 may be an anode and may include, but are not limited to, a conductive material having a relatively large work function values such as ITO, IZO, SnO, ZnO, ICO, AZO, and the likes. The second electrode 420 may be a cathode and may include, but are not limited to, a conductive material having a relatively small work function values such as Al, Mg, Ca, Ag, alloy thereof or combination thereof.

The HIL 440 is disposed between the first electrode 410 and the HTL 450. The HIL 440 may include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 440 may be omitted in compliance with the structure of the OLED 400.

The HTL 450 is disposed adjacently to the EML 460 between the first electrode 410 and the EML 460. The HTL 450 may include, but are not limited to, aromatic amine compounds such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 460 includes a first EML (EML1) 462 and a second EML (EML2) 464. The EML1 462 is disposed between the EBL 455 and the HBL 475 and the EML2 464 is disposed between the EML1 462 and the HBL 475. One of the EML1 462 and the EML2 464 includes a first dopant (T dopant) having a delayed fluorescent property, for example, an organic compound having the structure of any one in Chemical Formula 7, the other of the EML1 462 and the EML2 464 includes a second dopant as a fluorescent or phosphorescent material. The configuration and energy levels among the luminous materials in the EML 460 will be explained in more detail below.

The ETL 470 is disposed between the EML 460 and the EIL 480. In one exemplary embodiment, the ETL 470 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes. As an example, the ETL 470 may include, but are not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 480 is disposed between the second electrode 420 and the ETL 470. In one exemplary embodiment, the EIL 480 may include, but are not limited to, an alkali halide and/or an alkali earth halide such as LiF, CsF, NaF, BaF$_2$ and the likes, and/or an organic metal compound such as lithium benzoate, sodium stearate, and the likes.

The EBL 455 is disposed between the HTL 450 and the EML 460 for controlling and preventing electron transportations between the HTL 450 and the EML 460. As an example, The EBL 455 may include, but are not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, 2,8-bis(9-phenyl-9H-carbazol-3-yl)dibenzo[b,d]thiophene and/or 3,6-bis(N-carbazolyl)-N-phenyl-carbazole.

The HBL 475 is disposed between the EML 460 and the ETL 470 for preventing hole transportations between the EML 460 and the ETL 470. In one exemplary embodiment, the HBL 475 may include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 475 may include a compound having a relatively low HOMO energy level compared to the emitting material in EML 460. The HBL 475 may include, but are not limited to, BCP, BAlq, Alq$_3$, PBD, spiro-PBD, Liq, B3PYMPM, DPEPO, 9-(6-(9H-carbazol-9-yl)pyridine-3-yl)-9H-3,9'-bicarbazole and combination thereof.

In the exemplary third embodiment, the EML1 462 includes a first host and a first dopant, which is a delayed fluorescent material and the EML2 464 includes a second host and a second dopant, which is a fluorescent or phosphorescent material.

The EML1 462 includes the first host which is the organic compound having the structure of any one in Chemical Formulae 1 to 6 and the first dopant which is the delayed fluorescent material. An energy level bandgap ($\Delta E_{ST}^{TD}$) between the excited state singlet energy level $S_1^{TD}$ and the excited state triplet energy level $T_1^{TD}$ of the first dopant is very small ($\Delta E_{ST}^{TD}$ is equal to or less than about 0.3 eV; See, FIG. 3) so that triplet exciton energy of the first dopant can be transferred to the singlet exciton energy of its own by RISC mechanism. While the first dopant has high internal quantum efficiency, but it has poor color purity due to its wide FWHM (full-width half maximum).

On the contrary, the EML2 464 may include the second host and the second dopant as a fluorescent material. While the second dopant as a fluorescent material has advantage of high color purity due to its narrow FWHM, but its internal quantum efficiency is low because its triplet exciton cannot be involved in a luminous process.

However, in this exemplary embodiment, the singlet exciton energy and the triplet exciton energy of the first dopant, which has the delayed fluorescent property, in the EML1 462 can be transferred to the second dopant, which may be the fluorescent or phosphorescent material, in the EML2 464 disposed adjacently to the EML1 462 by FRET (Forster resonance energy transfer) mechanism, which transfers energy non-radially through electrical fields by dipole-dipole interactions. Accordingly, the ultimate emission occurs in the second dopant within the EML2 464.

In other words, the triplet exciton energy of the first dopant is converted to the singlet exciton energy of its own in the EML1 462 by RISC mechanism. Then, the converted singlet exciton energy of the first dopant is transferred to the singlet exciton energy of the second dopant because the excited state singlet energy level $S_1^{TD}$ of the first dopant is higher than the excited state singlet energy level $S_1^{FD}$ of the second dopant (See, FIG. 8). The second dopant in the EML2 464 can emit light using the triplet exciton energy as well as the singlet exciton energy.

As the exciton energy, which is generated at the first dopant as the delayed fluorescent material in the EML1 462, is transferred from the first dopant to the second dopant in the EML2 464, a hyper-fluorescence can be realized. In this case, the first dopant only acts as transferring energy to the second dopant. Substantial light emission is occurred in the EML2 464 including the second dopant which is the fluorescent or phosphorescent dopant and has a narrow FWHM. Accordingly, the OLED 400 can enhance its quantum efficiency and improve its color purity due to narrow FWHM.

Figure 8:
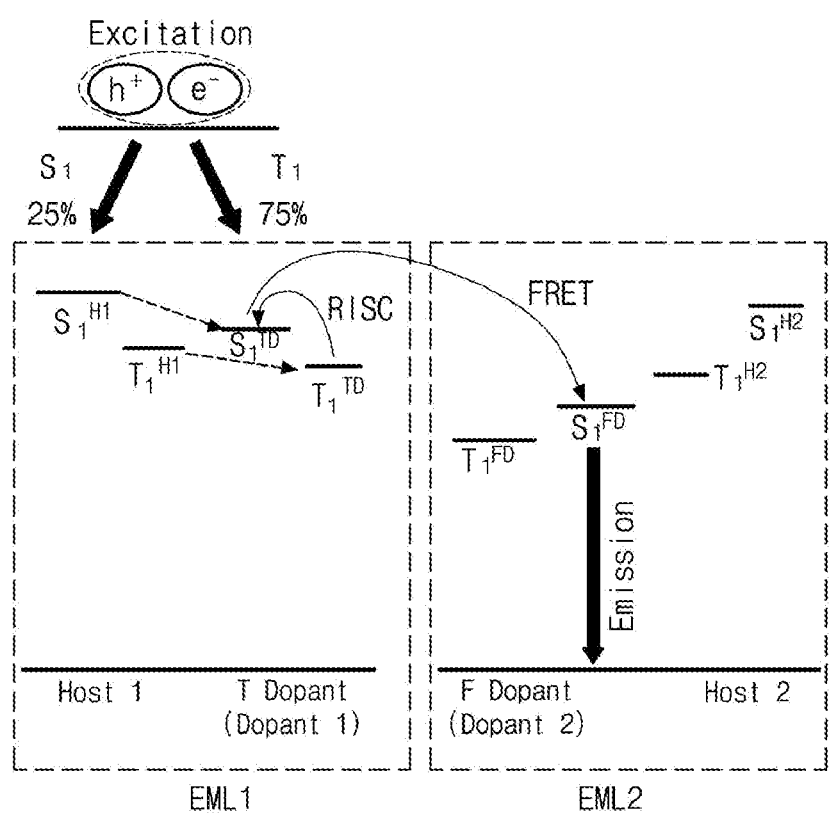
FIG. 8 is a schematic diagram illustrating luminous mechanism by energy level bandgap among luminous materials in accordance with another exemplary embodiment of the present disclosure.

Each of the EML1 462 and the EML2 464 includes the first host and the second host, respectively. The exciton energies generated at the first and second hosts should be transferred to the first dopant as the delayed fluorescent material to emit light. It is necessary to adjust energy levels among the luminous materials in order to realize a hyperfluorescence. FIG. 8 is a schematic diagram illustrating luminous mechanism by energy level bandgap among luminous materials in accordance with another exemplary embodiment of the present disclosure.

As illustrated in FIG. 8, excited state singlet energy levels $S_1^{H1}$ and $S_1^{H2}$ and excited state triplet energy levels $T_1^{H1}$ and $T_1^{H2}$ of the first and second hosts should be higher than the excited state singlet energy level $S_1^{TD}$ and the excited state triplet energy level $T_1^{TD}$ of the first dopant as the delayed fluorescent material, respectively.

For example, when each of the excited state triplet energy levels $T_1^{H1}$ and $T_1^{H2}$ of the first and second hosts is not high enough than the excited state triplet energy level $T_1^{TD}$ of the first dopant, the triplet exciton of the first dopant may be reversely transferred to the excited state triplet energy levels $T_1^{H1}$ and $T_1^{H2}$ of the first and second hosts, which cannot utilize triplet exciton energy. Accordingly, the excitons of the triplet energy level $T_1^{TD}$ of the first dopant may be quenched as a non-emission and the triplet state excitons of the first dopant cannot be involved in the emission. As an example, each of the excited state triplet energy levels $T_1^{H1}$ and $T_1^{H2}$ of the first and second hosts may be higher than the excited state triplet energy level $T_1^{TD}$ of the first dopant by at least about 0.2 eV.

The excited state singlet energy level $S_1^{H2}$ of the second host is higher than an excited state singlet energy level $S_1^{FD}$ of the second dopant. In this case, the singlet exciton energy generated at the second host can be transferred to the excited singlet energy level $S_1^{FD}$ of the second dopant.

In addition, it is necessary for the EML 460 to implement high luminous efficiency and color purity as well as to transfer exciton energy efficiently from the first dopant, which is converted to ICT complex state by RISC mechanism in the EML1 462, to the second dopant which is the fluorescent or phosphorescent material in the EML2 464. In order to realize such an OLED 400, the excited state triplet energy level $T_1^{TD}$ of the first dopant is higher than an excited state triplet energy level $T_1^{FD}$ of the second dopant. In one exemplary embodiment, the excited state singlet energy level $S_1^{TD}$ of the first dopant may be higher than an excited state singlet energy level $S_1^{FD}$ of the second dopant as a fluorescent material.

In one exemplary embodiment, the energy level bandgap between the excited state singlet energy level $S_1^{TD}$ and the excited state triplet energy level $T_1^{TD}$ of the first dopant may be equal to or less than about 0.3 eV. In addition, an energy level bandgap ($|HOMO^H - HOMO^{TD}|$) between a HOMO energy level ($HOMO^H$) of the first and/or second hosts and a HOMO energy level ($HOMO^{TD}$) of the first dopant, or an energy level bandgap ($|LUMO^H - LUMO^{TD}|$) between a LUMO energy level ($LUMO^H$) of the first and/or second hosts and a LUMO energy level ($LUMO^{TD}$) of the first dopant may be equal to or less than about 0.5 eV.

When the luminous materials do not satisfy the required energy levels as described above, exciton energies are quenched at the first and second dopants or exciton energies cannot be transferred efficiently from the host to the dopants, so that OLED 400 may have reduced quantum efficiency.

The first host and the second host may be the same or different from each other. For example, each of the first host and the second host may independently include the organic compound having the structure of any one in Chemical Formulae 1 to 6. In one exemplary embodiment, the first dopant may include, but are not limited to, the organic compound having the structure of any one in Chemical Formula 7. In an alternative embodiment, the second dopant may include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

The second dopant may have narrow FWHM and have luminous spectrum having large overlapping area with the absorption spectrum of the first dopant. As an example, the second dopant may include, but are not limited to, an organic compound having a quinolino-acridine core such as 5,12-dimethylquinolino[2,3-b]acridine-7,14(5H, 12H)-dione, 5,12-diethylquinolino[2,3-b]acridine-7,14(5H, 12H)-dione, 5,12-dibutyl-3,10-difluoroquinolino[2,3-b]acridine-7,14 (5H, 12H)-dione, 5,12-dibutyl-3,10-bis(trifluoromethyl)quinolino[2,3-b]acridine-7,14(5H, 12H)-dione, 5,12-dibutyl-2,3,9,10-tetrafluoroquinolino[2,3-b]acridine-7,14(5H, 12H)-dione, DCJTB and any metal complexes which can emit light of red, green or blue color.

In one exemplary embodiment, each of the first and second hosts in the EML1 462 or the EML2 464 may have more weight ratio than the first dopant and the second dopant in the same EMLs 462 and 464, respectively. In addition, the weight ratio of the first dopant in the EML1 462 may be larger than the weight ratio of the second dopant in the EML2 464. In this case, it is possible to transfer enough energy from the first dopant in the EML1 462 to the second dopant in the EML2 464.

As an example, the EML1 462 may include the first dopant of, but are not limited to, about 1 to about 70% by weigh, preferably about 10 to about 50% by weight, and preferably about 20 to about 50% by weight.

The weight ratio of the second host may be larger than the weight ratio of the second dopant in the EML2 464. As an example, the EML2 464 may include the second host, but are not limited to, about 90 to about 99% by weight, and preferably about 95 to about 99% by weight, and the second dopant, but are not limited to, about 1 to about 10% by weight, and preferably about 1 to about 5% by weight.

Each of the EML1 462 and the EML2 464 may be laminated with a thickness of, but are not limited to, about 5 to about 100 nm, preferably about 10 to about 30 nm, and more preferably about 10 to about 20 nm.

When the EML2 464 is disposed adjacently to the HBL 475 in one exemplary embodiment, the second host, which is included in the EML2 464 together with the second dopant, may be the same material as the HBL 475. In this case, the EML2 464 may have a hole blocking function as well as an emission function. In other words, the EML2 464 can act as a buffer layer for blocking holes. In one embodiment, the HBL 475 may be omitted where the EML2 464 may be a hole blocking layer as well as an emitting material layer.

When the EML2 464 is disposed adjacently to the EBL 455 in another exemplary embodiment, the second host may be the same material as the EBL 455. In this case, the EML2 464 may have an electron blocking function as well as an emission function. In other words, the EML2 464 can act as a buffer layer for blocking electrons. In one embodiment, the EBL 455 may be omitted where the EML2 464 may be an electron blocking layer as well as an emitting material layer.

Figure 9:
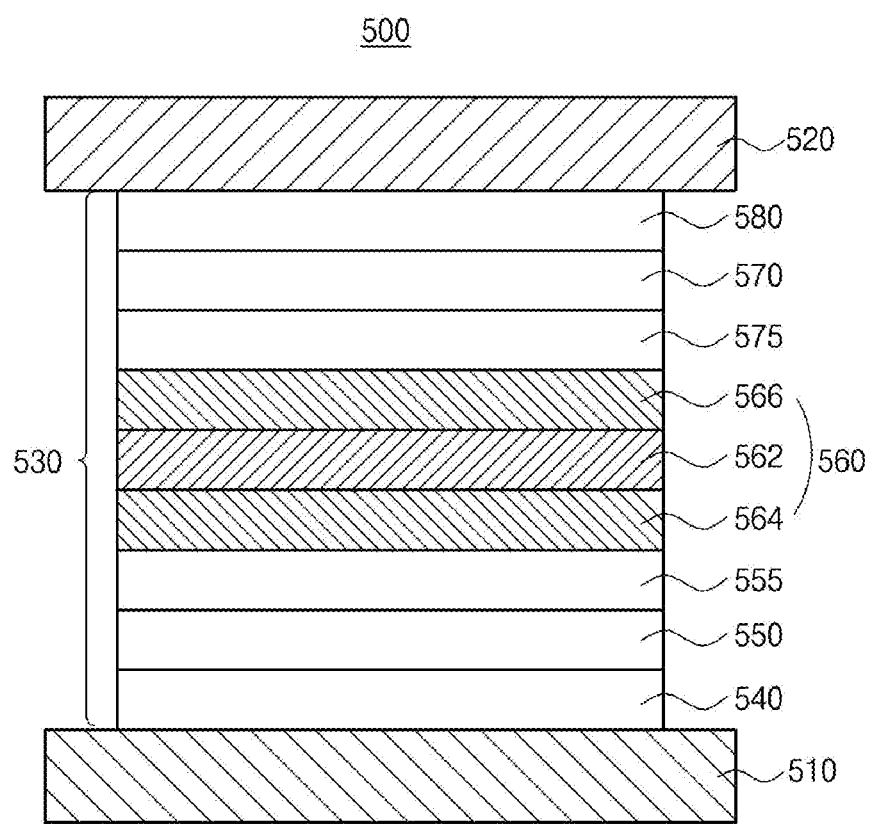
FIG. 9 is a schematic cross-sectional view illustrating an organic light emitting diode in accordance with another exemplary embodiment of the present disclosure.

An OLED having a triple-layered EML will be explained. FIG. 9 is a schematic cross-sectional view illustrating an organic light emitting diode having a triple-layered EML in accordance with another exemplary embodiment of the present disclosure.

As illustrated in FIG. 9, an OLED 500 in accordance with the fourth embodiment of the present disclosure includes first and second electrodes 510 and 520 facing each other and an emitting unit 530 as an emission layer disposed between the first and second electrodes 510 and 520.

In one exemplary embodiment, the emitting unit 530 includes an HIL 540, an HTL 550, and EML 560, an ETL 570 and an EIL 580 each of which is laminated sequentially over the first electrode 510. In addition, the emitting unit 530 may further include an EBL 555 as a first exciton blocking layer disposed between the HTL 550 and the EML 560, and/or an HBL 575 as a second exciton blocking layer disposed between the EML 560 and the ETL 570.

As described above, the first electrode 510 may be an anode and may include, but are not limited to, a conductive material having a relatively large work function values such as ITO, IZO, SnO, ZnO, ICO, AZO, and the likes. The second electrode 520 may be a cathode and may include, but are not limited to, a conductive material having a relatively small work function values such as Al, Mg, Ca, Ag, alloy thereof or combination thereof.

The HIL 540 is disposed between the first electrode 510 and the HTL 550. The HIL 540 may include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 540 may be omitted in compliance with the structure of the OLED 500.

The HTL 550 is disposed adjacently to the EML 560 between the first electrode 510 and the EML 560. The HTL 550 may include, but are not limited to, aromatic amine compounds such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 560 includes a first EML (EML1) 562, a second EML (EML2) 564 and a third EML (EML3) 566. The EML1 562 is disposed between the EBL 555 and the HBL 575, the EML2 564 is disposed between the EBL 555 and the EML1 562 and the EML3 566 is disposed between the EML1 562 and the HBL 575. The configuration and energy levels among the luminous materials in the EML 560 will be explained in more detail below.

The ETL 570 is disposed between the EML 560 and the EIL 580. In one exemplary embodiment, the ETL 570 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes. As an example, the ETL 570 may include, but are not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 580 is disposed between the second electrode 520 and the ETL 570. In one exemplary embodiment, the EIL 580 may include, but are not limited to, an alkali halide and/or an alkali earth halide such as LiF, CsF, NaF, BaF$_2$ and the likes, and/or an organic metal compound such as lithium benzoate, sodium stearate, and the likes.

The EBL 555 is disposed between the HTL 550 and the EML 560 for controlling and preventing electron transportations between the HTL 550 and the EML 560. As an example, The EBL 555 may include, but are not limited to, TCTA, Tris[4-(diethylamino)phenyl]amine, N-(bipnehyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, 2,8-bis(9-phenyl-9H-carbazol-3-yl)dibenzo[b,d]thiophene and/or 3,6-bis(N-carbazolyl)-N-phenyl-carbazole.

The HBL 575 is disposed between the EML 560 and the ETL 570 for preventing hole transportations between the EML 560 and the ETL 570. In one exemplary embodiment, the HBL 575 may include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 575 may include a compound having a relatively low HOMO energy level compared to the emitting material in EML 560. The HBL 575 may include, but are not limited to, BCP, BAlq, Alq$_3$, PBD, spiro-PBD, Liq, B3PYMPM, DPEPO, 9-(6-(9H-carbazol-9-yl)pyridine-3-yl)-9H-3,9'-bi-carbazole and combination thereof.

The EML1 562 includes a first dopant (T dopant) having a delayed fluorescent property. Each of the EML2 564 and the EML3 566 includes a second dopant (a first fluorescent or phosphorescent dopant, F dopant 1) and a third dopant (a second fluorescent or phosphorescent dopant). Each of the EML1 562, EML2 564 and EML3 566 further includes a first host, a second host and a third host, respectively.

In accordance with this embodiment, the singlet energy as well as the triplet energy of the first dopant, which is the delayed fluorescent material, in the EML1 562 can be transferred to the second and third dopants (the first and second fluorescent or phosphorescent dopants) each of which is included in the EML2 564 and EML3 566 disposed adjacently to the EML1 562 by FRET energy transfer mechanism. Accordingly, the ultimate emission occurs in the second and third dopants in the EML2 564 and the EML3 566.

Figure 10:
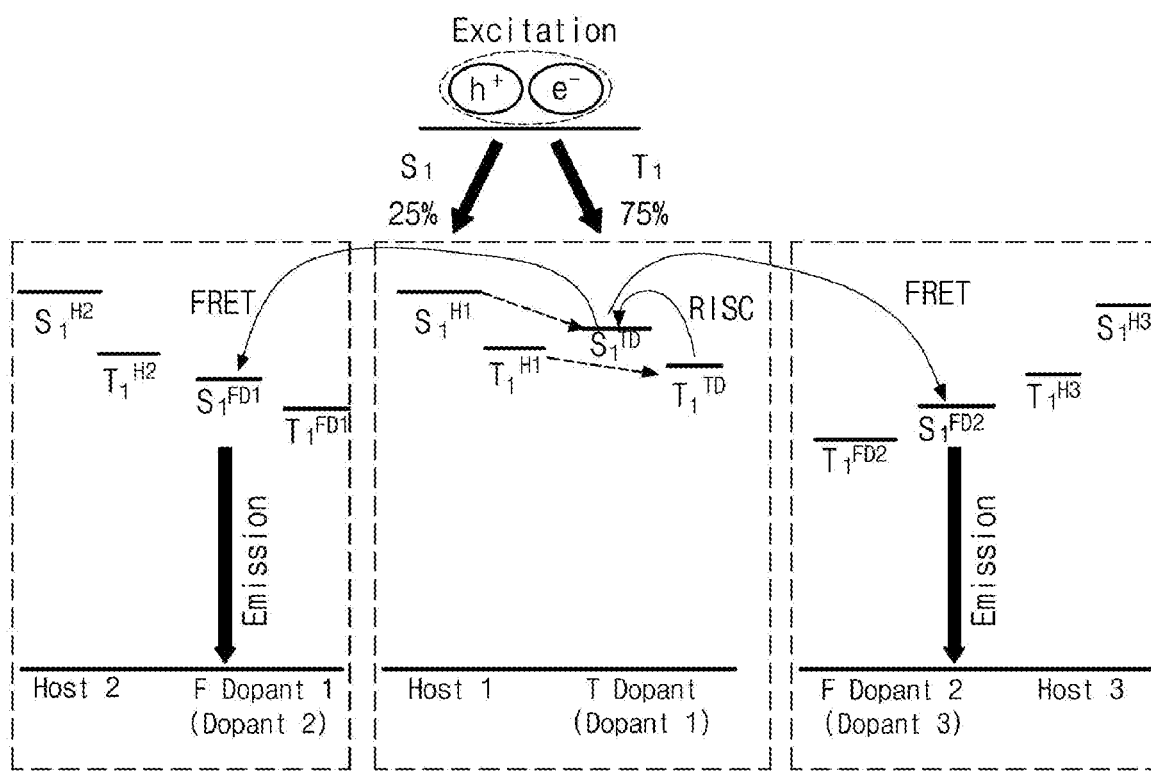
FIG. 10 is a schematic diagram illustrating luminous mechanism by energy level bandgap among luminous materials in accordance with another exemplary embodiment of the present disclosure.

In other words, the triplet exciton energy of the first dopant is converted to the singlet exciton energy of its own in the EML1 562 by RISC mechanism, then the singlet exciton energy of the first dopant is transferred to the singlet exciton energy of the second and third dopants because the excited state singlet energy level $S_1^{TD}$ of the first dopant is higher than the excited state singlet energy levels $S_1^{FD1}$ and $S_1^{FD2}$ of the second and third dopants (See, FIG. 10). The singlet exciton energy of the first dopant in the EML1 562 is transferred to the second and third dopants in the EML2 564 and the EML3 566 which is disposed adjacently to the EML1 562 by FRET mechanism.

The second and third dopants in the EML2 564 and EML3 566 can emit light using the singlet exciton energy and the triplet exciton energy derived from the first dopant. Each of the second and third dopants may have narrower FWHM compared to the first dopant. As the exciton energy, which is generated at the first dopant as the delayed fluorescent material in the EML1 562, is transferred to the second and third dopants in the EML2 564 and the EML3 566, a hyper-fluorescence can be realized. In this case, the first dopant only acts as transferring energy to the second and third dopants. The EML1 562 including the first dopant is not involved in the ultimate emission process. Substantial light emission is occurred in the EML2 564 and in the EML3 566 each of which includes the second dopant and the third dopant with a narrow FWHM. Accordingly, the OLED 500 can enhance its quantum efficiency and improve its color purity due to narrow FWHM. As an example, each of the second and third dopants may have an emission wavelength range having a large overlapping area with an absorption wavelength range of the first dopant.

In this case, it is necessary to adjust properly energy levels among the hosts and the dopants in the EML1 562, the EML2 564 and the EML3 566. FIG. 10 is a schematic diagram illustrating luminous mechanism by energy level bandgap among luminous materials in accordance with another exemplary embodiment of the present disclosure.

As illustrated in FIG. 10, excited state singlet energy levels $S_1^{H1}$, $S_1^{H2}$ and $S_1^{H3}$ and excited state triplet energy levels $T_1^{H1}$, $T_1^{H2}$ and $T_1^{H3}$ of the first to third hosts should be higher than the excited state singlet energy level $S_1^{TD}$ and the excited state triplet energy level $T_1^{TD}$ of the first dopant as the delayed fluorescent material, respectively.

For example, when each of the excited triplet energy levels $T_1^{H1}$, $T_1^{H2}$ and $T_1^{H3}$ of the first to third hosts is not high enough than the excited state triplet energy level $T_1^{TD}$ of the first dopant, the triplet exciton of the first dopant may be reversely transferred to the excited state triplet energy levels $T_1^{H1}$, $T_1^{H2}$ and $T_1^{H3}$ of the first to third hosts, which cannot utilize triplet exciton energy. Accordingly, the excitons of the triplet energy level $T_1^{TD}$ of the first dopant may be quenched as a non-emission and the triplet state excitons of the first dopant cannot be involved in the emission. As an example, each of the excited state triplet energy levels $T_1^{H1}$, $T_1^{H2}$ and $T_1^{H3}$ of the first to third hosts may be higher than the excited state triplet energy level $T_1^{TD}$ of the first dopant by at least about 0.2 eV.

In addition, it is necessary for the EML 560 to implement high luminous efficiency and color purity as well as to transfer exciton energy efficiently from the first dopant, which is converted to ICT complex state by RISC mechanism in the EML1 562, to the second and third dopants each of which is the fluorescent or phosphorescent material in the EML2 564 and the EML3 566. In order to realize such an OLED 500, the excited state triplet energy level $T_1^{TD}$ of the first dopant in the EML1 562 is higher than each of excited state triplet energy levels $T_1^{FD1}$ and $T_1^{FD2}$ of the second and third dopants. In one exemplary embodiment, the excited state singlet energy level $S_1^{TD}$ of the first dopant may be higher than each of excited state singlet energy levels $S_1^{FD1}$ and $S_1^{FD2}$ of the second and third dopants as fluorescent material.

Moreover, the exciton energy, which is transferred from the first dopant to each of the second and third dopants, should not be transferred to the second and third hosts in order to realize efficient light emission. As an example, each of the excited singlet energy levels $S_1^{H2}$ and $S_1^{H3}$ of the second and third hosts may be higher than each of the excited state singlet energy level $S_1^{FD1}$ and $S_1^{FD2}$ of the second and third dopants, respectively. In one exemplary embodiment, the energy level bandgap between the excited state singlet energy level $S_1^{TD}$ and the excited state triplet energy level $T_1^{TD}$ of the first dopant may be equal to or less than about 0.3 eV in order to implement a delayed fluorescence.

In addition, an energy level bandgap ($|HOMO^H-HOMO^{TD}|$) between a HOMO energy level ($HOMO^H$) of the first to third hosts and a HOMO energy level ($HOMO^{TD}$) of the first dopant, or an energy level bandgap ($|LUMO^H-LUMO^{TD}|$) between a LUMO energy level ($LUMO^H$) of the first to third hosts and a LUMO energy level ($LUMO^{TD}$) of the first dopant may be equal to or less than about 0.5 eV.

Each of the EML1 562, the EML2 564 and the EML3 566 may include the first host, the second host and the third host, respectively. For example, each of the first to third hosts may be the same or different from each other. For Example, each of the first to third hosts may independently include the organic compound having the structure of any one in Chemical Formulae 1 to 6. In one exemplary embodiment, the first dopant may include, but are not limited to, the organic compound having the structure of any one in Chemical Formula 7. In an alternative embodiment, the first dopant may include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

Each of the second and third dopants may have narrow FWHM and have luminous spectrum having large overlapping area with the absorption spectrum of the first dopant. As an example, each of the second and third dopants may independently include, but are not limited to, an organic compound having a quinolino-acridine core such as 5,12-dimethylquinolino[2,3-b]acridine-7,14(5H, 12H)-dione, 12-diethylquinolino[2,3-b]acridine-7,14(5H, 12H)-dione, 5,12-dibutyl-3,10-difluoroquinolino[2,3-b]acridine-7,14 (5H, 12H)-dione, 5,12-dibutyl-3,10-bis(trifluoromethyl)quinolino[2,3-b]acridine-7,14(5H, 12H)-dione, 5,12-dibutyl-2, 3,9,10-tetrafluoroquinolino[2,3-b]acridine-7,14(5H, 12H)-dione, DCJTB and any metal complexes which can emit light of red, green or blue color.

In one exemplary embodiment, each of the second and third hosts in the EML2 564 and the EML3 566 may have weigh ratio equal to or more than the weight ratio of the second and third dopants within the same EMLs. The weight ratio of the first dopant in the EML1 562 may be more than the weight ratio of the second and third dopants in the EML2 564 and the EML3 566. In this case, it is possible to transfer enough exciton energy from the first dopant in the EML1 562 to the second and third dopants in the EML2 564 and the EML3 566 through FRET energy transfer mechanism.

As an example, the EML1 562 may include the first dopant of about 1 to about 70% by weight, preferably about 10 to about 50% by weight, and more preferably about 20 to about 50% by weight. Each weight ratio of the second and thirds hosts may be larger than each weight ratio of the second and third dopants in the EML2 564 and the EML3 566. As an example, each of the EML2 564 and EML3 566 may include the second or third host, but are not limited to, about 90 to about 99% by weight, and preferably about 95 to about 99% by weight, and the second or third dopant, but are not limited to, about 1 to about 10% by weight, and preferably about 1 to about 5% by weight.

The EML1 562 may be laminated with a thickness of, but are not limited to, about 2 to about 100 nm, preferably about 2 to about 30 nm, and preferably about 2 to about 20 nm. Each of the EML2 564 and the EML3 566 may be laminated with a thickness of, but are not limited to, about 5 to about 100 nm, preferably about 10 to about 30 nm, and more preferably about 10 to about 20 nm.

When the EML2 564 is disposed adjacently to the EBL 555 in one exemplary embodiment, the second host, which is included in the EML2 564 together with the second dopant, may be the same material as the EBL 555. In this case, the EML2 564 may have an electron blocking function as well as an emission function. In other words, the EML2

564 can act as a buffer layer for blocking electrons. In one embodiment, the EBL 555 may be omitted where the EML2 564 may be an electron blocking layer as well as an emitting material layer.

When the EML3 566 is disposed adjacently to the HBL 575 in another exemplary embodiment, the third host, which is included in the EML3 566 together with the third dopant, may be the same material as the HBL 575. In this case, the EML3 566 may have a hole blocking function as well as an emission function. In other words, the EML3 566 can act as a buffer layer for blocking holes. In one embodiment, the HBL 575 may be omitted where the EML3 566 may be a hole blocking layer as well as an emitting material layer.

In still another exemplary embodiment, the second host in the EML2 564 may be the same material as the EBL 555 and the third host in the EML3 566 may be the same material as the HBL 575. In this embodiment, the EML2 564 may have an electron blocking function as well as an emission function, and the EML3 566 may have a hole blocking function as well as an emission function. In other words, each of the EML2 564 and the EML3 566 can act as a buffer layer for blocking electrons or hole, respectively. In one embodiment, the EBL 555 and the HBL 575 may be omitted where the EML2 564 may be an electron blocking layer as well as an emitting layer and the EML3 566 may be a hole blocking layer as well as an emitting material layer.

Figure 11:
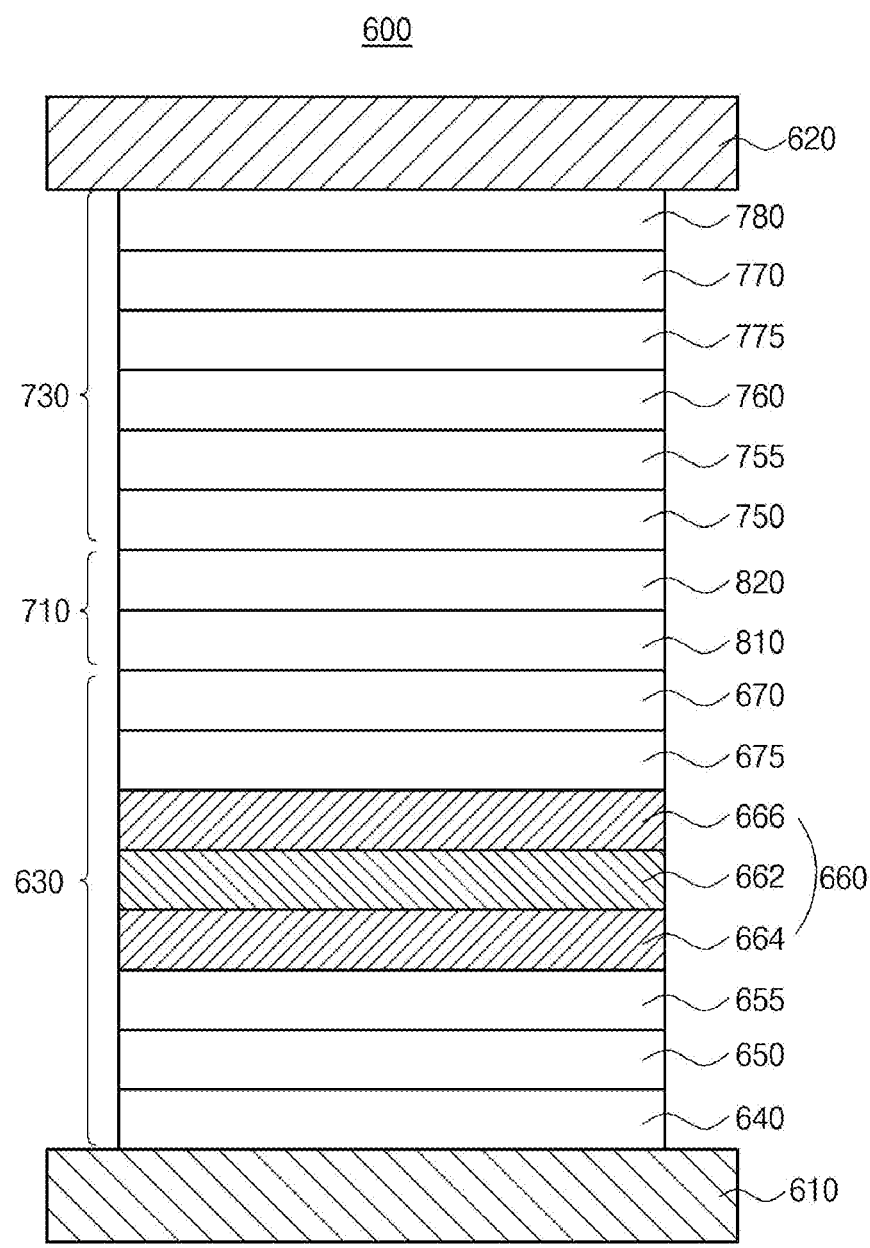
FIG. 11 is a schematic cross-section view illustrating an organic light emitting diode in accordance with another exemplary embodiment of the present disclosure.

In the above embodiments, the OLED having only one emitting unit is described. Unlike the above embodiment, the OLED may have multiple emitting units so as to form a tandem structure. FIG. 11 is a cross-sectional view illustrating an organic light emitting diode in accordance with still another embodiment of the present disclosure.

As illustrated in FIG. 11, the OLED 600 in accordance with the fifth embodiment of the present disclosure includes first and second electrodes 610 and 620 facing each other, a first emitting unit 630 as a first emission layer disposed between the first and second electrodes 610 and 620, a second emitting unit 730 as a second emission layer disposed between the first emitting unit 630 and the second electrode 620, and a charge generation layer 710 disposed between the first and second emitting units 630 and 730.

As mentioned above, the first electrode 610 may be an anode and include, but are not limited to, a conductive material having a relatively large work function values. As an example, the first electrode 610 may include, but are not limited to, ITO, IZO, SnO, ZnO, ICO, AZO, and the likes. The second electrode 620 may be a cathode and may include, but are not limited to, a conductive material having a relatively small work function values such as Al, Mg, Ca, Ag, alloy thereof or combination thereof. Each of the first and second electrodes 610 and 620 may be laminated with a thickness of, but are not limited to, about 30 to about 300 nm.

The first emitting unit 630 includes a HIL 640, a first HTL (a lower HTL) 650, a lower EML 660 and a first ETL (a lower ETL) 670. The first emitting unit 630 may further include a first EBL (a lower EBL) 655 disposed between the first HTL 650 and the lower EML 660 and/or a first HBL (a lower HBL) 675 disposed between the lower EML 660 and the first ETL 670.

The second emitting unit 730 includes a second HTL (an upper HTL) 750, an upper EML 760, a second ETL (an upper ETL) 770 and an EIL 780. The second emitting unit 730 may further include a second EBL (an upper EBL) 755 disposed between the second HTL 750 and the upper EML 760 and/or a second HBL (an upper HBL) 775 disposed between the upper EML 760 and the second ETL 770.

At least one of the lower EML 660 and the upper EML 760 may include the organic compound having the structure of any one in Chemical Formulae 1 to 6 and emit green (G) light. As an example, one of the lower and upper EMLs 660 and 760 may emit green (G) light, and the other of the lower and upper EMLs 660 and 760 may emit blue (B) and/or red (R) light. Alternatively, one of the lower and upper EMLs 660 and 760 may emit blue (B) light and the other of the lower and upper EMLs 660 and 760 may emit green (G), red (R), red-green (RG) or yellow-green (YG). Hereinafter, the OLED 600, where the lower EML 660 emits green light and includes the organic compound having the structure of any one in Chemical Formulae 1 to 6 and the upper EML 760 emits blue and/or red lights, will be explained.

The HIL 640 is disposed between the first electrode 610 and the first HTL 650 and improves an interface property between the inorganic first electrode 610 and the organic first HTL 650. In one exemplary embodiment, the HIL 640 may include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 640 may be omitted in compliance with a structure of the OLED 600.

Each of the first and second HTLs 650 and 750 may independently include, but are not limited to, TPD, NPD (NPB), CBP, poly-TPD, TFB, TAPC, N-(biphenyl-4-yl)-9, 9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine. Each of the HIL 640 and the first and second HTLs 650 and 750 may be laminated with a thickness of, but are not limited to, about 5 to about 200 nm, and preferably about 5 to about 100 nm.

Each of the first and second ETLs 670 and 770 facilitates electron transportations in the first emitting unit 630 and the second emitting unit 730, respectively. Each of the first and second ETLs 670 and 770 may independently include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes, respectively. As an example, each of the first and second ETLs 670 and 770 may independently include, but are not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ, respectively.

The EIL 780 is disposed between the second electrode 620 and the second ETL 770, and can improve physical properties of the second electrode 620 and therefore, can enhance the life span of the OLED 600. In one exemplary embodiment, the EIL 780 may include, but are not limited to, an alkali halide and/or an alkali earth halide such as LiF, CsF, NaF, $BaF_2$ and the likes, and/or an organic metal compound such as lithium benzoate, sodium stearate, and the likes.

As an example, each of the first and second EBLs 655 and 755 may independently include, but are not limited to, TCTA, Tris[4-(diethylamino)phenyl]amine, N-(bipnehyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, 2,8-bis(9-phenyl-9H-carbazol-3-yl)dibenzo[b,d]thiophene and/or 3,6-bis(N-carbazolyl)-N-phenyl-carbazole, respectively.

Each of the first and second HBLs 675 and 775 may independently include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, each of the first and second HBLs 675 and 775 may independently include, but are not limited to, BCP, BAlq, Alq$_3$, PBD, spiro-PBD, Liq, B3PYMPM, DPEPO, 9-(6-(9H-carbazol-9-yl)pyridine-3-yl)-9H-3,9'-bicarbazole and combination thereof, respectively.

In one exemplary embodiment, when the upper EML 760 emits red light, the upper EML 760 may be, but are not limited to a phosphorescent material layer including a host such as CBP and the likes and at least one dopant selected from the group consisting of PIQIr(acac) (bis(1-phenylisoquinoline)acetylacetonate iridium), PQIr(acac) (bis(1-phenylquinoline)acetylacetonate iridium), PQIr (tris(1-phenylquinoline)iridium) and PtOEP(octaethylporphyrin platinum). Alternatively, the upper EML 760 may be a fluorescent material layer including PBD:Eu(DMB)3(phen), perylene and/or their derivatives. In this case, the upper EML 760 may emit red light having, but are not limited to, emission wavelength ranges of about 600 nm to about 650 nm.

In another exemplary embodiment, when the upper EML 760 emits blue light, the upper EML 760 may be, but are not limited to, a phosphorescent material layer including a host such as CBP and the likes and at least one iridium-based dopant. Alternatively, the upper EML 760 may be a fluorescent material layer including any one selected from the group consisting of spiro-DPVBi, spiro-CBP, distrylbenzene (DSB), distrylarylene (DSA), PFO-based polymers and PPV-based polymers. The upper EML 760 may emit light of sky-blue color or deep blue color as well as blue color. In this case, the upper EML 760 may emit red light having, but are not limited to, emission wavelength ranges of about 440 nm to about 480 nm.

In one exemplary embodiment, the second emitting unit 730 may have double-layered EML 760, for example, a blue emitting material layer and a red emitting material layer, in order to enhance luminous efficiency of the red light. In this case, the upper EML 760 may emit light having, but are not limited to, emission wavelength ranges of about 440 nm to about 650 nm.

The charge generation layer (CGL) 710 is disposed between the first emitting unit 630 and the second emitting unit 730. The CGL 710 include an N-type CGL 810 disposed adjacently to the first emitting unit 630 and a P-type CGL 820 disposed adjacently to the second emitting unit 730. The N-type CGL 810 injects electrons into the first emitting unit 630 and the P-type CGL 820 injects holes into the second emitting unit 730.

As an example, the N-type CGL 810 may be a layer doped with an alkali metal such as Li, Na, K and/or Cs and/or an alkaline earth metal such as Mg, Sr, Ba and/or Ra. For example, a host used in the N-type CGL 810 may include, but are not limited to, an organic compound such as Bphen or MTDATA. The alkali metal or the alkaline earth metal may be doped by about 0.01 wt % to about 30 wt %.

The P-type CGL 820 may include, but are not limited to, an inorganic material selected from the group consisting of tungsten oxide (WO$_x$), molybdenum oxide (MoO$_x$), beryllium oxide (Be$_2$O$_3$), vanadium oxide (V$_2$O$_5$) and combination thereof, and/or an organic material selected from the group consisting of NPD, HAT-CN, 2,3,5,6-Tetrafluoro-7,7,8,8-tetracyanoquinodimethane (F4TCNQ), TPD, N,N,N',N'-Tetranaphthalenyl-benzidine (TNB), TCTA, N,N'-dioctyl-3,4,9,10-perylenedicarboximide (PTCDI-C8) and combination thereof.

The lower EML 660 includes a first EML (EML1) 662 disposed between the first EBL 655 and the first HBL 675, a second EML (EML2) 664 disposed between the first EBL 655 and the EML1 662 and a third EML (EML3) 666 disposed between the EML1 662 and the first HBL 675. The EML1 662 includes a first dopant (T dopant) which is a delayed fluorescent material. Each of the EML2 664 and the EML3 666 includes a second dopant (a first F dopant) and a third dopant (a second F dopant) each of which is a fluorescent or phosphorescent material, respectively. Each of the EML1 662, the EML2 664 and the EML3 666 includes a first host, a second host and a third host, respectively.

In this case, the singlet exciton energy as well as the triplet exciton energy of the first dopant in the EML1 662 can be transferred to the second and third dopants each of which is included in the EML2 664 and EML3 666 disposed adjacently to the EML1 662 by FRET energy transfer mechanism. Accordingly, the ultimate emission occurs in the second and third dopants in the EML2 664 and the EML3 666.

In other words, the triplet exciton energy of the first dopant is converted to the singlet exciton energy of its own in the EML1 662 by RISC mechanism, then the singlet exciton energy of the first dopant is transferred to the singlet exciton energy of the second and third dopants because the excited state singlet energy level $S_1^{TD}$ of the first fluorescent dopant is higher than each of the excited state singlet energy levels $S_1^{FD1}$ and $S_1^{FD2}$ of the second and third dopants (See, FIG. 10).

The second and third dopants in the EML2 664 and EML3 666 can emit light using the singlet exciton energy and the triplet exciton energy derived from the first dopant. Since the second and third dopants have relatively narrow FWHM as compared with the first dopant, the OLED 600 can enhance its luminous efficiency and color purity.

Each of the EML1 662, the EML2 664 and the EML3 666 includes the first host, the second host and the third host, respectively. For example, each of the first to third hosts may be the same or different from each other. As an example, each of the first to third hosts may include the organic compound having the structure of any one in Chemical Formulae 1 to 6. In one exemplary embodiment, the first dopant may include, but are not limited to, the organic compound having the structure of any one in Chemical Formula 7. In an alternative embodiment, the first dopant may include, but are not limited to, DMAC-TRZ, DMAC-DPS, ACRSA, Cz-VPN, TcZTrz, DczTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 10-(4-(4,6-diphenyl-1,3,5-triazin-2-yl)phenyl)-10H-spiro[acridine-9,9'-xanthene] and/or SpiroAC-TRZ.

Each of the second and third dopants may have narrow FWHM and have luminous spectrum having large overlapping area with the absorption spectrum of the first dopant. As an example, each of the second and third dopants may independently include, but are not limited to, an organic compound having a quinolino-acridine core such as 5,12-dimethylquinolino[2,3-b]acridine-7,14(5H, 12H)-dione, 12-diethylquinolino[2,3-b]acridine-7,14(5H, 12H)-dione, 5,12-dibutyl-3,10-difluoroquinolino[2,3-b]acridine-7,14 (5H, 12H)-dione, 5,12-dibutyl-3,10-bis(trifluoromethyl)quinolino[2,3-b]acridine-7,14(5H, 12H)-dione, 5,12-dibutyl-2,3,9,10-tetrafluoroquinolino[2,3-b]acridine-7,14(5H, 12H)-dione, DCJTB and any metal complexes which can emit light of red, green or blue color.

In this case, the energy levels among the first to third hosts and the first to third dopant are the same as described in FIG. 10.

In one exemplary embodiment, each of the second and third hosts in the EML2 664 and the EML3 666 may have weigh ratio equal to or more than the weight ratio of the second and third dopants within the same EMLs. The weight ratio of the first dopant in the EML1 662 may be more than the weight ratio of the second and third dopants in the EML2 664 and the EML3 666. In this case, it is possible to transfer enough exciton energy from the first dopant in the EML1 662 to the second and third dopants in the EML2 664 and the EML3 666 through FRET energy transfer mechanism.

When the EML2 664 is disposed adjacently to the first EBL 655 in one exemplary embodiment, the second host, which is included in the EML2 664 together with the second dopant, may be the same material as the first EBL 655. In this case, the EML2 664 may have an electron blocking function as well as an emission function. In other words, the EML2 664 can act as a buffer layer for blocking electrons. In one embodiment, the first EBL 655 may be omitted where the EML2 664 may be an electron blocking layer as well as an emitting material layer.

When the EML3 666 is disposed adjacently to the first HBL 675 in another exemplary embodiment, the third host, which is included in the EML3 666 together with the third dopant, may be the same material as the first HBL 675. In this case, the EML3 666 may have a hole blocking function as well as an emission function. In other words, the EML3 666 can act as a buffer layer for blocking holes. In one embodiment, the first HBL 675 may be omitted where the EML3 666 may be a hole blocking layer as well as an emitting material layer.

In still another exemplary embodiment, the second host in the EML2 664 may be the same material as the first EBL 655 and the third host in the EML3 666 may be the same material as the first HBL 675. In this embodiment, the EML2 664 may have an electron blocking function as well as an emission function, and the EML3 666 may have a hole blocking function as well as an emission function. In other words, each of the EML2 664 and the EML3 666 can act as a buffer layer for blocking electrons or hole, respectively. In one embodiment, the first EBL 655 and the first HBL 675 may be omitted where the EML2 664 may be an electron blocking layer as well as an emitting layer and the EML3 666 may be a hole blocking layer as well as an emitting material layer.

In an alternative embodiment, the lower EML 660 may have a single-layered structure as illustrated in FIGS. 2 and 5. In this case, the lower EML 660 may include a host and a first dopant which may be a delayed fluorescent material, or a host, a first dopant which may be a delayed fluorescent material and a second dopant which may be a fluorescent or phosphorescent material.

In another alternative embodiment, the lower EML 660 may have a double-layered structure as illustrated in FIG. 7. In this case, the lower EML 660 may include a first EML and a second EML. The first EML may include a first host and a first dopant which may be a delayed fluorescent material, and the second EML may include a second host and a second dopant which may be a fluorescent or phosphorescent material.

In another exemplary embodiment, an OLED of the present disclosure may further includes a third emitting unit disposed between the second emitting unit 730 and the second electrode 620 and a second CGL disposed between the second emitting unit 730 and the third emitting unit. In this case, at least one of the first emitting unit 630, the second emitting unit 730 and the third emitting unit may include the organic compound having the structure of any one in Chemical Formulae 1 to 6 as the host.

Synthesis Example 1: Synthesis of Compound 1

(1) Synthesis of Intermediate 1-1 (Methyl-2-(pyridin-3-yl-amino) benzoate)

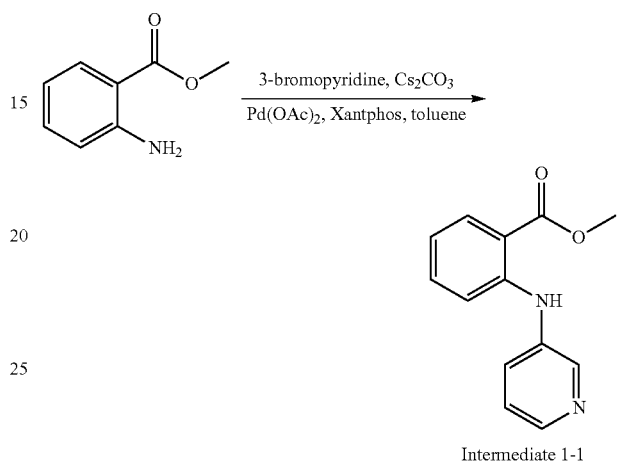

Intermediate 1-1

5.30 g (35 mmol) of methyl-2-aminobenzoate, 5.0 g (32 mmol) of 3-bromopyridine, 14.3 g (44 mmol) of $Cs_2CO_3$ and 50 mL of toluene was placed into 250 mL three neck distillation round bottom flask and then nitrogen was substituted. 0.072 g (0.32 mmol) of palladium (II) acetate ($Pd(OAc)_2$) and 0.56 g (0.96 mmol) of 4,5-bis(diphenylphosphine)-9,9-dimehtylxanthene (Xantphos) were added into the nitrogen substituted flask and then the solution was stirred for 12 hours at 110° C. The proceeding status of the reaction was confirmed using TLC (thin layer chromatography) and then the flask was cooled down to room temperature. After salts produced in the course of the reaction and excessive $Cs_2CO_3$ were removed by Celite filter, the filtrate was distilled under reduced pressure and then was purified by solid column chromatography. The solvent was removed to give 4.5 g (yield: 66%) of yellow solid intermediate 1-1.

(2) Synthesis of Intermediate 1-2 (Diphenyl-(2-pyridin-3-yl-amino)-phenyl) methanol)

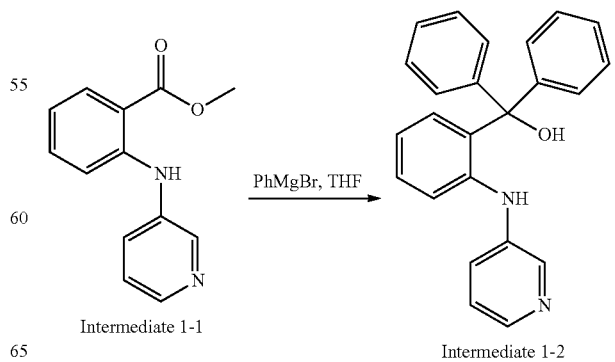

Intermediate 1-1    Intermediate 1-2

2.0 g (8.7 mmol) of intermediate 1-1 and 25 mL of THF were placed into 100 mL three neck distillation round bottom flask and then nitrogen was substituted. Phenylmagnesium bromide (26 mmol) was added drop wisely to the flask at 0° C. with stirring. After dropping was completed, the solution was stirred for 12 hours at room temperature. The proceeding status of the reaction was confirmed using TLC. After reactants were distilled under reduced pressure and then was purified by solid column chromatography. The solvent was removed to give 2.8 g (yield: 91%) of yellow solid intermediate 1-2.

(3) Synthesis of Intermediate 1-3 (5,5-Diphenyl-5,10-dihydrobenzo[1,7]naphthyridine)

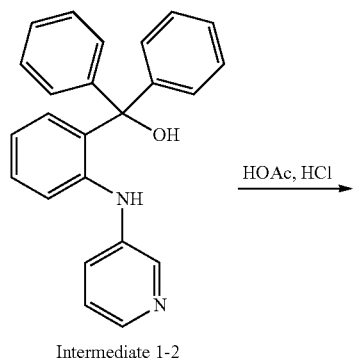

Intermediate 1-2

2.8 g (7.9 mmol) of intermediate 1-2, 40 mL of acetic acid and 4 mL of HCl were placed into 250 mL three neck distillation round bottom flask, and then the solution was stirred for 12 hours at 70° C. The solid produced in the course of the reaction was obtained by reduced filter and then was purified by solid column chromatography. The solvent was removed and a crude product was recrystallized using methylene chloride (MC) and hexane to give 2.3 g (yield: 86%) of yellow solid intermediate 1-3.

(4) Synthesis of Intermediate 1-4 (9-(3-Bromophenyl)-9H-carbazole)

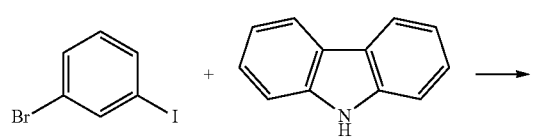

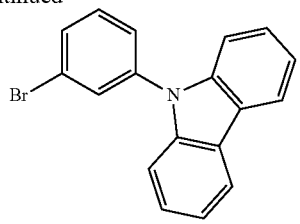

Intermediate 1-4

145 mL (53 mmol) of 1-bromo-3-iodo benzene, 8.7 g (52 mmol) of carbazole, 10.1 g (159 mmol) of Cu powder, 22 g (159 mmol) of $K_2CO_3$ and 150 mL of DMF were placed into 250 mL three neck distillation round bottom flask, and then the solution was stirred for 24 hours at 130° C. The proceeding status of the reaction was confirmed using TLC and then the flask was cooled down to room temperature. After salts produced in the course of the reaction and excessive $K_2CO_3$ were removed by Celite filter, the solution was extracted with 20 mL of distilled water and 150 mL (×3) of EtOAc. The organic solution was dried by $MgSO_4$ and then distilled under reduced pressure to obtain solid mixture. The solid mixture was purified by silica column chromatography to give 14.9 g (yield: 89%) of intermediate 1-4.

(5) Synthesis of Compound 1 (10-(3-(9H-carbazol-9-yl)phenyl)-5,5-diphenyl-5,10-dihydrobenzo[b][1,7]naphthyridine)

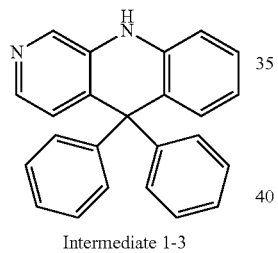

Compound 1

1.61 g (5 mmol) of intermediate 1-4, 1.5 g (4.5 mmol) of intermediate 1-3, 1.12 g (10 mmol) of potassium tert-butoxide (t-BuOK) and 40 mL of toluene were placed into 100 mL three neck distillation round bottom flask, and then nitrogen was substituted. 0.22 g (0.23 mmol) of tris(dibenzylideneacetone) dipalladium (0) (Pd$_2$(dba)$_3$) and 0.18 g (0.9 mmol) of tri-tert-butylphosphine (P(tBu)$_3$) were placed into the nitrogen substituted flask, and then the solution was stirred for 12 hours. The proceeding status of the reaction was confirmed using TLC and then the flask was cooled down to room temperature. After salts produced in the course of the reaction and excessive t-BuOK were removed by Celite filter, the filtrate was distilled under reduced pressure and then was purified by solid column chromatography. The solvent was removed and a crude product was recrystallized using methylene chloride and hexane to give 1.7 g (yield: 66%) of white solid Compound 1.

Synthesis Example 2: Synthesis of Compound 2

(1) Synthesis of Intermediate 2-1 (9-(4-bromophenyl)-9H-carbazole)

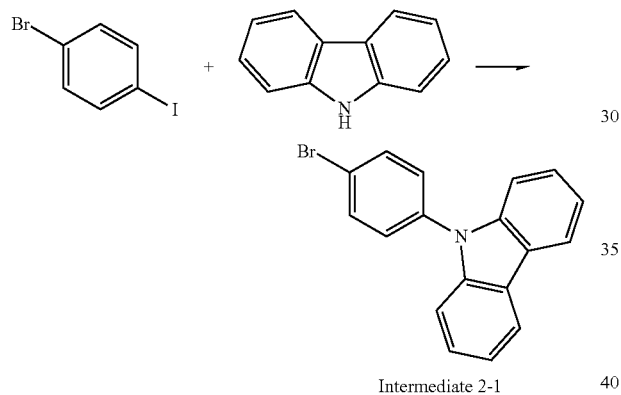

Intermediate 2-1

Synthetic process was performed in the same manner as in the synthesis of the intermediate 1-4 except that 145 mL (53 mmol) of 1-bromo-4-iodobenzene and 8.7 g (52 mmol) of carbazole were used as reactants to give 6.2 g (yield: 52%) of Intermediate 2-1.

(2) Synthesis of Compound 2 (10-(4-(9H-carbazol-9-yl)phenyl)-5,10-dihydro-5,5-diphenylbenzo[b][1,7]naphthyridine)

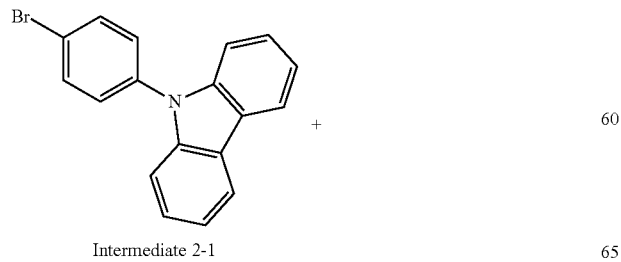

Intermediate 2-1

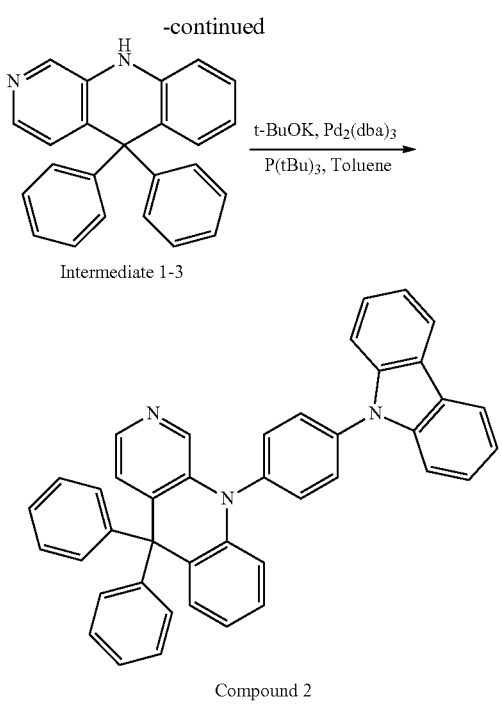

Intermediate 1-3

Compound 2

Synthetic process was performed in the same manner as in the synthesis of the Compound 1 except that 0.7 g (1.4 mmol) of intermediate 2-1 and 0.52 g (1.5 mmol) of intermediate 1-3 were used as reactants to give 0.6 g (yield: 75%) of white solid Compound 2.

Synthesis Example 3: Synthesis of Compound 3

(1) Synthesis of Intermediate 3-1 (10-(3-bromophenyl)-9,9-diphenyl-9,10-dihydroacridine)

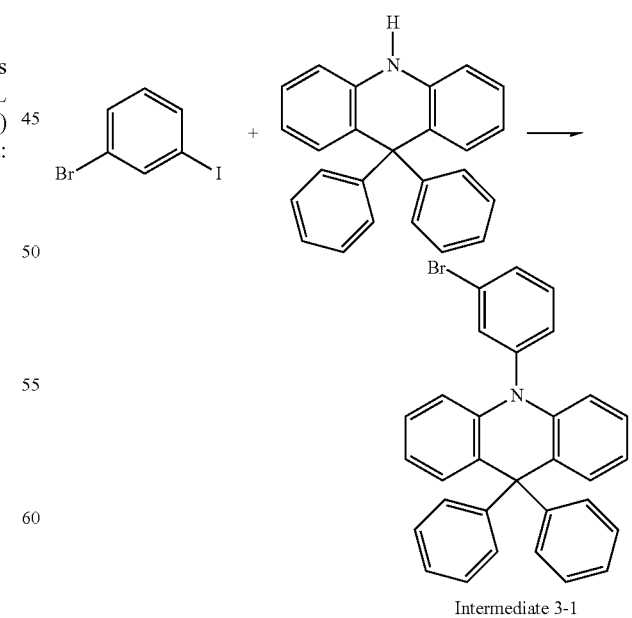

Intermediate 3-1

12 g (43 mmol) of 1-bromo-3-iodobenzene, 12 g (36 mmol) of diphenylacridine, 0.343 g (1.8 mmol) of CuI, 6.92 g (72.0 mmol) of sodium tert-butoxide (NaOt-Bu), 0.822 g (7.20 mmol) of tert-1,2-diaminocyclohexane and 150 mL of 1,4-dioxane were placed into 250 mL three neck distillation round bottom flask, and then the solution was stirred for 12 hours at 100° C. The reaction mixture was cooled down to room temperature, 100 mL of methanol was added into the solution, and then the solution was distilled under reduced pressure to recover a precipitate. The precipitated reaction mixture was purified by silica column chromatography to give 10.1 g (yield: 58%) of intermediate 3-1.

(2) Synthesis of Compound 3 (10-(3-(9,9-diphenylacridin-10(9H)-yl)phenyl)-5,5-diphenyl-5,10-dihydrobenzo[b][1,7]naphthyridine)

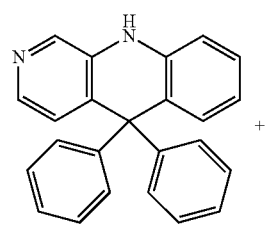

Intermediate 1-3

+

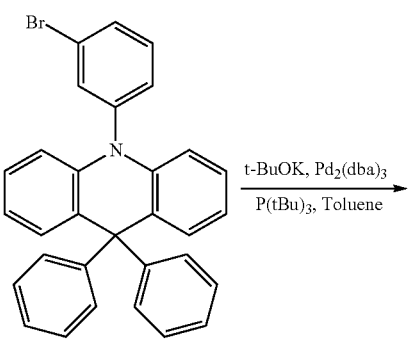

Intermediate 3-1

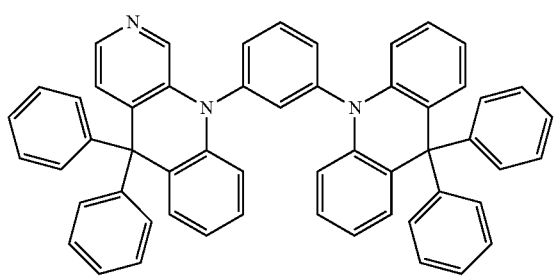

Compound 3

Synthetic process was performed in the same manner as in the synthesis of the Compound 1 except that 0.7 g (1.4 mmol) of intermediate 3-1 and 0.52 g (1.5 mmol) of intermediate 1-3 were used as reactants to give 0.8 g (yield: 78%) of white solid Compound 3.

Synthesis Example 4: Synthesis of Compound 4

(1) Synthesis of Intermediate 4-1 (10-(4-bromophenyl)-9,9-diphenyl-9,10-dihydroacridine)

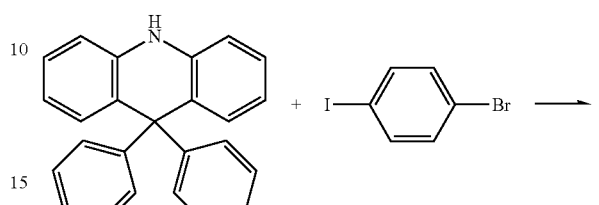

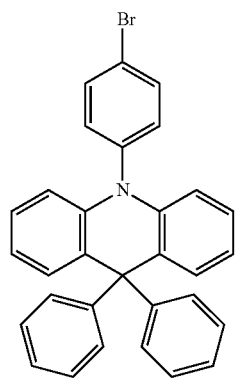

Intermediate 4-1

Synthetic process was performed in the same manner as in the synthesis of the intermediate 3-1 except that 7.6 g (36 mmol) of diphenylacridine and 36 g (127 mmol) of 1-bromo-4-iodobenzene were used as reactants to give 11 g (yield: 80%) f intermediate 4-1.

(2) Synthesis of Compound 4 (5,10-dihydro-5,5-diphenyl-10-(4-(9,9-diphenylacridin-10(9H)-yl)phenyl)benzo[b][1,7]naphthyridine)

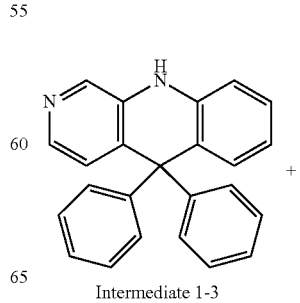

Intermediate 1-3

+

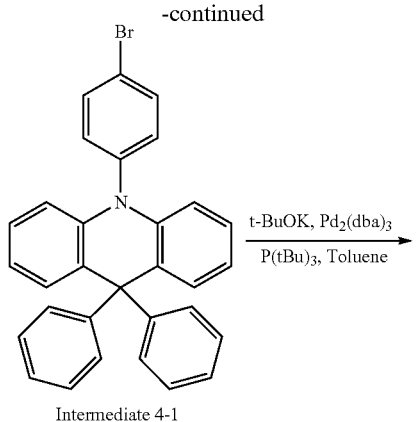

Intermediate 4-1

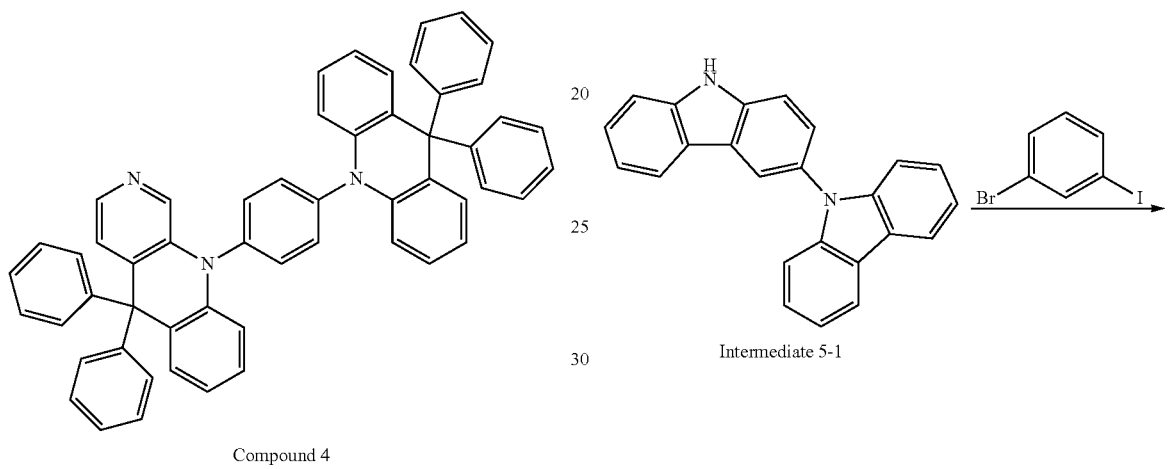

Compound 4

Synthetic process was performed in the same manner as in the synthesis of the Compound 1 except that 0.7 g (1.4 mmol) of intermediate 4-1 and 0.52 g (1.5 mmol) of intermediate 1-3 were used as reactants to give 0.85 g (yield: 85%) of white solid Compound 4.

Synthesis Example 5: Synthesis of Compound 5

(1) Synthesis of Intermediate 5-1 (3-(9H-carbazol-9-yl)-9H-carbazole)

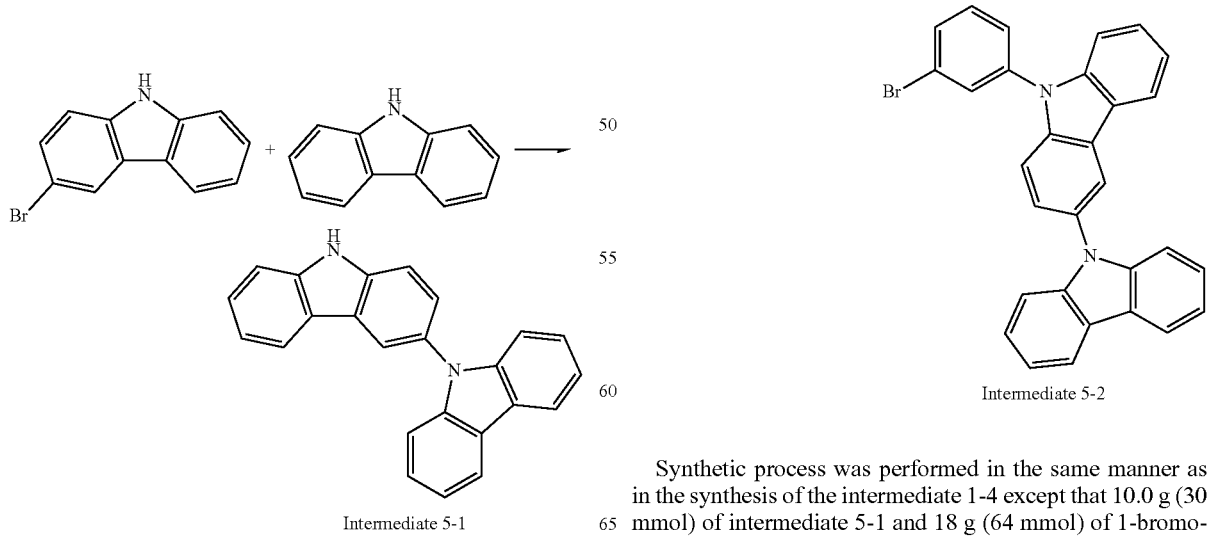

Intermediate 5-1

35.3 g (143.5 mmol) of 3-bromo-carbazole, 20 g (119.6 mmol) of carbazole, 60 g (60 mmol) of CuI, 97.4 g (229 mmol) of $Cs_2CO_3$ and 7.18 g (119.6 mmol) of ethylene diamine were dissolved in 700 mL of toluene, the solution was refluxed for 12 hours and then the solution was cooled down to room temperature. After the solution was extracted with 150 mL (×4) of EtOAc, the moisture of the organic layer was dried by $MgSO_4$. The organic solvent was removed and then a crude product was purified by silica tube chromatography to give 33 g (yield: 80%) of intermediate 5-1.

(2) Synthesis of Intermediate 5-2 (9-(9-(3-bromophenyl)-9H-carbazol-6-yl)-9H-carbazole)

Intermediate 5-2

Synthetic process was performed in the same manner as in the synthesis of the intermediate 1-4 except that 10.0 g (30 mmol) of intermediate 5-1 and 18 g (64 mmol) of 1-bromo-3-iodobenzene were used as reactants to give 12.1 g (yield: 83%) of intermediate 5-2.

(3) Synthesis of Compound 5 (10-(3-(9H-carbazol-9-yl)phenyl)-5,5-diphenyl-5,10-dihydrobenzo[b][1,7]naphthyridine)

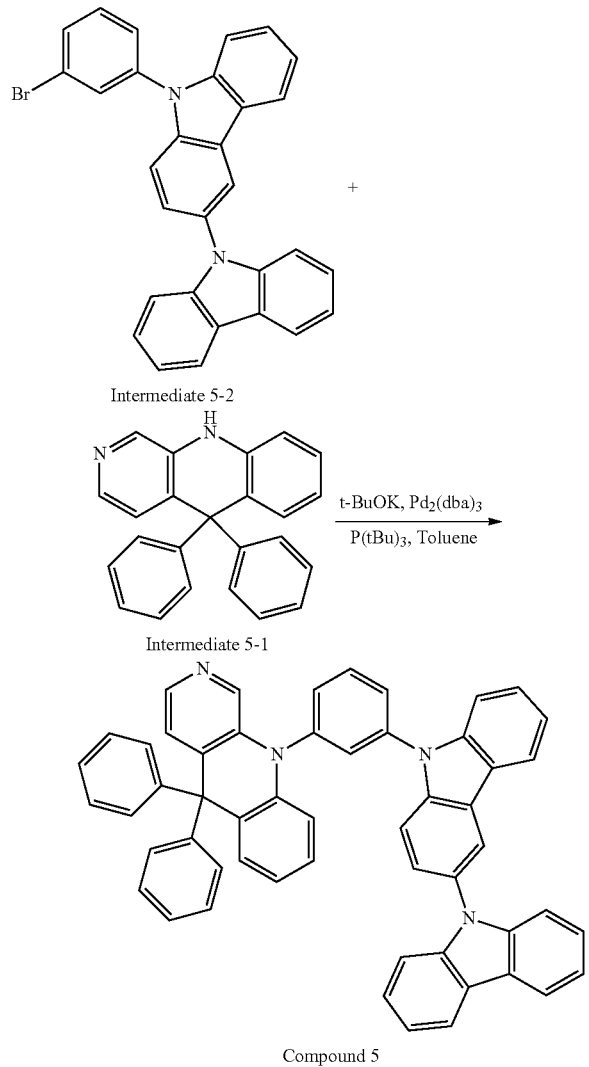

Synthetic process was performed in the same manner as in the synthesis of the Compound 1 except that 2.04 g (5 mmol) of intermediate 5-2 and 1.5 g (4.5 mmol) of intermediate 1-3 were used as reactants to give 2.0 g (yield: 60%) of white solid Compound 5.

Synthesis Example 6: Synthesis of Compound 6

(1) Synthesis of Intermediate 6-1 (9-(3-bromo-5-(9H-carbazol-9-yl)phenyl)-9H-carbazole)

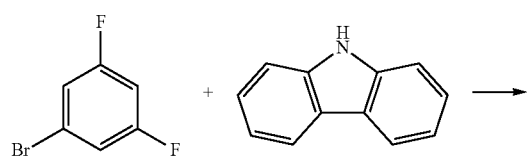

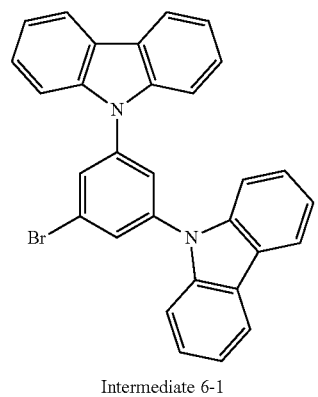

Intermediate 6-1

52 g (0.31 mmol) of carbazole and 13 g (0.31 mmol) of NaH (60% suspension in oil) were dispersed in 250 mL of anhydrous DMF and then the dispersion was stirred for 1 hour at room temperature. 12 mL (0.10 mol) of 3,5-difluorobromobenzene was added slowly into the dispersion using dropping funnel, and the solution was stirred for 12 hours at 130° C. The reaction solution was cooled down to room temperature and then mixed solution of EtOH/H$_2$O (10/1) was added to form a precipitate. The precipitated product was recrystallized by methylene chloride and methanol to give 39.3 g (yield: 81%) of intermediate 6-1.

(2) Synthesis of Compound 6 (10-(3,5-di(9H-carbazol-9-yl)phenyl)-5,10-dihydro-5,5-diphenylbenzo[b][1,7]naphthyridine)

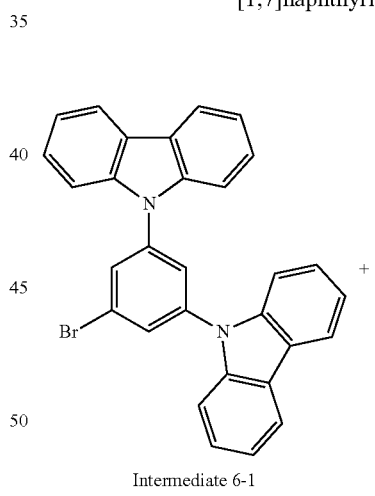

Intermediate 6-1

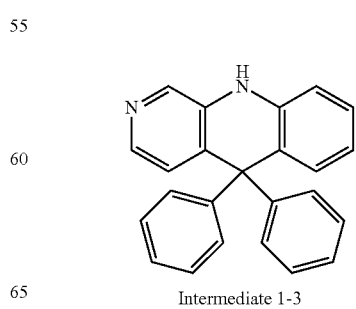

Intermediate 1-3

Compound 6

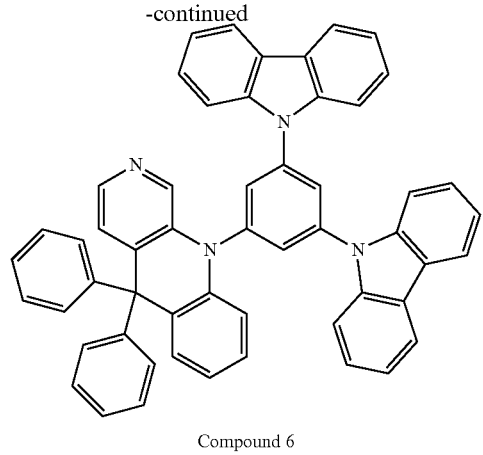

Compound 6

Synthetic process was performed in the same manner as in the synthesis of the Compound 1 except that 2.44 g (5 mmol) of intermediate 6-1 and 1.5 g (4.5 mmol) of intermediate 1-3 were used as reactants to give 2.17 g (yield: 65%) of white solid Compound 6.

Synthesis Example 7: Synthesis of Compound 7

(1) Synthesis of Intermediate 7-1 (9-(3-fluoro-5-bromo-phenyl)-9H-carbazole)

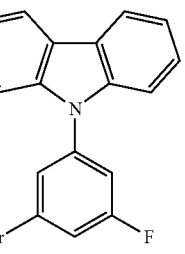

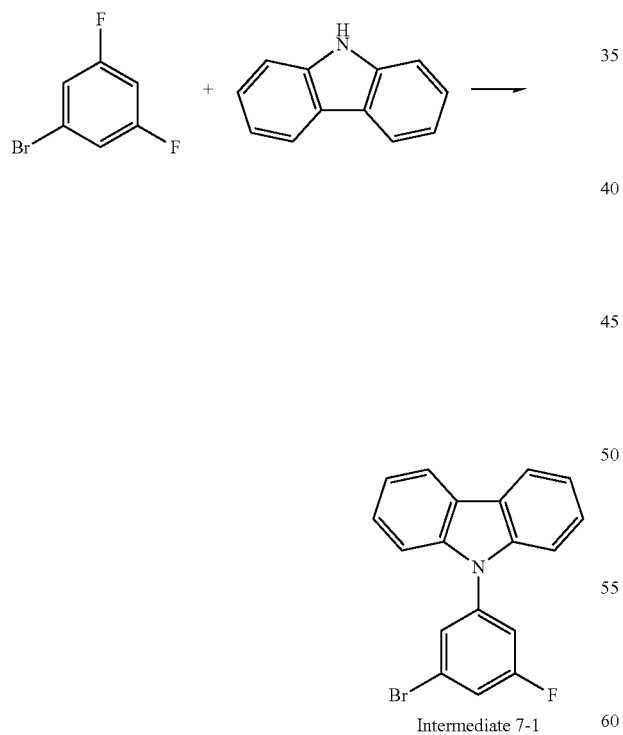

Intermediate 7-1

Synthetic process was performed in the same manner as in the synthesis of the Compound 1 except that 10 g (59.8 mmol) of carbazole and 11.6 g (60 mmol) of 3,5-difluoro-bromobenzene were used as reactants to give 9.8 g (yield: 48%) of intermediate 7-2.

(2) Synthesis of Intermediate 7-1 9-(3-(3-(9H-carbazol-9-yl)-9H-carbazol-9-yl)-5-bromophenyl)-9H-carbazole)

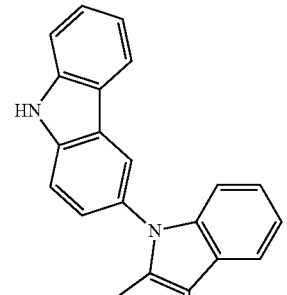

Intermediate 7-1

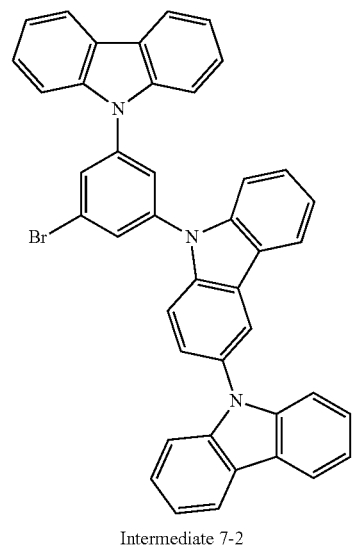

Intermediate 7-2

Synthetic process was performed in the same manner as in the synthesis of the Compound 1 except that 5 g (14.7 mmol) of intermediate 7-1 and 4.89 g (14.7 mmol) of intermediate 5-1 were used as reactants to give 5.1 g (yield: 53%) of intermediate 7-2.

(3) Synthesis of Compound 7 (10-(3-(3-(9H-carbazol-9-yl)-9H-carbazol-9-yl)-5-(9H-carbazol-9-yl)phenyl)-5,10-dihydro-5,5-diphenylbenzo[b][1,7]naphthyridine)

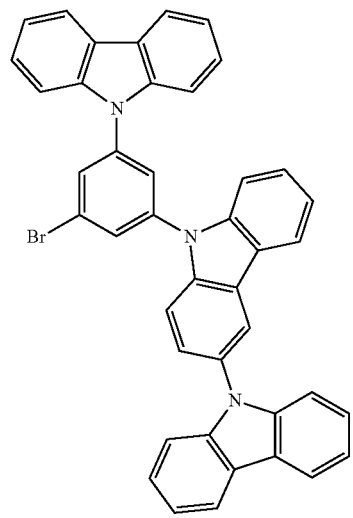

Intermediate 7-2

+

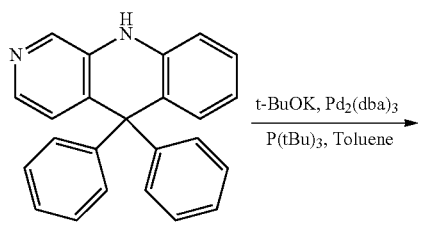

Intermediate 1-3 t-BuOK, Pd₂(dba)₃
P(tBu)₃, Toluene
→

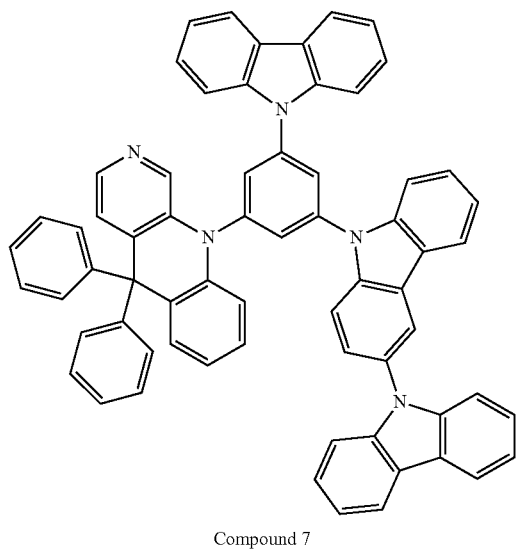

Compound 7

Synthetic process was performed in the same manner as in the synthesis of the Compound 1 except that 3.26 g (5 mmol) of intermediate 7-2 and 1.5 g (4.5 mmol) of intermediate 1-3 were used as reactants to give 2.08 g (yield: 51%) of white solid Compound 7.

Synthesis Example 8: Synthesis of Compound 8

(1) Synthesis of Intermediate 8-1

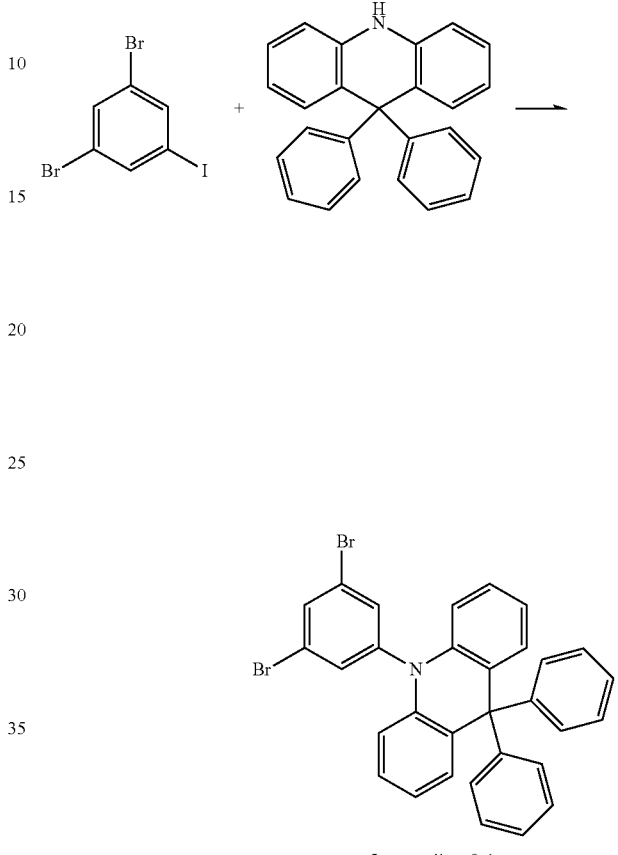

Intermediate 8-1

Synthetic process was performed in the same manner as in the synthesis of the intermediate 3-1 except that 30.4 g (84.0 mmol) of 1,3-dibromo-5-iodobenzene and 30.2 g (90.6 mmol) of diphenylacridine were used as reactants to give 15.4 g (yield: 32%) of Intermediate 8-1.

(2) Synthesis of Intermediate 8-2

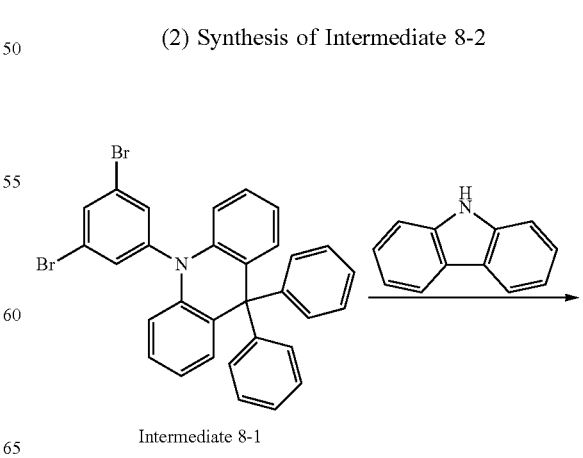

Intermediate 8-1

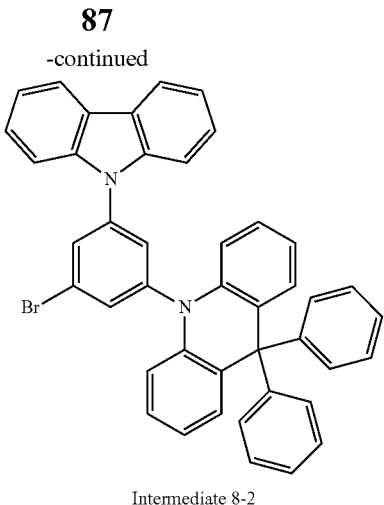

Intermediate 8-2

Synthetic process was performed in the same manner as in the synthesis of the intermediate 1-4 except that 15.4 g (27.1 mmol) of intermediate 8-1 and 4.5 g (26.9 mmol) of carbazole were used as reactants to give 15.7 g (yield: 76%) of intermediate 8-2.

(3) Synthesis of Compound 8 (10-(3-(9H-carbazol-9-yl)-5-(9,9-diphenylacridin-10(9H)-yl)phenyl)-5,10-dihydro-5,5-diphenylbenzo[b][1,7]naphthyridine)

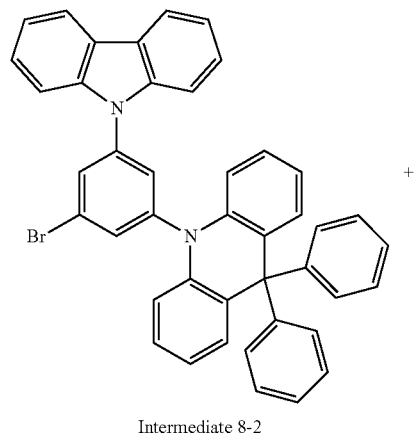

Intermediate 8-2

+

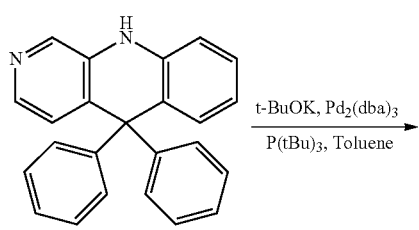

t-BuOK, Pd$_2$(dba)$_3$
P(tBu)$_3$, Toluene →

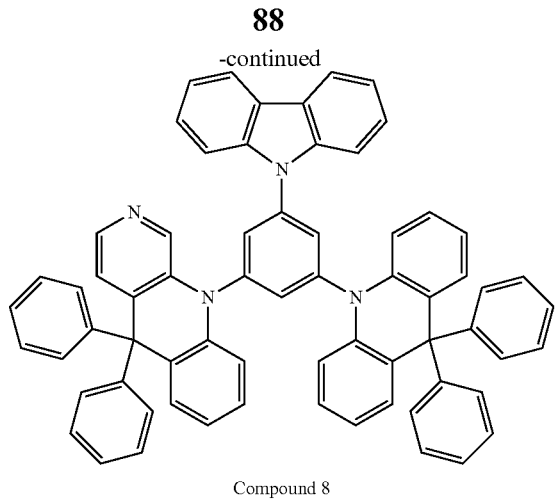

Compound 8

Synthetic process was performed in the same manner as in the synthesis of the Compound 1 except that 3.27 g (5 mmol) of intermediate 8-2 and 1.5 g (4.5 mmol) of intermediate 1-3 were used as reactants to give 1.88 g (yield: 46%) of Compound 8.

Experimental Example 1: Measurement of Physical Properties of Organic Compound

Physical properties for the Compounds 1 to 8 were evaluated. Particularly, HOMO energy level, LUMO energy level, energy level bandgap (LUMO-HOMO, Eg) and triplet energy level ($T_1$) and for each of the compounds were evaluated. For the comparison, physical properties for the Reference compound (Ref.) having the following structure was evaluated. The measurement results are indicated in the following Table 1.

[Reference Compound]

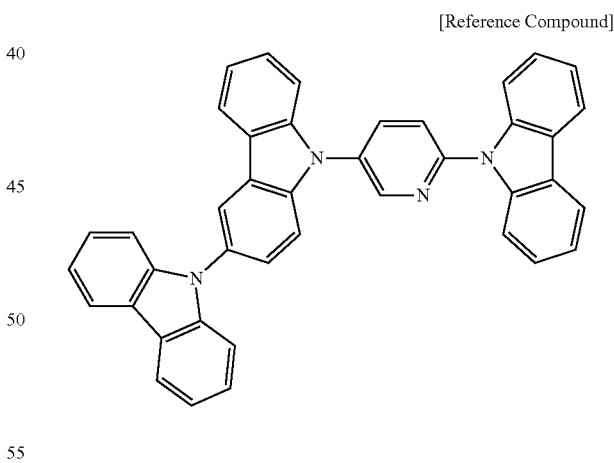

TABLE 1

Luminescence Properties of Organic Compound

| Compound | HOMO* (eV) | LUMO* (eV) | Eg (eV) | $T_1$* (eV) |
|---|---|---|---|---|
| Ref. | −5.81 | −2.22 | 3.59 | 3.01 |
| Compound 1 | −5.93 | −2.16 | 3.77 | 3.27 |
| Compound 2 | −6.05 | −2.11 | 3.96 | 2.83 |
| Compound 3 | −5.98 | −2.22 | 3.76 | 3.29 |
| Compound 4 | −5.97 | −2.27 | 3.70 | 2.78 |
| Compound 5 | −6.22 | −2.20 | 4.02 | 3.17 |

TABLE 1-continued

Luminescence Properties of Organic Compound

| Compound | HOMO* (eV) | LUMO* (eV) | Eg (eV) | $T_1$* (eV) |
|---|---|---|---|---|
| Compound 6 | −6.16 | −2.34 | 3.82 | 3.11 |
| Compound 7 | −6.21 | −2.16 | 4.05 | 3.12 |
| Compound 8 | −6.01 | −2.02 | 3.99 | 3.21 |

*HOMO: Film (100 nm/ITO) by AC3;
*LUMO: Calculated from film absorption edge;
*$T_1$: Calculated by Gaussian ED–DFT(time-dependent density functional theory), solution (toluene) by FP-8600

As indicated by Table 1, each of Compounds 1-8 showed an adequate HOMO energy level, LUMO energy level and energy level bandgap as used luminous material in an emitting layer. Also, each of Compounds 1-8 showed a high triplet energy level as a host. Considering the triplet energy levels of the Compounds, it was found that the use of those compounds in combination with a delayed fluorescent material was suitable for exciton energy transfer so that good luminous efficiency was implemented while reducing the non-emission quenching.

Example 1: Fabrication of Organic Light Emitting Diode (OLED)

An organic light emitting diode was fabricated using Compound 1 synthesized in the Synthesis Example 1 as a host in an emitting material layer (EML). An ITO (including reflective layer) attached glass substrate with 40 mm×40 mm×0.5 mm was ultrasonically cleaned with isopropyl alcohol, acetone and distilled water for 5 minutes and then dried in an oven at 100° C. The cleaned substrate was treated with $O_2$ plasma in a vacuum for 2 minutes and transferred to a deposition chamber in order to deposit other layers on the substrate. An organic layer was deposited by evaporation by a heated boat under $10^{-7}$ torr in the following order. The deposition rate of the organic layer was set to 1 Å/s.

A hole injection layer (HIL) (HAT-CN; 50 Å); a hole transport layer (HTL) (TAPC, 500 Å); an electron blocking layer (EBL) (DCDPA; 100 Å); an emitting material layer (EML) (Compound 1 (host): TcTrz (delayed fluorescent material)=70:30 by weigh ratio; 250 Å); a hole blocking layer (HBL) (TSPO1; 100 Å); an electron transport layer (ETL) (TPBi; 300 Å); an electron injection layer (EIL) (LiF; 15 Å); and a cathode (Al; 1000 Å).

And then, capping layer (CPL) was deposited over the cathode and the device was encapsulated by glass. After deposition of emissive layer and the cathode, the OLED was transferred from the deposition chamber to a dry box for film formation, followed by encapsulation using UV-curable epoxy and moisture getter. The manufacture organic light emitting diode had an emission area of 9 mm².

Examples 2 to 6: Fabrication of OLED

An organic light emitting diode was manufactured as the same process and the same materials as Example 1, except using Compound 3 (Example 2), Compound 5 (Example 3), Compound 6 (Example 4), Compound 7 (Example 5) and Compound 8 (Example 6) as the host in place of Compound 1 in the EML.

Comparative Example: Manufacture of OLED

An organic light emitting diode was manufactured as the same process and the same materials as Example 1, except using Reference Compound (Ref.) as the host in place of Compound 1 in the EML.

Experimental Example 2: Measurement of Luminous Properties of OLED

Each of the organic light emitting diode fabricated in Examples 1 to 6 and Comparative Example was connected to an external power source, and luminous properties for all the diodes were evaluated using a constant current source (KEITHLEY) and a photometer PR650 at room temperature. In particular, driving voltage (V), current efficiency (cd/A), external quantum efficiency (EQD; %) and color coordinates (CIEx and CIEy) at a current density of 10 mA/cm² of the light emitting diodes of Examples 1 to 6 and Comparative Example were measured. The results thereof are shown in the following Table 2.

TABLE 2

Luminous Properties of OLED

| Sample | V | cd/A | EQE (%) | CIEx, CIEy |
|---|---|---|---|---|
| Ref. | 3.9 | 32.1 | 18.3 | 0.161, 0.257 |
| Example 1 | 3.5 | 40.4 | 25.2 | 0.160, 0.255 |
| Example 2 | 3.4 | 40.9 | 25.6 | 0.159, 0.252 |
| Example 3 | 3.6 | 39.1 | 23.7 | 0.163, 0.250 |
| Example 4 | 3.8 | 35.3 | 21.2 | 0.160, 0.250 |
| Example 5 | 3.7 | 37.8 | 22.7 | 0.159, 0.249 |
| Example 6 | 3.6 | 39.9 | 24.1 | 0.162, 0.252 |

As indicated in Table 2, compared with the OLED including reference compound as the host in the EML of the Comparative Example, the OLED including the organic compounds as the host in the EML of the Examples reduced its driving voltage up to 12.8%, and improved its current efficiency up to 27.4% and its external quantum efficiency up to 39.9% It was confirmed that the OLED can lower its driving voltage and improve its luminous efficiency by applying the organic compound of the present disclosure into an emitting unit. Accordingly, an organic light emitting device such as an organic light emitting display device having reduced power consumption and improved luminous efficiency and luminous lifetime can be realized by using the organic light emitting diode into which the organic compound of the present disclosure is applied.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic compound having the structure of Chemical Formula 1:

Chemical Formula 1

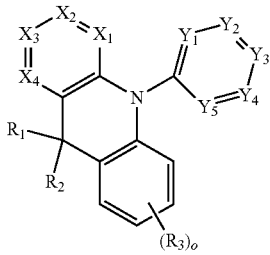

wherein:
each of $R_1$ and $R_2$ is independently protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or $R_1$ and $R_2$ form a $C_5$-$C_{30}$ spiro structure;
each $R_3$ is independently protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or adjacent two groups among $R_3$ form $C_4$-$C_{20}$ fused aromatic or hetero aromatic ring; o is an integer from 0 to 4;
wherein $X_2$ is a nitrogen atom (N);
each of $X_1$, $X_3$ and $X_4$ is independently $CR_4$ or nitrogen atom (N), wherein at least one of $X_1$ to $X_4$ is nitrogen atom, wherein $R_4$ is protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or adjacent two groups among $R_4$ form $C_4$-$C_{30}$ fused aromatic or hetero aromatic ring; and
each of $Y_1$ to $Y_5$ is independently $CR_5$ or nitrogen atom (N), wherein at least three of $Y_1$ to $Y_5$ is $CR_5$, wherein $R_5$ is protium, deuterium, tritium, linear or branched $C_1$-$C_{20}$ alkyl group, $C_1$-$C_{20}$ alkoxy group or $C_{10}$-$C_{30}$ fused group of a heterocycle ring and an aryl group, wherein the $C_{10}$-$C_{30}$ fused group of a heterocycle ring and an aryl group is unsubstituted or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and a combination thereof, fused with a $C_4$-$C_{20}$ aromatic or hetero aromatic ring or linked by a spiro structure of a $C_4$-$C_{20}$ aromatic or hetero aromatic ring, wherein at least one $R_5$ among $Y_1$ to $Y_5$ is $C_{10}$-$C_{30}$ fused group of a heterocycle ring and an aryl group unsubstituted or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and a combination thereof, fused with a $C_4$-$C_{20}$ aromatic or hetero aromatic ring or linked by a spiro structure of a $C_4$-$C_{20}$ aromatic or hetero aromatic ring.

2. The organic compound of claim 1, wherein the $C_{10}$-$C_{30}$ fused group of a heterocycle ring and an aryl group includes at least one nitrogen atom (N).

3. The organic compound of claim 1, wherein the $C_{10}$-$C_{30}$ fused group of a heterocycle ring and an aryl group constituting $R_5$ is selected from the group consisting of carbazolyl, acridinyl, carbolinyl, spirofluorenocarbazolyl, spirofluorenoacridinyl, phenazinyl, phenoxazinyl and phenothiazinyl, and wherein each of the carbazolyl, the acridinyl, the carbolinyl, the spirofluorenocarbazolyl, the spirofluorenoacridinyl, the phenazinyl, the phenoxazinyl and the phenothiazinyl is independently unsubstitued or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and a combination thereof, fused with a $C_4$-$C_{20}$ aromatic or hetero aromatic ring or linked by a spiro structure of a $C_4$-$C_{20}$ aromatic or hetero aromatic ring, respectively.

4. The organic compound of claim 1, having the structure of Chemical Formula 2:

Chemical Formula 2

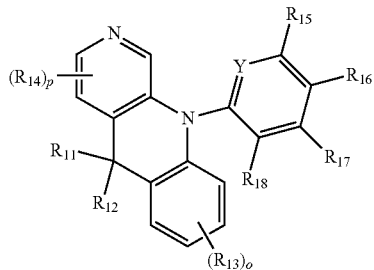

wherein:
each of $R_{11}$ and $R_{12}$ is independently linear or branched $C_1$-$C_{20}$ lalkyl group or $C_6$-$C_{20}$ aryl group;
each of $R_{13}$ and $R_{14}$ is independently protium, deuterium, tritium or linear or branched $C_1$-$C_{20}$ alkyl group; o is an integer from 0 to 4; p is an integer from 1 to 3;
each of $R_{15}$ to $R_{18}$ is independently protium, deuterium, tritium, linear or branched $C_1$-$C_{20}$ alkyl group or $C_{10}$-$C_{30}$ fused group of a heterocycle ring and an aryl group having at least one nitrogen atom (N) on a ring, wherein the $C_{10}$-$C_{30}$ fused group of a heterocycle ring and an aryl group is unsubstituted or substituted a group selected from the group consisting of linear or branched $C_1$-$C_{20}$ alkyl group, $C_6$-$C_{30}$ aryl group, $C_4$-$C_{30}$ hetero aryl group, $C_4$-$C_{30}$ aromatic or hetero aromatic amino group and a combination thereof, wherein at least one of $R_{15}$ to $R_{18}$ is $C_{10}$-$C_{30}$ fused group of a heterocycle ring and an aryl group having at least one nitrogen atom (N) on the ring, wherein the $C_{10}$-$C_{30}$ fused group of a heterocycle ring and an aryl group is unsubstituted or substituted with a group selected from the group consisting of linear or branched $C_1$-$C_{20}$ alkyl group, $C_6$-$C_{30}$ aryl group, $C_4$-$C_{30}$ hetero aryl group, $C_4$-$C_{30}$ aromatic or hetero aromatic amino group and a combination thereof;
Y is nitrogen atom (N) or $CR_{19}$, wherein $R_{19}$ is protium, deuterium, tritium or linear or branched $C_1$-$C_{20}$ alkyl group.

5. The organic compound of claim 1, having the structure of Chemical Formula 3:

Chemical Formula 3
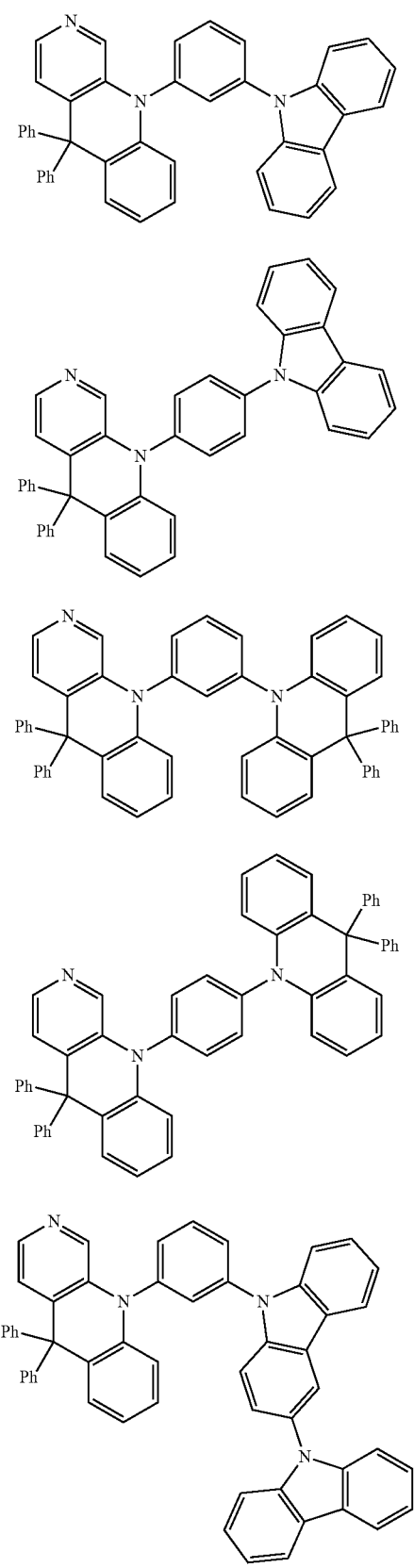
Compound 1
Compound 2
Compound 3
Compound 4
Compound 5
-continued
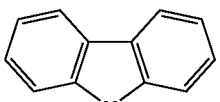
Compound 6
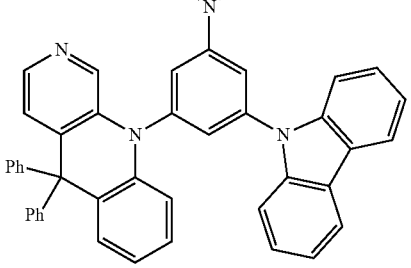
Compound 7
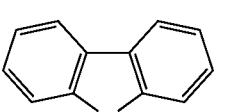
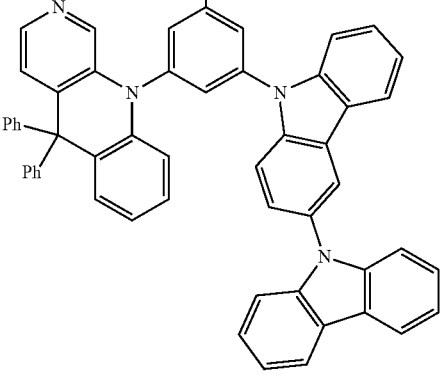
Compound 8
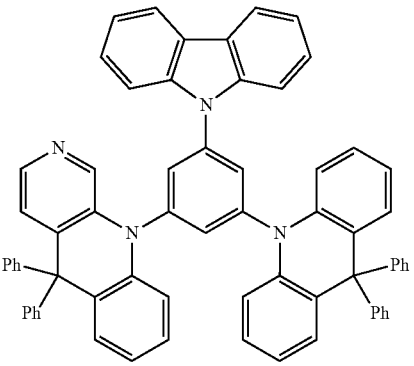
Compound 9
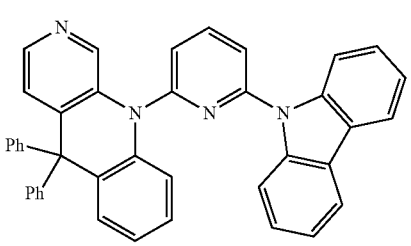

-continued
Compound 10
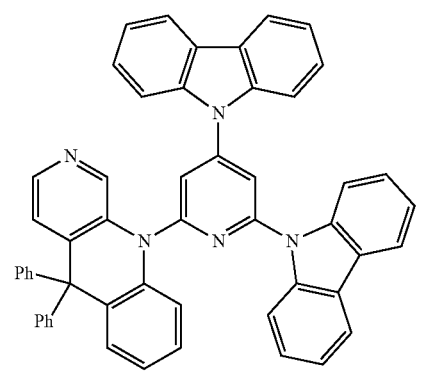
Compound 11
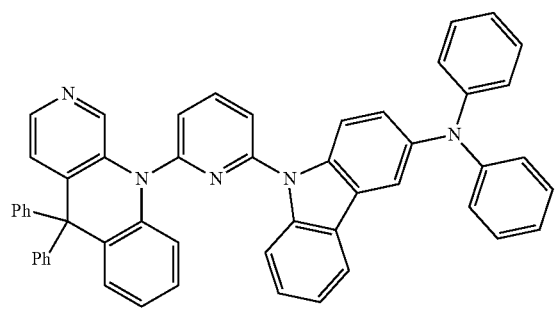
Compound 12
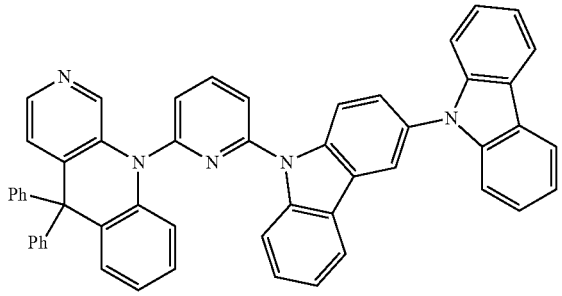
Compound 13
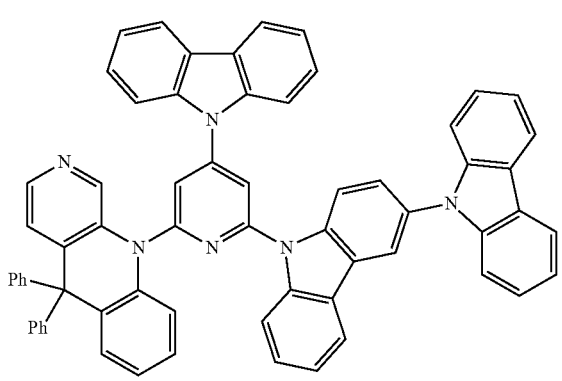
-continued
Compound 14
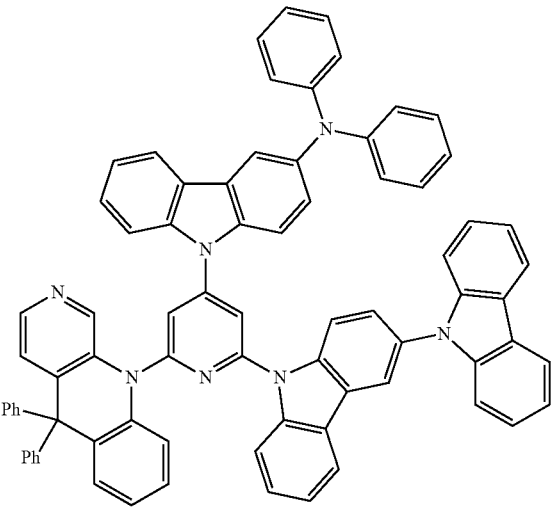
Compound 15
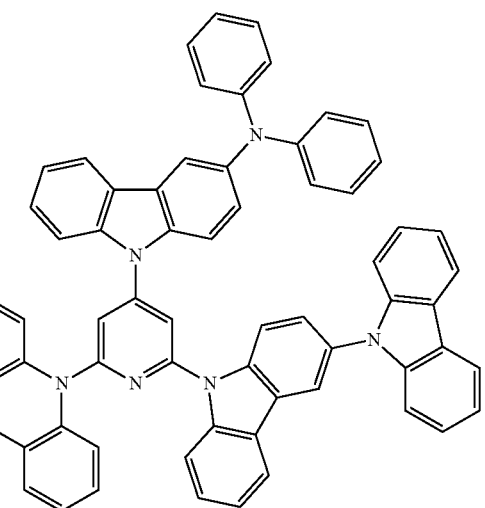
Compound 16
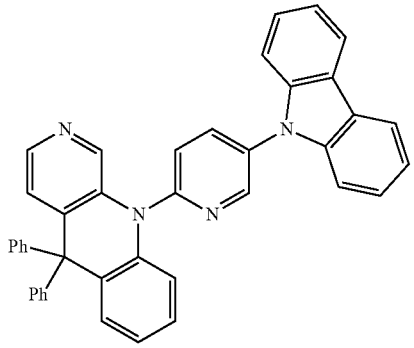

Compound 17
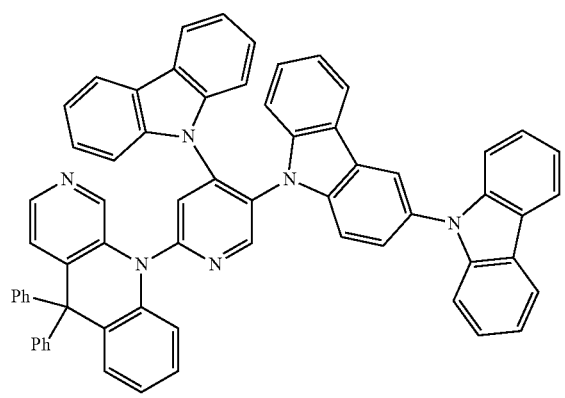
Compound 18
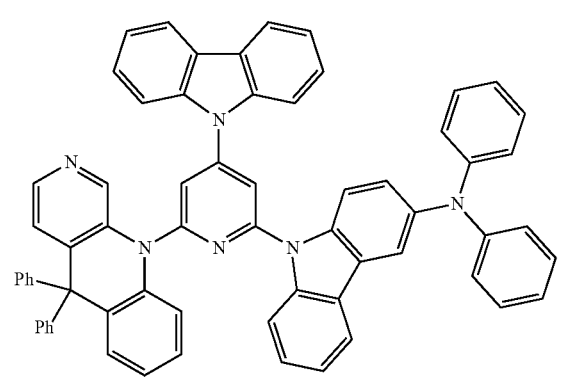
Compound 19
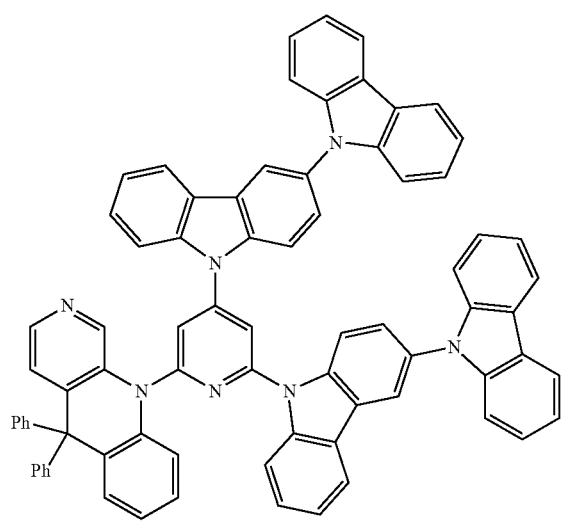
Compound 20
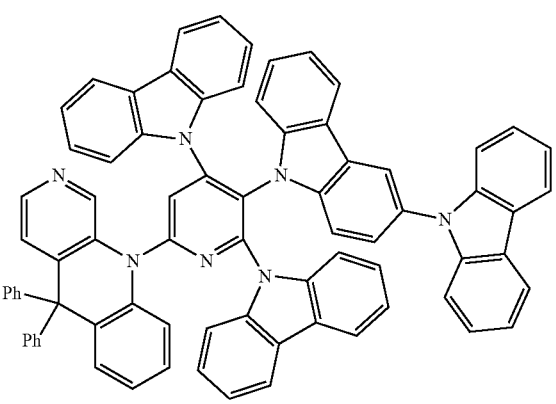
Compound 21
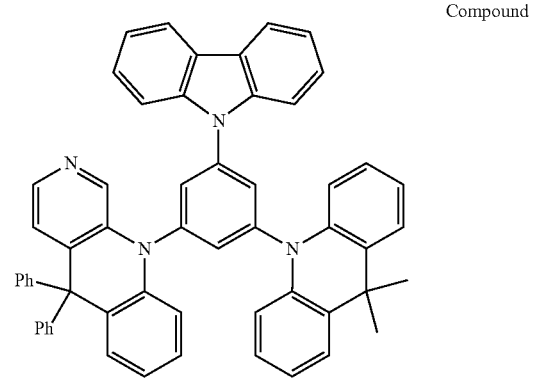
Compound 22
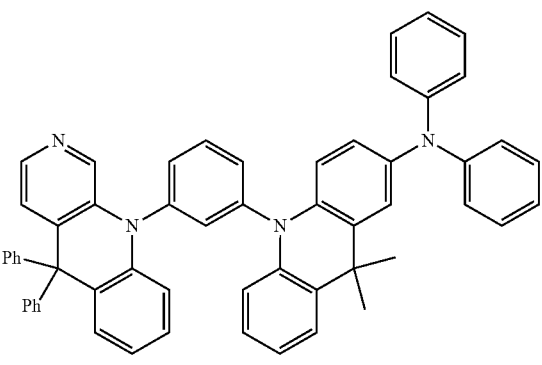
Compound 23
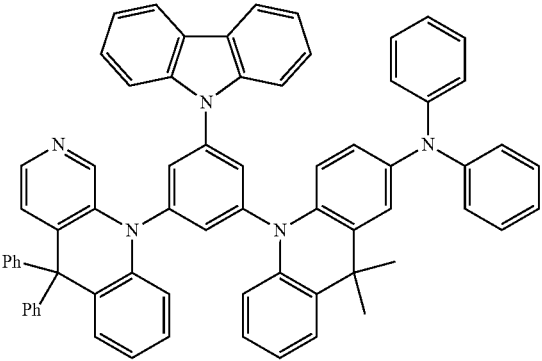

Compound 24
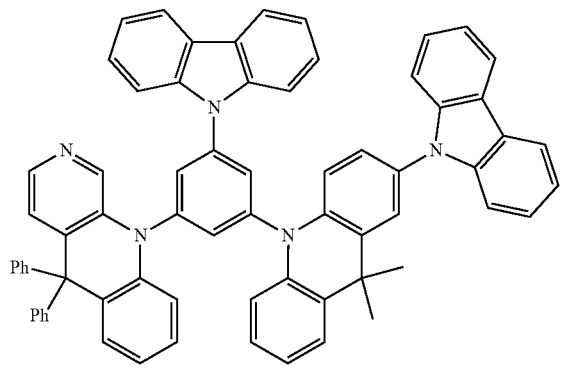
Compound 27
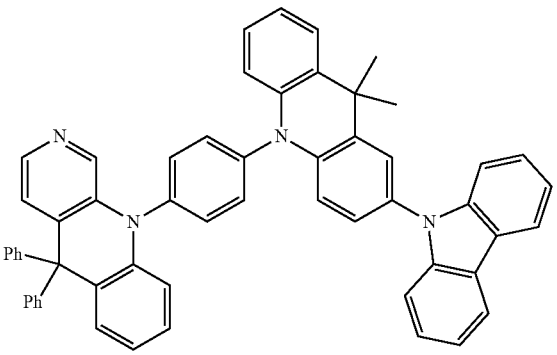
Compound 25
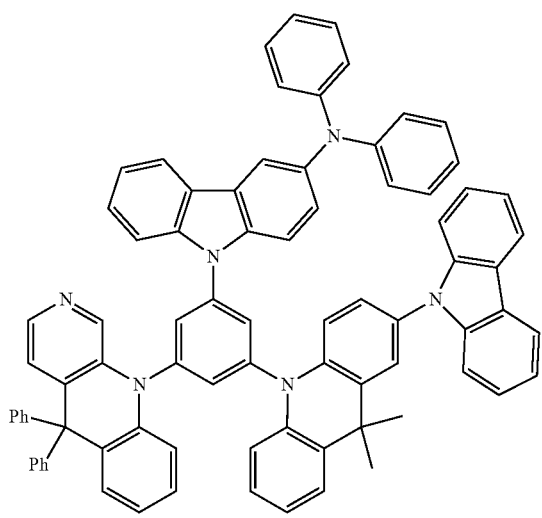
Compound 28
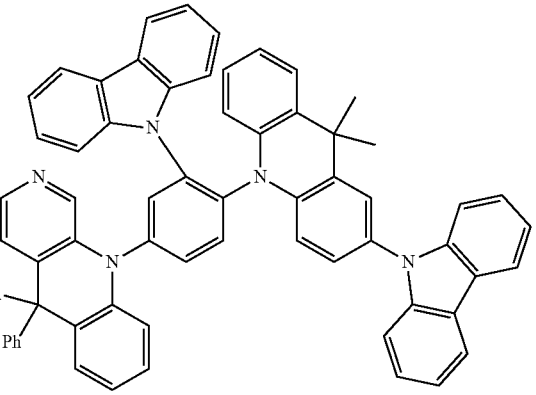
Compound 26
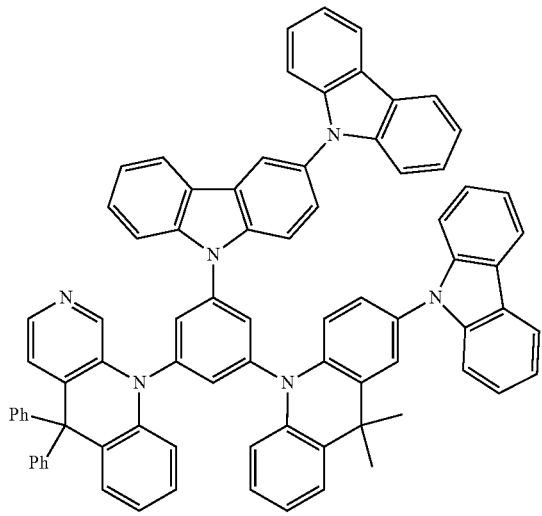
Compound 29
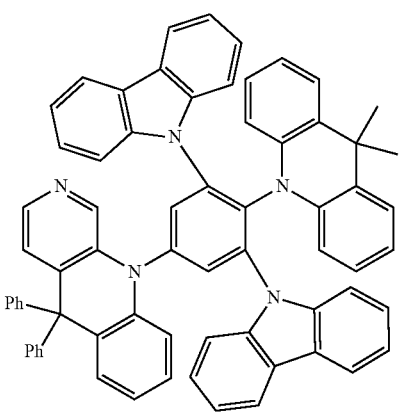
Compound 30
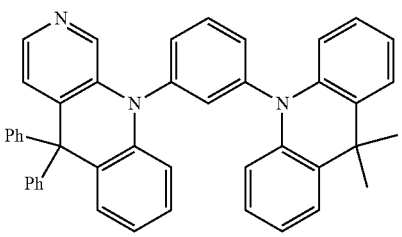

Compound 31
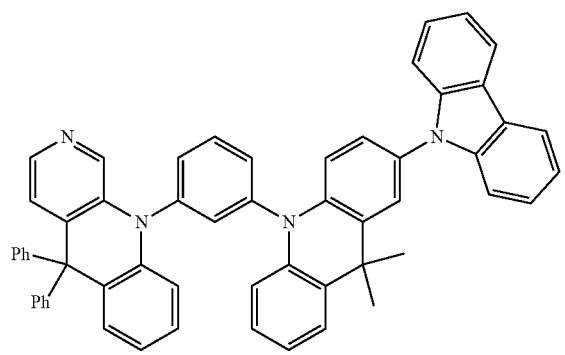
Compound 32
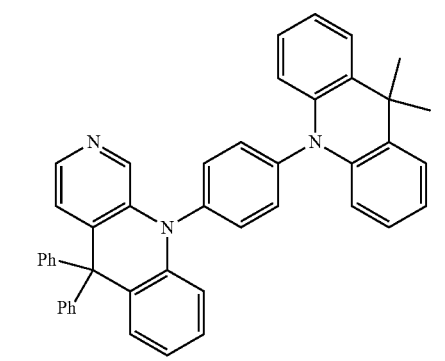
Compound 33
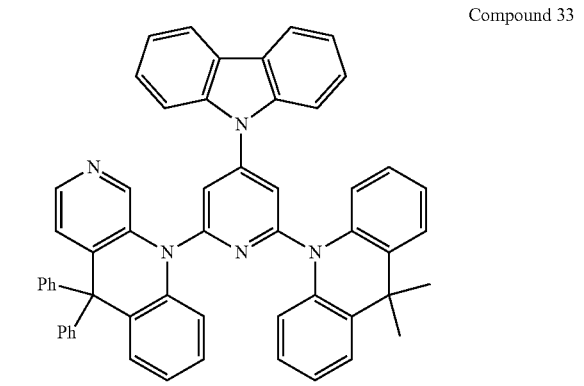
Compound 34
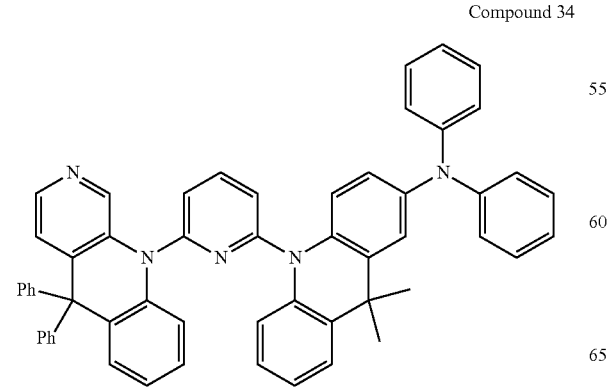
Compound 35
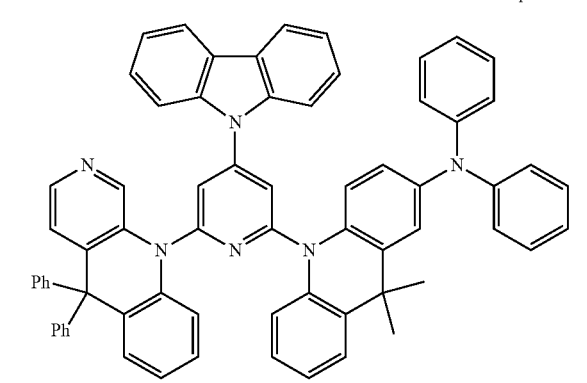
Compound 36
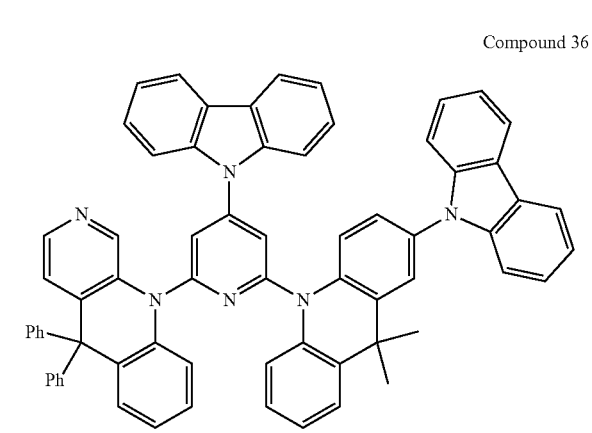
Compound 37
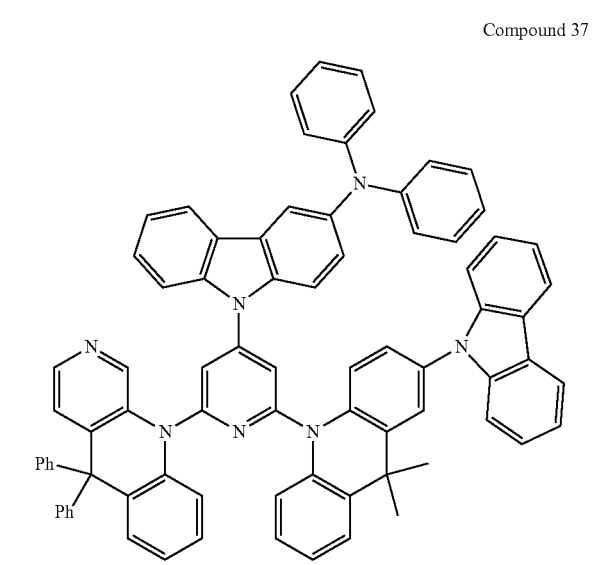

-continued
Compound 38
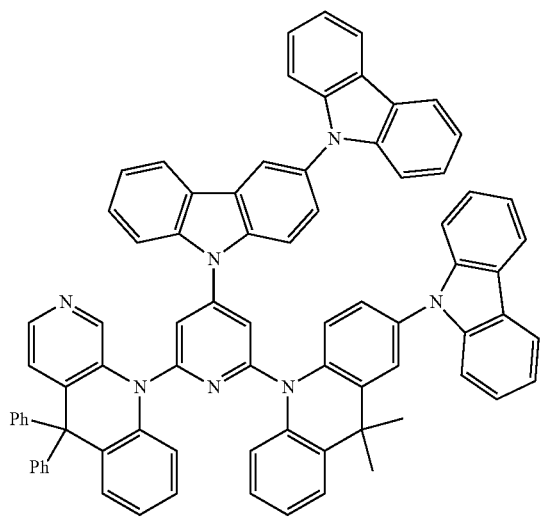
Compound 39
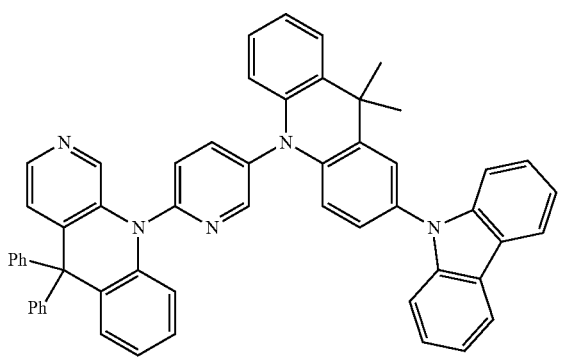
Compound 40
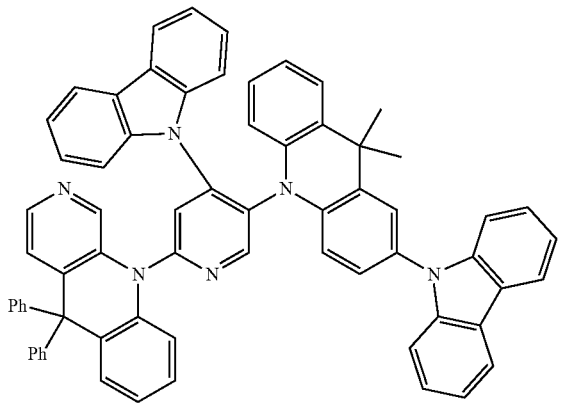
-continued
Compound 41
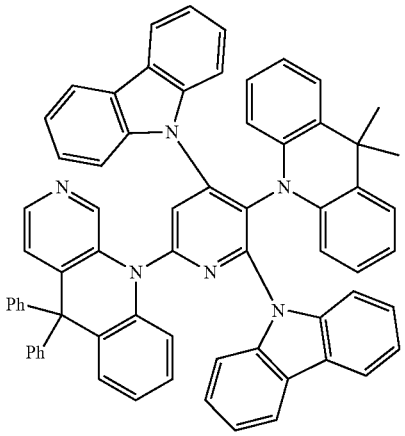
Compound 42
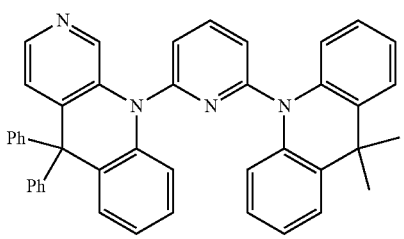
Compound 43
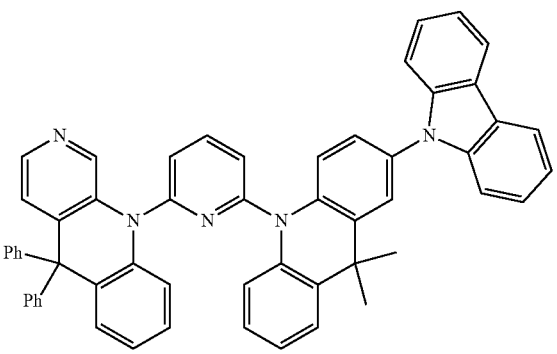
Compound 44
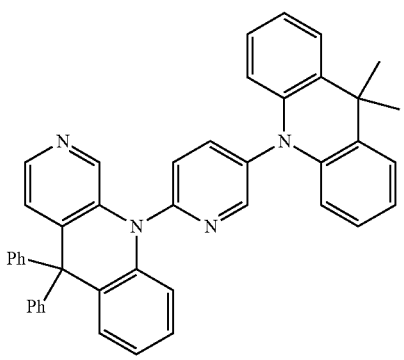

Compound 45
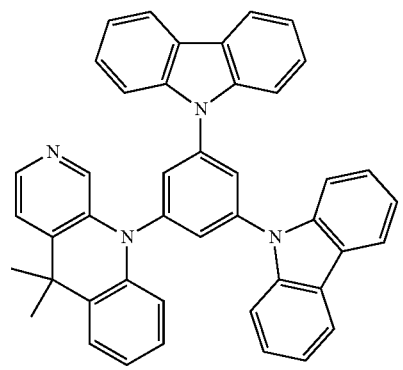
Compound 46
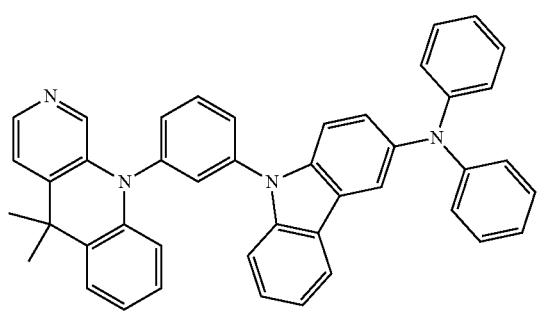
Compound 47
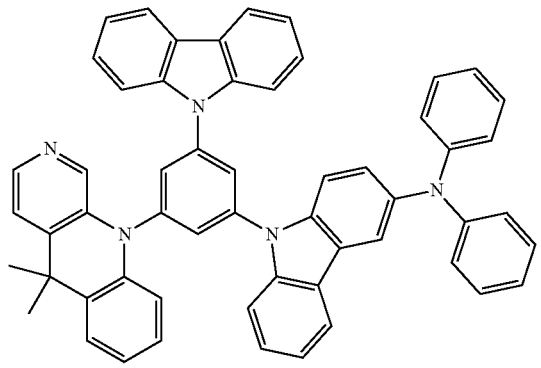
Compound 48
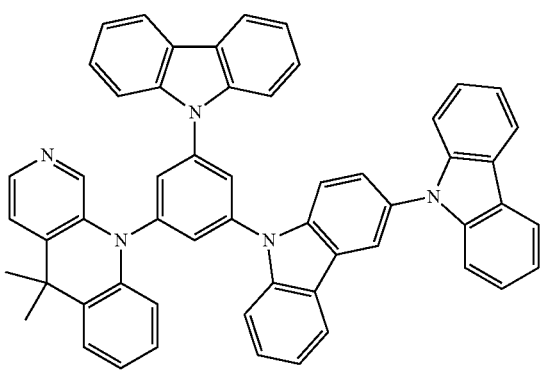
Compound 49
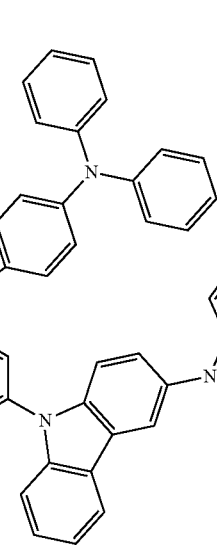
Compound 50
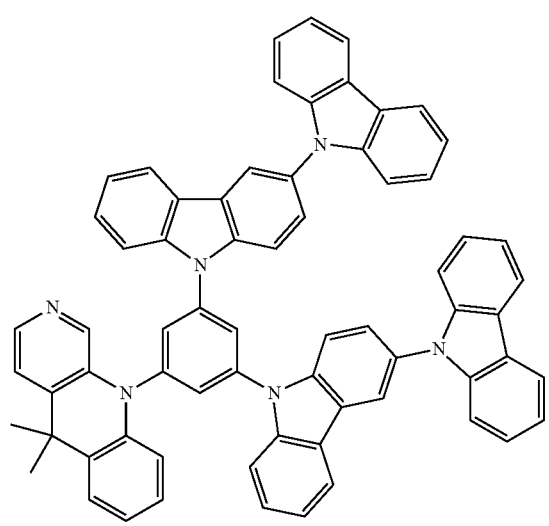
Compound 51
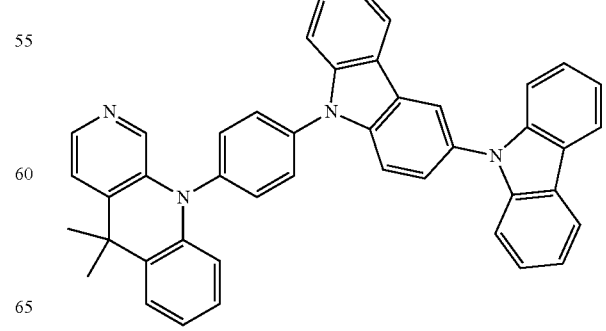

Compound 52
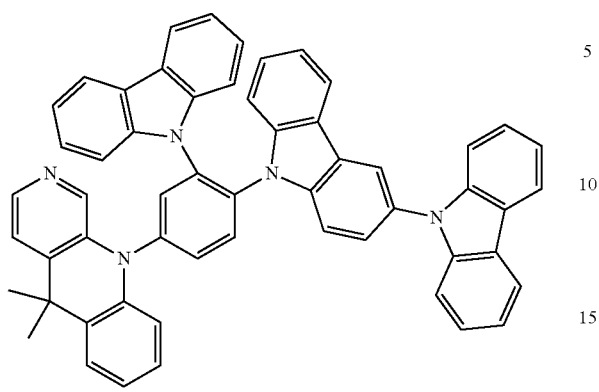
Compound 53
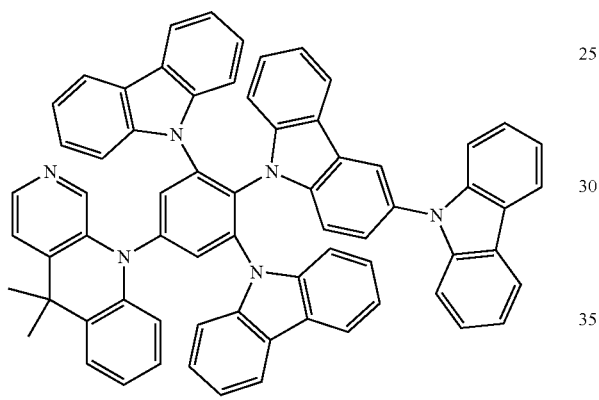
Compound 54
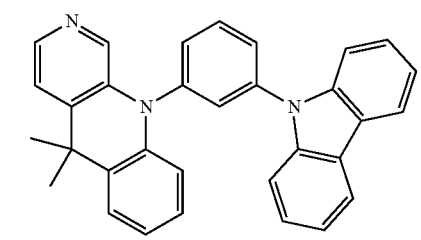
Compound 55
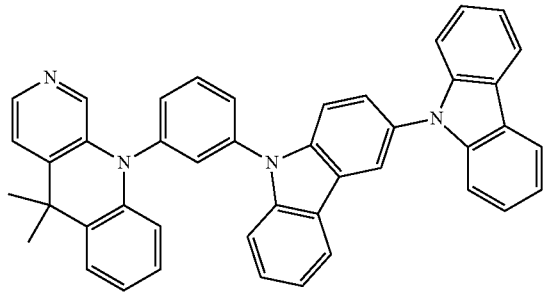
Compound 56
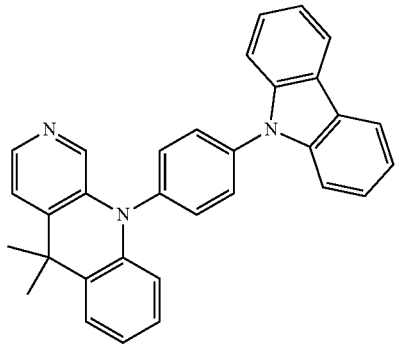
Compound 57
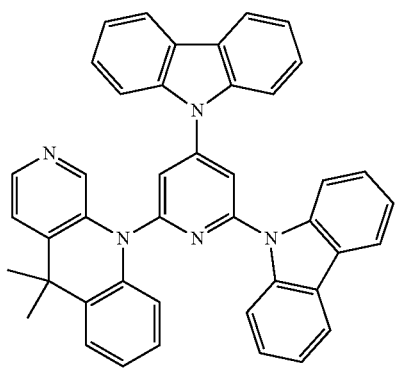
Compound 58
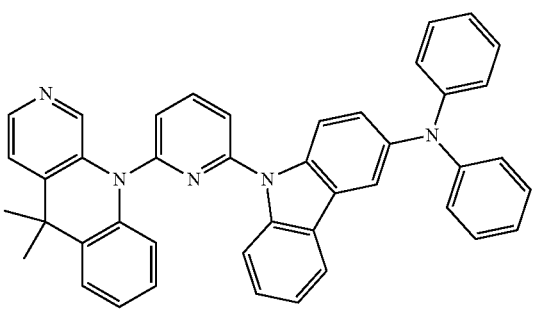
Compound 59
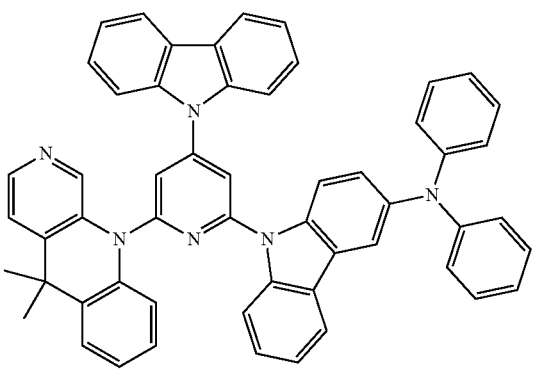

Compound 60
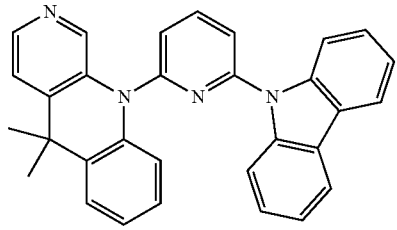
Compound 63
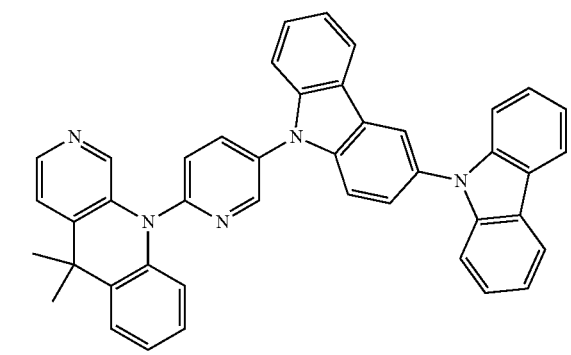
Compound 61
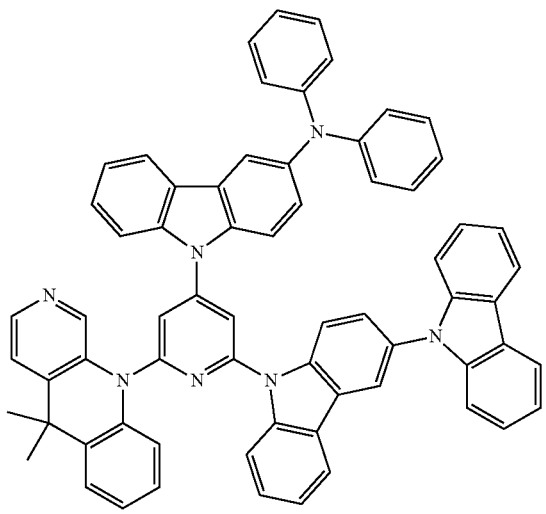
Compound 64
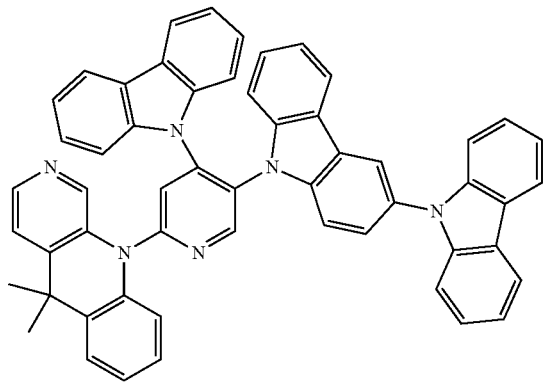
Compound 65
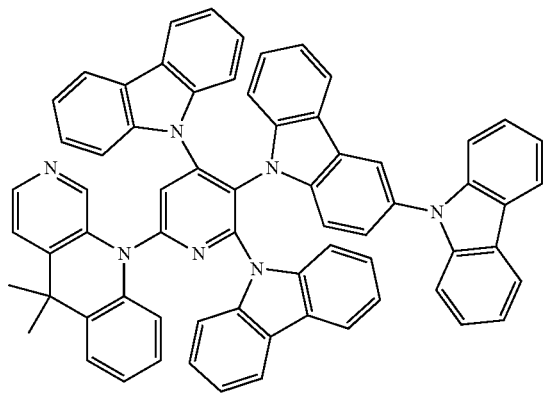
Compound 62
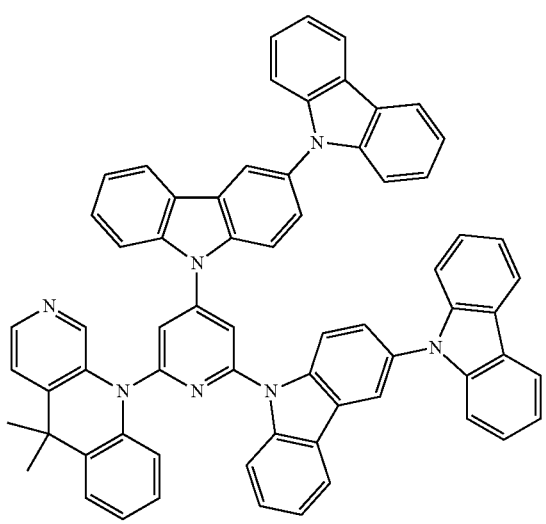
Compound 66
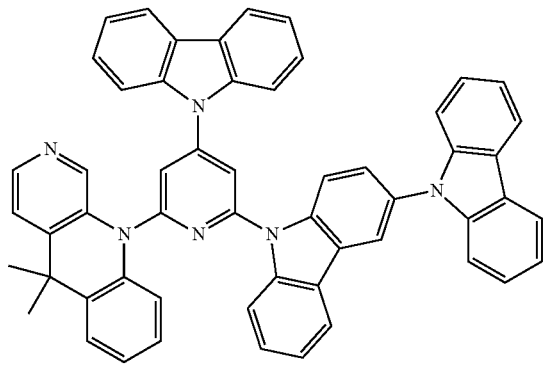

US 11,401,268 B2
Compound 67
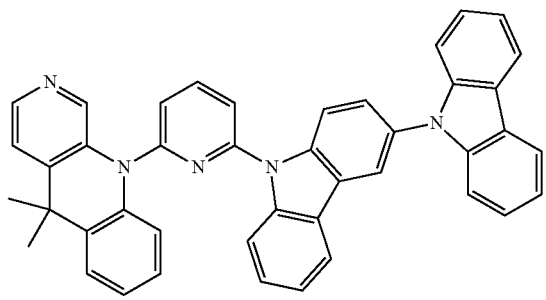
Compound 68
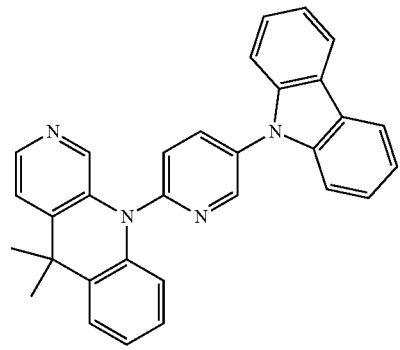
Compound 69
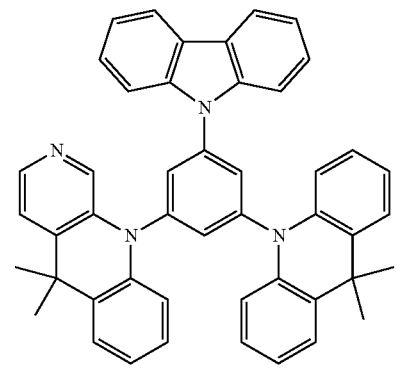
Compound 70
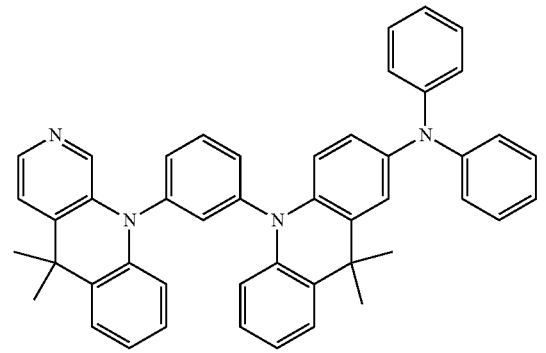
Compound 71
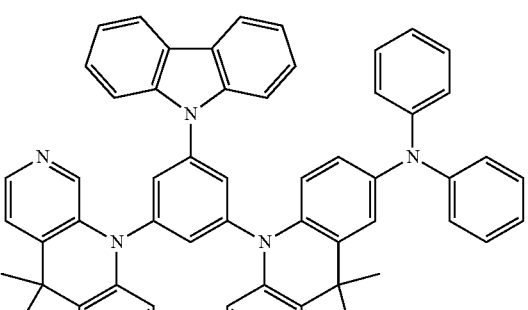
Compound 72
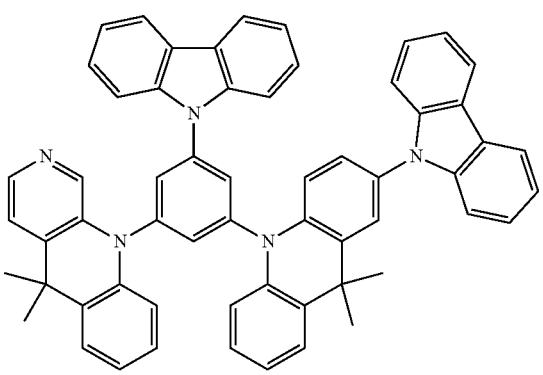
Compound 73
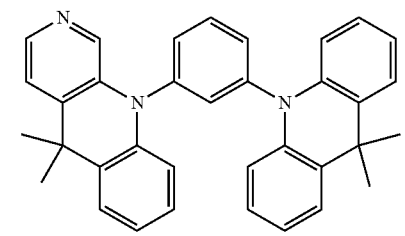
Compound 74
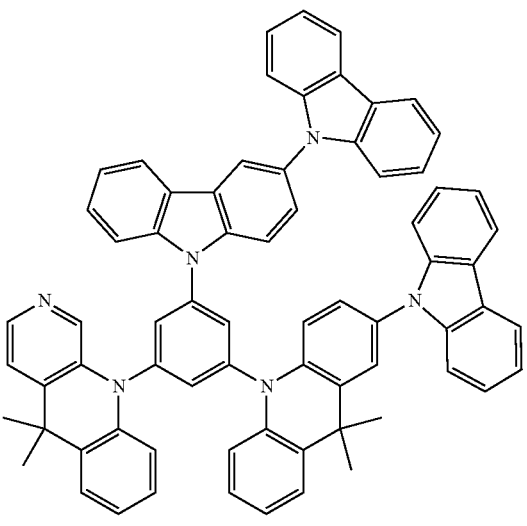

Compound 75

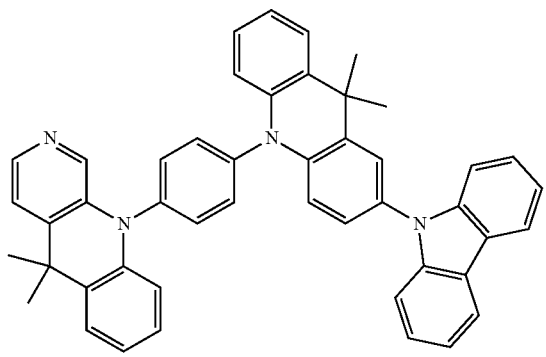

Compound 76

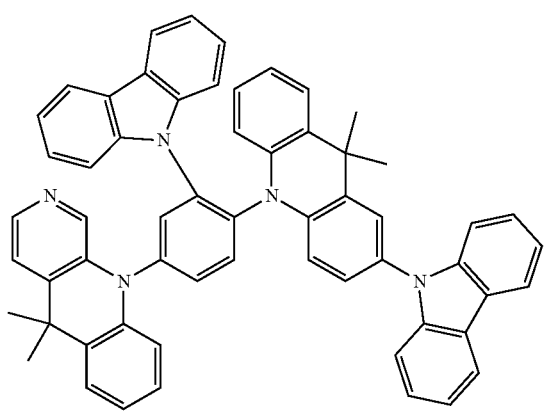

Compound 77

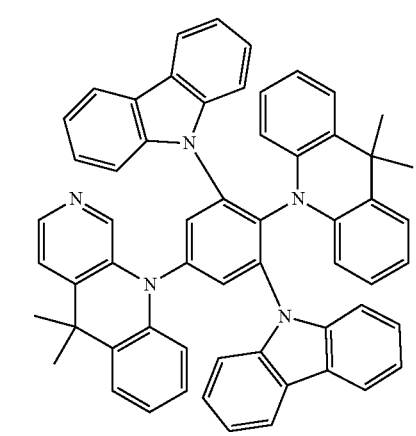

Compound 78

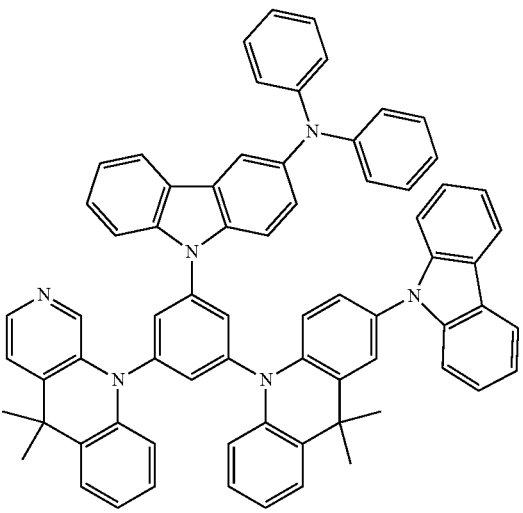

Compound 79

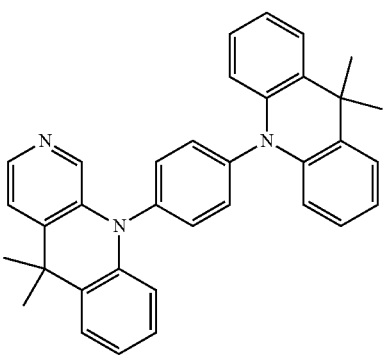

Compound 80

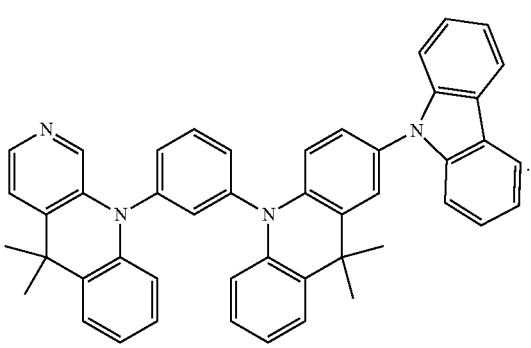

6. An organic lightemitting diode, comprising:
  a first electrode;
  a second electrode facing the first electrode;
  at least one emitting unit disposed between the first and second electrodes and wherein
  the at least one emitting unit comprises an emitting material layer,
  wherein the emitting material layer comprises an organic compound having the structure of Chemical Formula 1:

Chemical Formula 1

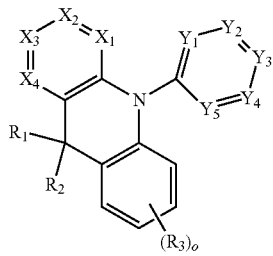

wherein:
each of $R_1$ and $R_2$ is independently protium, deuterium, tritium, linear or branched $C_1$-$C_{20}$, alkyl group, $C_1$-$C_{20}$ alkoxy group, $C_6$-$C_{30}$ aryl group or $C_4$-$C_{30}$ hetero aryl group, or $R_1$ and $R_2$ form $C_5$-$C_{30}$ spiro structure;

each $R_3$ is independently protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or adjacent two groups among $R_3$ form $C_4$-$C_{20}$ fused aromatic or hetero aromatic ring; o is an integer from 0 to 4;

wherein $X_2$ is a nitrogen atom (N):

each of $X_1$, $X_3$ and $X_4$ is independently $CR_4$ or nitrogen atom (N), wherein at least one of $X_1$ to $X_4$ is nitrogen atom, wherein $R_4$ is protium, deuterium, tritium, linear or branched $C_1$-$C_{20}$ alkyl group, $C_1$-$C_{20}$ alkoxy group, $C_6$-$C_{30}$ aryl group or $C_4$-$C_{30}$ hetero aryl group, or adjacent two groups among $R_4$ form $C_4$-$C_{30}$ fused aromatic or hetero aromatic ring;

each of $Y_1$ to $Y_5$ is independently $CR_5$ or nitrogen atom (N), wherein at least three of $Y_1$ to $Y_5$ is $CR_5$, wherein $R_5$ is protium, deuterium, tritium, linear or branched. $C_1$-$C_{20}$ alkyl group, $C_1$-$C_{20}$ alkoxy group or $C_{10}$-$C_{30}$ fused group of a heterocycle ring and an aryl group, wherein the $C_{10}$-$C_{30}$ fused group of a heterocycle ring and an aryl group is unsubstituted or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and combination thereof, fused with a $C_4$-$C_{20}$ aromatic or hetero aromatic ring or linked by a spiro structure of a $C_4$-$C_{20}$ aromatic or hetero aromatic ring, wherein at least one $R_5$ among $Y_1$ to $Y_5$ is $C_{10}$-$C_{30}$ fused group of a heterocycle ring and an aryl group unsubstituted or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and combination thereof, fused with a $C_4$-$C_{20}$ aromatic or hetero aromatic ring or linked by a spiro structure of a $C_4$-$C_{20}$ aromatic or hetero aromatic ring.

7. The organic light emitting diode of claim 6, wherein the $C_{10}$-$C_{30}$ fused group of a heterocycle ring and an aryl group constituting $R_5$ includes at least one nitrogen atom (N).

8. The organic light emitting diode of claim 6, wherein the $C_{10}$-$C_{30}$ fused group of a heterocycle ring and an aryl group constituting $R_5$ is selected from the group consisting of carbazolyl, acridinyl, carbolinyl, spirofluorenocarbazolyl, spirofluorenoacridinyl, phenazinyl, phenoxazinyl and phenothiazinyl, and wherein each of the carbazolyl, the acridinyl, the carbolinyl, the spirofluorenocarbazolyl, the spirofluorenoacridinyl, the phenazinyl, the phenoxazinyl and the phenothiazinyl is independently unsubstitued or substituted with a group selected from the group consisting of linear or branched $C_1$-$C_{20}$ alkyl group, $C_1$-$C_{20}$ alkoxy group, $C_6$-$C_{30}$ aryl group, $C_4$-$C_{30}$ hetero aryl group, $C_4$-$C_{30}$ aromatic or hetero aromatic amino group and a combination thereof, fused with a $C_4$-$C_{20}$ aromatic or hetero aromatic ring or linked by a spiro structure of a $C_4$-$C_{20}$ aromatic or hetero aromatic ring, respectively.

9. The organic light emitting diode of claim 6, wherein the organic compound has the structure of Chemical Formula 2:

Chemical Formula 2

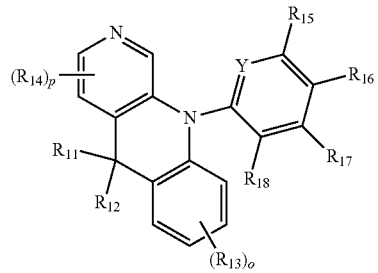

wherein:
each of $R_{11}$ and $R_{12}$ is independently linear or branched $C_1$-$C_{20}$ alkyl group or $C_6$-$C_{20}$ aryl group;

each of $R_{13}$ and $R_{14}$ is independently protium, deuterium, tritium or linear or branched $C_1$-$C_{20}$ alkyl group; o is an integer from 0 to 4; p is an integer from 1 to 3;

each of $R_{15}$ to $R_{18}$ is independently protium, deuterium, tritium, linear or branched $C_1$-$C_{20}$ alkyl group or $C_{10}$-$C_{30}$ fused group of a heterocycle ring and an aryl group having at least one nitrogen atom (N) on a ring, wherein the $C_{10}$-$C_{30}$ fused group of a heterocycle ring and an aryl group is a unsubstituted or substituted group selected from the group consisting of linear or branched $C_1$-$C_{20}$ alkyl group, $C_6$-$C_{30}$ aryl group, $C_4$-$C_{30}$ hetero aryl group, $C_4$-$C_{30}$ aromatic or hetero aromatic amino group and combination thereof, wherein at least one of $R_{15}$ to $R_{18}$ is $C_{10}$-$C_{30}$ fused group of a heterocycle ring and an aryl group having at least one nitrogen atom (N) on the ring, wherein the $C_{10}$-$C_{30}$ fused group of a heterocycle ring and an acyl group is a unsubstituted or substituted with a group selected from the group consisting of linear or branched $C_1$-$C_{20}$ alkyl group, $C_6$-$C_{30}$ aryl group, $C_4$-$C_{30}$ hetero aryl group, $C_4$-$C_{30}$ aromatic or hetero aromatic amino group and combination thereof;

Y is nitrogen atom (N) or $CR_{19}$, wherein $R_{19}$ is protium, deuterium, tritium or linear or branched $C_1$-$C_{20}$ alkyl group.

10. The organic light emitting diode of claim 6, wherein the emitting material layer comprises a first host and a first dopant, and wherein the first host comprises the organic compound.

11. The organic light emitting diode of claim 10, wherein an energy level bandgap between an excited state singlet energy level ($S_1^{TD}$) and an excited state triplet energy level ($T_1^{TD}$) of the first dopant is equal to or less than about 0.3 eV.

12. The organic light emitting diode of claim 10, wherein an excited state singlet energy level ($S_1^H$) and an excited state triplet energy level ($T_1^H$) of the first host is higher than excited state singlet energy level ($S_1^{TD}$) and an excited state triplet energy level ($T_1^{TD}$) of the first dopant, respectively.

13. The organic light emitting diode of claim 10, the emitting material layer further comprises a second dopant, and wherein an excited state singlet energy level ($S_1^{TD}$) of the first dopant is higher than an excited state singlet energy level ($S_1^{TD}$) of the second dopant.

14. The organic light emitting diode of claim 6, wherein the emitting material layer comprises a first emitting material layer disposed between the first and second electrodes and a second emitting material layer disposed between the first electrode and the first emitting material layer or between the first emitting material layer and the second electrode.

15. The organic light emitting diode of claim 14, wherein the first emitting material layer comprises a first host and a first dopant, and wherein the first host comprises the organic compound.

16. The organic light emitting diode of claim 15, wherein the second emitting material layer comprises a second host and a second dopant, and wherein an excited state singlet energy level ($S_1^{TD}$) of the first dopant is higher than an excited state singlet energy level ($S_1^{TD}$) of the second dopant.

17. The organic light emitting diode of claim 14, the emitting material layer further comprises a third emitting material layer disposed oppositely to the second emitting material layer with respect to the first emitting material layer.

18. The organic light emitting diode of claim 17, wherein the first emitting material layer comprises a first host and a first dopant, the second emitting material layer comprises a second host and a second dopant and the third emitting material layer includes a third host and a third dopant, and wherein an excited state singlet energy level ($S_1^{TD}$) of the first dopant is higher than each of excited state singlet energy levels ($S_1^{FD1}$ and $S_1^{FD2}$) of the second and third dopants, respectively.

19. The organic light emitting diode of claim 6, wherein the at least one emitting unit comprises a first emitting unit disposed between the first and second electrodes and a second emitting unit disposed between the first emitting unit and the second electrode, wherein the first emitting unit comprises a lower emitting material layer and the second emitting unit comprises an upper emitting material layer, and wherein at least one of the lower emitting material layer and the upper emitting material layer includes the organic compound, and the organic light emitting diode further comprises a charge generation layer disposed between the first and second emitting units.

20. An organic light emitting device, comprising:
a substrate;
a thin-film transistor on the substrate; and
the organic light emitting diode according to claim 6, wherein the organic light emitting diode is connected to the thin film transistor.

21. The organic compound of claim 1, wherein each of $X_1$, $X_3$ and $X_4$ is independently $CR_4$.

22. The organic light emitting diode of claim 6, wherein each of $X_1$, $X_3$ and $X_4$ is independently $CR_4$.

* * * * *